(12) United States Patent
Furebring et al.

(10) Patent No.: US 8,552,149 B2
(45) Date of Patent: Oct. 8, 2013

(54) POLYPEPTIDES AND USE THEREOF

(75) Inventors: Christina Furebring, Lund (SE); Anna Rosén, S. Sandby (SE); Karin Haraldsson, Lund (SE); Erika Gustafsson, Bjarred (SE); Björn Ulrik Walse, Lund (SE)

(73) Assignee: Alligator Bioscience AB, Lund (SE)

( * ) Notice: Subject to any disclaimer, the term of this patent is extended or adjusted under 35 U.S.C. 154(b) by 0 days.

(21) Appl. No.: 13/142,835

(22) PCT Filed: Nov. 30, 2009

(86) PCT No.: PCT/GB2009/002782
§ 371 (c)(1),
(2), (4) Date: Sep. 22, 2011

(87) PCT Pub. No.: WO2010/079314
PCT Pub. Date: Jul. 15, 2010

(65) Prior Publication Data
US 2012/0071394 A1    Mar. 22, 2012

Related U.S. Application Data

(60) Provisional application No. 61/193,926, filed on Jan. 8, 2009.

(30) Foreign Application Priority Data

Apr. 3, 2009 (GB) .................................. 0905790.2

(51) Int. Cl.
*A61K 38/16* (2006.01)
*A61P 9/00* (2006.01)
*C07K 14/00* (2006.01)

(52) U.S. Cl.
USPC .......................................... 530/324; 514/16.4

(58) Field of Classification Search
None
See application file for complete search history.

(56) References Cited

U.S. PATENT DOCUMENTS

| | | |
|---|---|---|
| 4,440,859 A | 4/1984 | Rutter et al. |
| 4,485,045 A | 11/1984 | Regen |
| 4,530,901 A | 7/1985 | Weissmann |
| 4,544,545 A | 10/1985 | Ryan et al. |
| 4,582,800 A | 4/1986 | Crowl |
| 4,677,063 A | 6/1987 | Mark et al. |
| 4,678,751 A | 7/1987 | Goeddel |
| 4,704,362 A | 11/1987 | Itakura et al. |
| 4,710,463 A | 12/1987 | Murray |
| 4,757,006 A | 7/1988 | Toole, Jr. et al. |
| 4,766,075 A | 8/1988 | Goeddel et al. |
| 4,810,648 A | 3/1989 | Stalker |
| 5,874,219 A | 2/1999 | Rava et al. |
| 6,027,726 A | 2/2000 | Ansell |
| 6,139,869 A | 10/2000 | Hosokawa et al. |

FOREIGN PATENT DOCUMENTS

| | | |
|---|---|---|
| EP | 1 586 583 A2 | 10/2005 |
| EP | 1 586 583 A3 | 10/2005 |
| GB | 0607798.6 | 4/2006 |
| WO | WO-98/58080 A1 | 12/1998 |
| WO | WO-00/02913 A1 | 1/2000 |
| WO | WO-01/49711 A2 | 7/2001 |
| WO | WO-01/49711 A3 | 7/2001 |
| WO | WO-02/48351 A2 | 6/2002 |
| WO | WO-02/48351 A3 | 6/2002 |
| WO | WO-03/097834 A2 | 11/2003 |
| WO | WO-03/097834 A3 | 11/2003 |
| WO | WO-2005/100385 A2 | 10/2005 |
| WO | WO-2005/100385 A3 | 10/2005 |
| WO | WO-2007/057682 A1 | 5/2007 |
| WO | WO-2007/122400 A2 | 11/2007 |
| WO | WO-2007/122400 A3 | 11/2007 |
| WO | WO-2007/122400 A9 | 11/2007 |
| WO | WO-2007/122400 C2 | 11/2007 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitut~ons in Each Repeat, J. Mol. BloL (2002) 324, 373-386.*
Aiyar, A. (2000). "The Use of CLUSTAL W and CLUSTAL X for Multiple Sequence Alignment," Chapter 11 in *Methods in Molecular Biology,* Misner, S. et al. eds., Humana Press Inc.: Totowa, NY 132:221-241.
Amitai, G. et al. (2004). "Network Analysis of Protein Structures Identifies Functional Residues," *J. Mol. Biol.* 344:1135-1146.
Becker, D.M. et al. (1991). "High-Efficiency Transformation of Yeast by Electroporation," *Methods Enzymolology,* Academic Press: New York, NY, 194:182-187.
Beggs, J.D. (Sep. 14, 1978). "Transformation of Yeast by a Replicating Hybrid Plasmid," *Nature* 275:104-109.

(Continued)

*Primary Examiner* — Julie Ha
*Assistant Examiner* — Li Ni Komatsu
(74) *Attorney, Agent, or Firm* — Morrison & Foerster LLP

(57) ABSTRACT

The present invention provides a polypeptide having a biological activity of the Chemotaxis Inhibitory Protein of *Staphylococcus aureus* ('CHIPS'), the polypeptide comprising or consisting of the amino acid sequence of SEQ ID NO: 2, or a fragment or variant thereof having a biological activity of CHIPS, wherein the fragment or variant retains amino acid substitutions K40E, D42V, N77H, K100R, K105R, N111 K and/or G112A relative to the wildtype CHIPS protein of SEQ ID NO:1. In one embodiment, polypeptide consists of the amino acid sequence of SEQ ID NO: 2. Related aspects of the invention provide pharmaceutical compositions comprising a polypeptide of the invention, together with methods or making and using the same.

9 Claims, 28 Drawing Sheets

(56) References Cited

OTHER PUBLICATIONS

Figure 1:
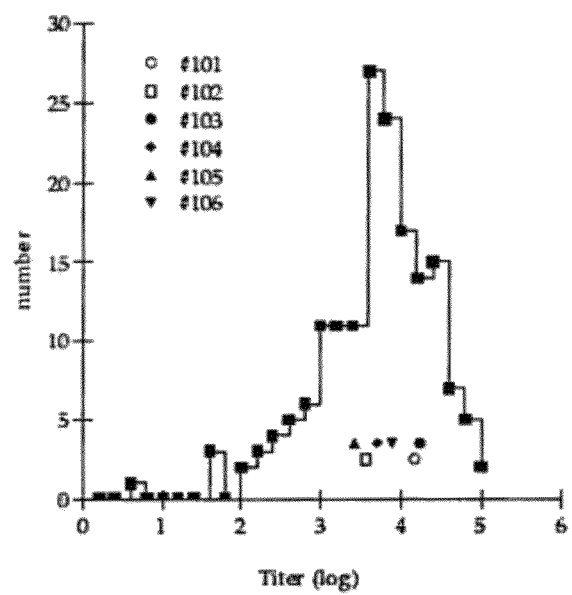

Berent, S.L. et al. (May/Jun. 1985). "Comparison of Oligonucleotide and Long DNA Fragments as Probes in DNA and RNA Dot, Southern, Northern, Colony and Plaque Hybridizations," *Biotech.* 3:208-220.

Cohen, S.N. et al. (Aug. 1972). "Nonchromosomal Antibiotic Resistance in Bacteria: Genetic Transformation of *Escherichia coli* by R-Factor DNA," *Proc. Natl. Acad. Sci. USA* 69(8):2110-2114.

Cook, A.D. et al. (1998). "Mimotopes Identified by Phage Display for the Monoclonal Antibody CII-C1 to Type II Collagen," *J. Autoimmun.* 11:205-211.

Crum, N.F. et al. (Sep. 2005). "Infections Associated With Tumor Necrosis Factor-α Antagonists," *Medicine* 84(5):291-301.

Dahlén, E. et al. (2008). "Development of Interleukin-1 Receptor Antagonist Mutants with Enhanced Antagonistic Activity In Vitro and Improved Therapeutic Efficacy in Collagen-Induced Arthritis," *J. Immunotoxicol.* 5:189-199.

De Haas, C.J.C. et al. (Mar. 1, 2004). "Chemotaxis Inhibitory Protein of *Staphylococcus aureus*, a Bacterial Antiinflammatory Agent," *J. Exp. Med.* 199(5):687-695.

Delano Scientific LLC. (2008). "PyMOL Molecular Viewer—SourceForge," located at <http://pymol.sourceforge.net>, last visited on Mar. 11, 2009, one page. [2002 date of software availability].

Engberg, J. et al. (1996). "Phage-Display Libraries of Murine and Human Antibody Fab Fragments," *Mol. Biotechnol.* 6:287-310.

Eppstein, D.A. et al. (Jun. 1985). "Biological Activity of Liposome-Encapsulated Murine Interferon γ is Mediated by a Cell Membrane Receptor," *Proc. Natl. Acad. Sci. USA* 82:3688-3692.

Falk, W. et al. (May 1982). "Only the Chemotactic Subpopulation of Human Blood Monocytes Expresses Receptors for the Chemotactic Peptide *N*-Formyl methionyl-Leucyl-Phenylalanine," *Infect. Immun.* 36(2):450-454.

Gunnarsson, L.C. et al. (2004, e-pub. Apr. 13, 2004). "A Carbohydrate Binding Module as a Diversity-Carrying Scaffold," *Protein Eng. Des. Sel.* 17(3):213-221.

Guo, R-F. et al. (Jan. 2004). "Role of C5a-C5aR Interaction in Sepsis," *Shock* 21(1):1-7.

Haas, P-J. et al. (2004). "N-Terminal Residues of the Chemotaxis Inhibitory Protein of *Staphylococcus aureus* Are Essential for Blocking Formylated Peptide Receptor but Not C5a Receptor," *The Journal of Immunology* 173:5704-5711.

Haas, P-J. et al. (2005, e-pub. Sep. 23, 2005). "The Structure of the C5a Receptor-Blocking Domain of Chemotaxis Inhibitory Protein of *Staphylococcus aureus* is Related to a Group of Immune Evasive Molecules," *J. Mol. Biol.* 353:859-872.

Heller, T. et al. (1999). "Selection of a C5a Receptor Antagonist From Phage Libraries Attenuating the Inflammatory Response in Immune Complex Disease and Ischemia/Reperfusion Injury," *The Journal of Immunology* 163:985-994.

Ho, S.N. et al. (1989). "Site-Directed Mutagenesis by Overlap Extension Using the Polymerase Chain Reaction," *Gene* 77:51-59.

Huang, X. et al. (1991). "A Time-Efficient, Linear-Space Local Similarity Algorithm," *Adv. Appl. Math.* 12:337-357.

Hubbard, S.J. et al. (1991). "Molecular Recognition: Conformational Analysis of Limited Proteolytic Sites and Serine Proteinase Protein Inhibitors," *J. Mol. Biol.* 220:507-530.

Huber-Lang, M. et al. (2001). "Role of C5a in Multiorgan Failure During Sepsis," *J. Immunol.* 166:1193-1199.

Huey, R. et al. (Sep. 1985). "Characterization of a C5a Receptor on Human Polymorphonuclear Leukocytes (PMN)," *J. Immunol.* 135(3):2063-2068.

Hwang, K.J. et al. (Jul. 1980). "Hepatic Uptake and Degradation of Unilamellar Sphingomyelin/Cholesterol Liposomes: A Kinetic Study," *Proc. Natl. Acad. Sci. USA* 77(7):4030-4034.

International Conference on Harmonisation. (Jun. 10, 1996). "ICH Harmonised Tripartite Guideline: Guideline for Good Clinical Practice. E6(R1) Step 4 Version," *presented at the ICH Steering Committee Meeting of the International Conference on Harmonisation of Technical Requirements for Registration of Pharmaceuticals for Human Use* on May 1, 1996, pp. 1-53.

Jancar, S. et al. (Jan. 2005, e-pub. Nov. 24, 2004). "Immune Complex-Mediated Tissue Injury: A Multistep Paradigm," *Trends in Immunol.* 26(1):48-55.

Johannes, T.W. et al. (2006, e-pub. Apr. 18, 2006). "Directed Evolution of Enzymes and Biosynthetic Pathways," *Curr. Opin. Microbiol.* 9:261-267.

Johansen, L.K. et al. (1995). "pFab60: A New, Efficient Vector for Expression of Antibody Fab Fragments Displayed on Phage," *Protein Engineering* (10):1063-1067.

Knecht, W. et al. (2006). "Limited Mutagenesis Increases the Stability of Human Carboxypeptidase U (TAFIa) and Demonstrates the Importance of CPU Stability Over proCPU Concentration in Down-Regulating Fibrinolysis," *FEBS J.* 273:778-792.

Le, Y. et al. (Nov. 2002, e-pub. Oct. 4, 2002). "Formyl-Peptide Receptors Revisited," *Trends Immunol.* 23(11):541-548.

Lee, B et al. (1971). "The Interpretation of Protein Structures: Estimation of Static Accessibility," *J. Mol. Biol.* 55:379-400.

Leung, D.W. et al. (Aug. 1989). "A Method for Random Mutagenesis of a Defined DNA Segment Using a Modified Polymerase Chain Reaction," *Technique* 1(1):11-15.

Listing, J. et al. (Nov. 2005). "Infections in Patients With Rheumatoid Arthritis Treated With Biologic Agents," *Arthritis Rheum.* 52(11):3403-3412.

Luchansky, J.B. et al. (1988). "Application of Electroporation for Transfer of Plasmid DNA to *Lactobacillus, Lactococcus, Leuconostoc, Listeria, Pediococcus, Bacillus, Staphylococcus, Enterococcus* and *Propionibacterium*," *Mol. Microbiol.* 2(5):637-646.

Myers, M.A. et al. (2000). "Conformational Epitopes on the Diabetes Autoantigen GAD65 Identified by Peptide Phage Display annd Molecular Modeling," *J. Immunol.* 165:3830-3838.

Payne, V. et al. (2004). "Mast Cell Tryptase: A Review of Its Physiology and Clinical Significance," *Anaesthesia* 59:695-703.

Pearson, W. (2009). "LALIGN—Find Multiple Matching Subsegments in Two Sequences," located at <http://www.ch.embnet.org/software/LALIGN_form.html>, lasted visited on Mar. 11, 2009, two pages.

Peters, E.A. et al. (Jul. 1994). "Membrane Insertion Defects Caused by Positive Charges in the Early Mature Region of Protein pill of Filamentous Phage fd Can Be Corrected by *prlA* Suppressors," *J. Bacteriol.* 176(14):4296-4305.

Pike, M.C. et al. (Jul. 1, 1980). "Development of Specific Receptors for *N*-Formylated Chemotactic Peptides in a Human Monocyte Cell Line Stimulated with Lymphokines," *J. Exp. Med.* 152:31-40.

Plant, A.L. et al. (1995). "Phospholipid/Alkanethiol Bilayers for Cell-Surface Receptor Studies by Surface Plasmon Resonance," *Analyt. Biochem.* 226(2):342-348.

Postma, B. et al. (2004). "Chemotaxis Inhibitory Protein of *Staphylococcus aureus* Binds Specifically to the C5a and Formylated Peptide Receptor," *The Journal of Immunology* 172:6994-7001.

Ricklin, D. et al. (Nov. 2007, e-pub. Nov. 7, 2007). "Complement-Targeted Therapeutics," *Nat. Biotechnol.* 25(11):1265-1275.

Schluederberg, S.A. et al. (Feb. 21, 1980). "Recovery Frequency of Phages λ and M13 from Human and Animal Faeces," *Nature* 283:792-794.

Shaw, D.M. et al. (2002). "Glycosylation and Epitope Mapping of the 5T4 Glycoprotein Oncofoetal Antigen," *Biochem. J.* 363:137-145.

Smith, G.P. et al. (1997). "Phage Display," *Chem. Rev.* 97(2):391-410.

Southern, E.M. (1975). "Detection of Specific Sequences Among DNA Fragments Separated by Gel Electrophoresis," *J. Mol. Biol.* 98:503-517.

Stemmer, W.P.C. (Aug. 4, 1994). "Rapid Evolution of a Protein in vitro by DNA Shuffling," *Nature* 370:389-391.

Stemmer, W.P.C. (Oct. 1994). "DNA Shuffling by Random Fragmentation and Reassembly: In vitro Recombination for Molecular Evolution," *Proc. Natl. Acad. Sci. USA* 91:10747-10751.

Van Epps, D.E. et al. (Jan. 1, 1993). "Relationship of C5a Receptor Modulation to the Functional Responsiveness of Human Polymorphonuclear Leukocytes to C5a," *J. Immunol.* 150(1):246-252.

Veldkamp, K.E. et al. (1997). "Staphylococcal Culture Supernates Stimulate Human Phagocytes," *Inflammation* 21(5):541-551.

(56) References Cited

OTHER PUBLICATIONS

Veldkamp, K.E. et al. (Oct. 2000). "Modulation of Neutrophil Chemokine Receptors by *Staphylococcus aureus* Supernate," *Infection and Immunity* 68(10):5908-5913.

Wong, T.S. et al. (2007). "Steering Directed Protein Evolution: Strategies to Manage Combinatorial Complexity of Mutant Libraries," *Environ. Microbiol.* 9(11):2645-2659.

World Medical Organization. (Dec. 7, 1996). "Declaration of Helsinki (1964)," *Brit. Med. J.* 313(7):1448-1449, located at <http://www.cirp.org/library/ethics/helsinki/>, last visited on Mar. 10, 2009, four pages.

Wu, X-C. et al. (Mar. 1998). "Engineering of Plasmin-Resistant Forms of Streptokinase and Their Production in *Bacillus subtilis*: Streptokinase with Longer Functional Half-Life," *Appl. Environ. Microbiol.* 64(3):824-829.

Yang, W-J. et al. (2005, e-pub. Jul. 1, 2005). "Epitope Mapping of *Mycoplasma hyopneumoniae* Using Phage Displayed Peptide Libraries and the Immune Responses of the Selected Phagotopes," *J. Immunol. Methods* 304:15-29.

Yuan, L. et al. (Sep. 2005). "Laboratory-Directed Protein Evolution," *Microbiol. Mol. Biol. Rev.* 69(3):373-392.

Zhao, H. et al. (Mar. 1998). "Molecular Evolution by Staggered Extension Process (StEP) in vitro Recombination," *Nat. Biotechnol.* 16:258-261.

Zhao, H. (Oct. 1, 2007). "Directed Evolution of Novel Protein Functions," *Biotechnol. Bioeng.* 98(2):313-317.

International Search Report mailed on Jul. 22, 2010, for PCT Patent Application No. PCT/GB2009/002782, filed on Nov. 30, 2009, 6 pages.

Barnum, S.R. (2002). "Complement in Central Nervous System Inflammation," *Immunologic Research* 26/1(3):7-13.

Bertolotto, A. et al. (2000). "Interferon β Neutralizing Antibodies in Multiple Sclerosis: Neutralizing Activity and Cross-Reactivity with Three Different Preparations," *Immunopharmacology* 48:95-100.

Buskirk, A.R. et al. (Jul. 20, 2004). "Directed Evolution of Ligand Dependence: Small-Molecule-Activated Protein Splicing," *PNAS* 101(29):10505-10510.

Buskirk, A.R. et al. (Aug. 2004). "Engineering a Ligand-Dependent RNA Transcriptional Activator," *Chemistry & Biology* 11:1157-1163.

Cicortas, L. et al. (2004, e-pub. Apr. 13, 2004). "A Carbohydrate Binding Module as a Diversity-Carrying Scaffold," *Protein Engineering, Design & Selection* 17(3):213-221.

Claeys, M.J. et al. (Apr. 20, 1999). "Determinants and Prognostic Implications of Persistent ST-Segment Elevation After Primary Angioplasty for Acute Myocardial Infarction: Importance of Microvascular Reperfusion Injury on Clinical Outcome," *Circulation* 99:1972-1977.

De Groot, A.S. et al. (2001). "From Genome to Vaccine: In Silico Predictions, Ex Vivo Verification," *Vaccine* 19:4385-4395.

DeLano Scientific LLC. (2012). "A User-Sponsored Molecular Visualization System on an Open-Source Foundation," located at <http://pymol.org/>, last visited on Oct. 17, 2012, one page.

Desmet, J. et al. (2002). "Fast and Accurate Side-Chain Topology and Energy Refinement (FASTER) as a New Method for Protein Structure Optimization," *Proteins: Structure, Function, and Genetics* 48:31-43.

Desmet, J. et al. (2005). "Anchor Profiles of HLA-Specific Peptides: Analysis by a Novel Affinity Scoring Method and Experimental Validation," *Proteins: Structure, Function, and Bioinformatics* 58:53-69.

Erlandsson, E. et al. (2003). "Identification of the Antigenic Epitopes in Staphylococcal Enterotoxins A and E and Design of a Superantigen for Human Cancer Therapy," *Journal of Molecular Biology* 333:893-905.

Farzan, M. et al. (May 7, 2001). "Sulfated Tyrosines Contribute to the Formation of the C5a Docking Site of the Human C5a Anaphylatoxin Receptor," *J. Exp. Med.* 193(9):1059-1065.

Fiser, S.M. et al. (Jun. 2001). "Lung Transplant Reperfusion Injury Involves Pulmonary Macrophages and Circulating Leukocytes in a Biphasic Response," *The Journal of Thoracic and Cardiovascular Surgery* 121(6):1069-1075.

Fiser, S.M. et al. (2002). "Ischemia-Reperfusion Injury After Lung Transplantation Increases Risk of Late Bronchiolitis Obliterans Syndrome," *The Annals of Thoracic Surgery* 73:1041-1048.

Fox, K.A.A. et al. (Oct. 10, 2006). "Prediction of Risk of Death and Myocardial Infarction in the Six Months After Presentation with Acute Coronary Syndrome: Prospective Multinational Observational Study (GRACE)," *BMJ*, six pages.

Gafvelin, G. et al. (Feb. 9, 2007). "Hypoallergens for Allergen-Specific Immunotherapy by Directed Molecular Evolution of Mite Group 2 Allergens," *The Journal of Biological Chemistry* 282(6):3778-3787.

Gotberg, M. et al. (2008). "Rapid Short-Duration Hypothermia with Cold Saline and Endovascular Cooling Before Reperfusion Reduces Microvascular Obstruction and Myocardial Infarct Size," *BMC Cardiovascular Disorders,* ten pages.

Granton, J. (2006). "Update of Early Respiratory Failure in the Lung Transplant Recipient," *Current Opinion in Critical Care* 12:19-24.

Guo, R.F. et al. (2005, e-pub. Jan. 7, 2005). "Role of C5A in Inflammatory Responses," *Annual Review of Immunology* 23:821-852.

Gustafsson, E. et al. (2009, e-pub. Oct. 5, 2008). "Purification of Truncated and Mutated Chemotaxis Inhibitory Protein of *Staphylococcus aureus*—an Anti-Inflammatory Protein," *Protein Expression and Purification* 63:95-101.

Gustafsson, E. et al. (2010, e-pub. Dec. 3, 2009). "Directed Evolution of Chemotaxis Inhibitory Protein of *Staphylococcus aureus* Generates Biologically Functional Variants with Reduced Interaction with Human Antibodies," *Protein Engineering, Design & Selection* 23(2):91-101.
Hedström, E. (2005). Acute Myocardial Infarction: The Relationship between Duration of Ischaemia and Infarct Size in Humans—Assessment by MRI and SPECT, *Doctoral Thesis—Lund University,* sixty pages.
Hedström, E. et al. (2007). Myocardial Infarct Size in Relation to Myocardium at Risk Versus Duration of Ischemia in Humans: Comparison with Different Species, *Saturday Poster Abstracts* 517:363.
Heiberg, E. et al. (2005). "Semi-Automatic Quantification of Myocardial Infarction from Delayed Contrast Enhanced Magnetic Resonance Imaging," *Scandinavian Cardiovascular Journal* 39:267-275.
International Preliminary Report on Patentability mailed on Jul. 12, 2011, for PCT Application No. PCT/GB2009/002782, filed on Nov. 30, 2009, 9 pages.
Ippel, J.H. et al. (2009). "Structure of the Tyrosine-Sulfated C5a Receptor N Terminus in Complex with Chemotaxis Inhibitory Protein of *Staphylococcus aureus," Journal of Biological Chemistry* 284(18):12363-12372.
Jaffe, R. et al. (Jun. 17, 2008). "Microvascular Obstruction and the No-Reflow Phenomenon After Percutaneous Coronary Intervention," *Circulation* 117:3152-3156.
Jongerius, I. et al. (Oct. 1, 2007). "Staphylococcal Complement Evasion by Various Convertase-blocking Molecules," *JEM* 204(10):2461-2471.
Keyt, B.A. et al. (Apr. 1994). "A Faster-Acting and More Potent Form of Tissue Plasminogen Activator," *Proceedings of the National Academy of Sciences of the United States of America* 91:3670-3674.
Kim, R.J. et al. (1999). "Relationship of MRI Delayed Contrast Enhancement to Irreversible Injury, Infarct Age, and Contractile Function," *Circulation* 100:1992-2002.
Köhl, J. (2001). "Anaphylatoxins and Infectious and Non-Infectious Inflammatory Diseases," *Molecular Immunology* 38:175-187.
Koren, E. et al. (2007, e-pub. May 9, 2007). "Clinical Validation of the "In Silico" Prediction of Immunogenicity of a Human Recombinant Therapeutic Protein," *Clinical Immunology* 124:26-32.
Laubach, V.E. et al. (Jul. 2009). "Pulmonary Inflammation After Lung Transplantation," *Surgery* 146(1):1-4.
Lingen, B. et al. (2002). "Improving the Carboligase Activity of Benzoylformate Decarboxylase from *Pseudomonas putida* by a Combination of Directed Evolution and Site-directed Mutagenesis," *Protein Engineering* 15(7):585-593.

(56) References Cited

OTHER PUBLICATIONS

Linhart, B. et al. (Jul. 2008). "A Hypoallergenic Hybrid Molecule with Increased Immunogenicity Consisting of Derivatives of the Major Grass Pollen Allergens, Phl p 2 and Phl p 6," *Biological Chemistry* 389:925-933.

McGregor, C.G.A. et al. (1994). "Evolving Strategies in Lung Transplantation for Emphysema," *The Annals of Thoracic Surgery* 57:1513-1520.

Monk, P.N. et al. (2007, e-pub. Jul. 2, 2007). "Function, Structure and Therapeutic Potential of Complement C5a Receptors," *British Journal of Pharmacology* 152:429-448.

Mothes-Luksch, N. et al. (2008). "Disruption of Allergenic Activity of the Major Grass Pollen Allergen Phl p 2 by Reassembly as a Mosaic Protein," *The Journal of Immunology* 181:4864-4873.

Okusawa, S. et al. (Jul. 1988). "C5a Stimulates Secretion of Tumor Necrosis Factor from Human Mononuclear Cells In Vitro: Comparison with Secretion of Interleukin 1β and Interleukin 1α," *Journal of Experimental Medicine* 168:443-448.

Reetz, M.T. (Apr. 20, 2004). "Controlling the Enantioselectivity of Enzymes by Directed Evolution: Practical and Theoretical Ramifications," *PNAS* 101(16):5716-5722.

Rittirsch, D. et al. (May 2008). "Functional Roles for C5a Receptors in Sepsis," *Nature Medicine* 14(5):551-557.

Rooijakkers, S.H.M. et al. (Sep. 2005, e-pub. Aug. 7, 2005). "Immune Evasion by a Staphylococcal Complement Inhibitor that Acts on C3 Convertases," *Nature Immunology* 6(9):920-927.

Ross, S.D. et al. (1999). "Reduced Neutrophil Infiltration Protects Against Lung Reperfusion Injury After Transplantation," *The Annals of Thoracic Surgery* 67:1428-1433.

Schellekens, H. (2003). "Immunogenicity of Therapeutic Proteins," *Nephrology, Dialysis, Transplantation* 18:1257-1259.

Segment, "Segment Home Page," located at http://segment.heiberg.se/, last visited on Oct. 17, 2012, two pages.

Steen, S. et al. (1994). "Safe Lung Preservation for Twenty-Four Hours With Perfadex," *The Annals of Thoracic Surgery* 57:450-457.

Sumichika, H. (2004). "C5a Receptor Antagonists for the Treatment of Inflammation," *Current Opinion in Investigational Drugs* 5(5):505-510.

Szalai, K. et al. (2008). "Mimotopes Identify Conformational B-Cell Epitopes on the Two Major House Dust Mite Allergens Der p 1 and Der p 2," *Molecular Immunology* 45:1308-1317.

The Lancet (Aug. 13, 1988). "Randomised Trial of Intravenous Streptokinase, Oral Aspirin, Both, or Neither Among 17 187 Cases of Suspected Acute Myocardial Infarction: ISIS-2," *The Lancet* 349-360.

Tomizawa, N. et al. (Jul. 1999). "The Effects of a Neutrophil Elastase Inhibitor (ONO-5046 NA) and Neutrophil Depletion Using a Granulotrap (G-1) Column on Lung Reperfusion Injury in Dogs," *The Journal of Heart and Lung Transplantation* 18(7):637-645.

Ugander, M. et al. (2008). "The Novel Method for Qualifying Myocardial Perfusion SPECT Defect Size by Co-registration and Fusion with MRI-an Experimental Ex Vivo Imaging Pig Heart Study," 97:47-48, Abstract No. A13511.

Van Walle, I. et al. (2007). "Immunogenicity Screening in Protein Drug Development," *Expert Opinion of Biological Therapy* 7(3):405-418.

Vrtala, S. et al. (2004). "Strategies for Converting Allergens into Hypoallergenic Vaccine Candidates," *Methods* 32:313-320.

Vucic, E. et al. (2007). "Apolipoprotein E Derived Peptide Containing Gadolinium Mixed Micelles for Macrophage Imaging in Atherosclerotic Plaque of Apoe −/− Mice," *Saturday Poster Abstracts* 518:363.

Wetsel, R.A. (1995). "Expression of the Complement C5a Anaphylatoxin Receptor (C5aR) on Non-Myeloid Cells," *Immunology Letters* 44:183-187.

Wright, A.J. et al. (2007). "Characterisation of Receptor Binding by the Chemotaxis Inhibitory Protein of *Staphylococcus aureus* and the Effects of the Host Immune Response," *Molecular Immunology* 44(10-4):2507-2517.

Written Opinion of the International Searching Authority mailed on Jul. 22, 2010, for PCT Application No. PCT/GB2009/002782 filed on Nov. 30, 2009, 8 pages.

Wu, K.C. et al. (1998). "Prognostic Significance of Microvascular Obstruction by Magnetic Resonance Imaging in Patients With Acute Myocardial Infarction,"*Circulation* 97:765-772.

Zwirner, J. et al. (1999). "Expression of the Anaphylatoxin C5a Receptor in Non-Myeloid Cells," *Molecular Immunology* 36:877-884.

\* cited by examiner (A)

(B)

(A) White Blood Cells (B) C-Reactive Protein (A) Circulating Immune Complexes (B) Serum Tryptase (A)

(B)

(C)

SEQ ID NO: 5

A

B

SEQUENCE LISTING

```
<160> NUMBER OF SEQ ID NOS: 12

<210> SEQ ID NO 1
<211> LENGTH: 121
<212> TYPE: PRT
<213> ORGANISM: Staphylococcus aureus

<400> SEQUENCE: 1

Phe Thr Phe Glu Pro Phe Pro Thr Asn Glu Glu Ile Glu Ser Asn Lys
1               5                   10                  15

Lys Met Leu Glu Lys Glu Lys Ala Tyr Lys Glu Ser Phe Lys Asn Ser
            20                  25                  30

Gly Leu Pro Thr Thr Leu Gly Lys Leu Asp Glu Arg Leu Arg Asn Tyr
        35                  40                  45

Leu Lys Lys Gly Thr Lys Asn Ser Ala Gln Phe Glu Lys Met Val Ile
    50                  55                  60
```

Leu Thr Glu Asn Lys Gly Tyr Tyr Thr Val Tyr Leu Asn Thr Pro Leu
 65                  70                  75                  80

Ala Glu Asp Arg Lys Asn Val Glu Leu Leu Gly Lys Met Tyr Lys Thr
                 85                  90                  95

Tyr Phe Phe Lys Lys Gly Glu Ser Lys Ser Ser Tyr Val Ile Asn Gly
            100                 105                 110

Pro Gly Lys Thr Asn Glu Tyr Ala Tyr
        115                 120

<210> SEQ ID NO 2
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 2

Asn Ser Gly Leu Pro Thr Thr Leu Gly Glu Leu Val Glu Arg Leu Arg
 1               5                  10                  15

Asn Tyr Leu Lys Lys Gly Thr Lys Asn Ser Ala Gln Phe Glu Lys Met
                20                  25                  30

Val Ile Leu Thr Glu Asn Lys Gly Tyr Tyr Thr Val Tyr Leu His Thr
            35                  40                  45

Pro Leu Ala Glu Asp Arg Lys Asn Val Glu Leu Leu Gly Lys Met Tyr
        50                  55                  60

Lys Thr Tyr Phe Phe Arg Lys Gly Glu Ser Arg Ser Ser Tyr Val Ile
 65                  70                  75                  80

Lys Ala Pro

<210> SEQ ID NO 3
<211> LENGTH: 38
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Forward PCR primer

<400> SEQUENCE: 3
tcgcggccca gccggccatg gcctttactt ttgaaccg                          38

<210> SEQ ID NO 4
<211> LENGTH: 35
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Reverse PCR primer

<400> SEQUENCE: 4
gcctgcggcc gcagatctac cattaattac ataag                             35

<210> SEQ ID NO 5
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide
<220> FEATURE:

```
<221> NAME/KEY: VARIANT
<222> LOCATION: 10
<223> OTHER INFORMATION: Xaa = Lys or Glu
<220> FEATURE:
<221> NAME/KEY: VARIANT
<222> LOCATION: 12
<223> OTHER INFORMATION: Xaa = Asp or Val
<220> FEATURE:
<221> NAME/KEY: VARIANT
<222> LOCATION: 20
<223> OTHER INFORMATION: Xaa = Lys or Asn
<220> FEATURE:
<221> NAME/KEY: VARIANT
<222> LOCATION: 39
<223> OTHER INFORMATION: Xaa = Lys, Ala or Arg
<220> FEATURE:
<221> NAME/KEY: VARIANT
<222> LOCATION: (47)...(47)
<223> OTHER INFORMATION: Xaa = Tyr or His
<220> FEATURE:
<221> NAME/KEY: VARIANT
<222> LOCATION: (62)...(62)
<223> OTHER INFORMATION: Xaa = Lys or Arg
<220> FEATURE:
<221> NAME/KEY: VARIANT
<222> LOCATION: (70)...(70)
<223> OTHER INFORMATION: Xaa = Lys or Arg
<220> FEATURE:
<221> NAME/KEY: VARIANT
<222> LOCATION: (75)...(75)
<223> OTHER INFORMATION: Xaa = Lys or Arg
<220> FEATURE:
<221> NAME/KEY: VARIANT
<222> LOCATION: (81)...(81)
<223> OTHER INFORMATION: Xaa = Lys or Ile
<220> FEATURE:
<221> NAME/KEY: VARIANT
<222> LOCATION: (82)...(82)
<223> OTHER INFORMATION: Xaa = Gly or Ala

<400> SEQUENCE: 5

Asn Ser Gly Leu Pro Thr Thr Leu Gly Xaa Leu Xaa Glu Arg Leu Arg
  1               5                  10                  15

Asn Tyr Leu Xaa Lys Gly Thr Lys Asn Ser Ala Gln Phe Glu Lys Met
                 20                  25                  30

Val Ile Leu Thr Glu Asn Xaa Gly Tyr Tyr Thr Val Tyr Leu Xaa Thr
             35                  40                  45

Pro Leu Ala Glu Asp Arg Lys Asn Val Glu Leu Leu Gly Xaa Met Tyr
 50                  55                  60

Lys Thr Tyr Phe Phe Xaa Lys Gly Glu Ser Xaa Ser Ser Tyr Val Ile
 65                  70                  75                  80

Xaa Xaa Pro

<210> SEQ ID NO 6
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 6

Asn Ser Gly Leu Pro Thr Thr Leu Gly Lys Leu Asp Glu Arg Leu Arg
  1               5                  10                  15

Asn Tyr Leu Lys Lys Gly Thr Lys Asn Ser Ala Gln Phe Glu Lys Met
                 20                  25                  30

Val Ile Leu Thr Glu Asn Lys Gly Tyr Tyr Thr Val Tyr Leu Asn Thr
             35                  40                  45
```

Pro Leu Ala Glu Asp Arg Lys Asn Val Glu Leu Leu Gly Lys Met Tyr
            50                  55                  60

Lys Thr Tyr Phe Phe Lys Gly Glu Ser Lys Ser Ser Tyr Val Ile
65                  70                  75                  80

Asn Gly Pro

<210> SEQ ID NO 7
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 7

Asn Ser Gly Leu Pro Thr Thr Leu Gly Glu Leu Val Glu Arg Leu Arg
1               5                   10                  15

Asn Tyr Leu Lys Lys Gly Thr Lys Asn Ser Ala Gln Phe Glu Lys Met
            20                  25                  30

Val Ile Leu Thr Glu Asn Ala Gly Tyr Tyr Thr Val Tyr Leu Tyr Thr
            35                  40                  45

Pro Leu Ala Glu Asp Arg Lys Asn Val Glu Leu Leu Gly Lys Met Tyr
            50                  55                  60

Lys Thr Tyr Phe Phe Arg Lys Gly Glu Ser Arg Ser Ser Tyr Val Ile
65                  70                  75                  80

Lys Ala Pro

<210> SEQ ID NO 8
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 8

Asn Ser Gly Leu Pro Thr Thr Leu Gly Glu Leu Val Glu Arg Leu Arg
1               5                   10                  15

Asn Tyr Leu Lys Lys Gly Thr Lys Asn Ser Ala Gln Phe Glu Lys Met
            20                  25                  30

Val Ile Leu Thr Glu Asn Lys Gly Tyr Tyr Thr Val Tyr Leu Tyr Thr
            35                  40                  45

Pro Leu Ala Glu Asp Arg Lys Asn Val Glu Leu Leu Gly Lys Met Tyr
            50                  55                  60

Lys Thr Tyr Phe Phe Arg Lys Gly Glu Ser Arg Ser Ser Tyr Val Ile
65                  70                  75                  80

Lys Ala Pro

<210> SEQ ID NO 9
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 9

Asn Ser Gly Leu Pro Thr Thr Leu Gly Lys Leu Val Glu Arg Leu Arg
1               5                   10                  15

Asn Tyr Leu Asn Lys Gly Thr Lys Asn Ser Ala Gln Phe Glu Lys Met
            20                  25                  30

Val Ile Leu Thr Glu Asn Arg Gly Tyr Tyr Thr Val Tyr Leu Tyr Thr
                35                  40                  45

Pro Leu Ala Glu Asp Arg Lys Asn Val Glu Leu Gly Arg Met Tyr
        50                  55                  60

Lys Thr Tyr Phe Phe Lys Lys Gly Glu Ser Lys Ser Ser Tyr Val Ile
65                  70                  75                  80

Lys Ala Pro

<210> SEQ ID NO 10
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 10

Asn Ser Gly Leu Pro Thr Thr Leu Gly Glu Leu Val Glu Arg Leu Arg
1               5                   10                  15

Asn Tyr Leu Lys Lys Gly Thr Lys Asn Ser Ala Gln Phe Glu Lys Met
            20                  25                  30

Val Ile Leu Thr Glu Asn Lys Gly Tyr Tyr Thr Val Tyr Leu Tyr Thr
                35                  40                  45

Pro Leu Ala Glu Asp Arg Lys Asn Val Glu Leu Gly Lys Met Tyr
        50                  55                  60

Lys Thr Tyr Phe Phe Lys Lys Gly Glu Ser Lys Ser Ser Tyr Val Ile
65                  70                  75                  80

Lys Ala Pro

<210> SEQ ID NO 11
<211> LENGTH: 83
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Variant CHIPS polypeptide

<400> SEQUENCE: 11

Asn Ser Gly Leu Pro Thr Thr Leu Gly Glu Leu Val Glu Arg Leu Arg
1               5                   10                  15

Asn Tyr Leu Lys Lys Gly Thr Lys Asn Ser Ala Gln Phe Glu Lys Met
            20                  25                  30

Val Ile Leu Thr Glu Asn Lys Gly Tyr Tyr Thr Val Tyr Leu Tyr Thr
                35                  40                  45

Pro Leu Ala Glu Asp Arg Lys Asn Val Glu Leu Gly Arg Met Tyr
        50                  55                  60

Lys Thr Tyr Phe Phe Lys Lys Gly Glu Ser Lys Ser Ser Tyr Val Ile
65                  70                  75                  80

Lys Ala Pro

<210> SEQ ID NO 12
<211> LENGTH: 83
<212> TYPE: PRT
<213> ORGANISM: Artificial Sequence
<220> FEATURE:
<223> OTHER INFORMATION: Synthetic Construct -continued

```
<220> FEATURE:
<223> OTHER INFORMATION: Variant CHIPS polypeptide

<400> SEQUENCE: 12

Asn Ser Gly Leu Pro Thr Thr Leu Gly Lys Leu Asp Glu Arg Leu Arg
 1               5                  10                  15

Asn Tyr Leu Asn Lys Gly Thr Lys Asn Ser Ala Gln Phe Glu Lys Met
            20                  25                  30

Val Ile Leu Thr Glu Asn Lys Gly Tyr Tyr Thr Val Tyr Leu Tyr Thr
        35                  40                  45

Pro Leu Ala Glu Asp Arg Lys Asn Val Glu Leu Leu Gly Arg Met Tyr
    50                  55                  60

Lys Thr Tyr Phe Phe Arg Lys Gly Glu Ser Lys Ser Ser Tyr Val Ile
65                  70                  75                  80

Ile Gly Pro
```

POLYPEPTIDES AND USE THEREOF

CROSS-REFERENCE TO RELATED APPLICATIONS

This application is a National Phase application under 35 U.S.C. §371 of International Application No. PCT/GB2009/002782 filed Nov. 30, 2009 and claims the benefit of Great Britain Application No. 0905790.2 filed Apr. 3, 2009 and claims the benefit of U.S. Provisional Application No. 61/193,926 filed Jan. 8, 2009, the disclosures of which are incorporated herein by reference in their entirety.

FIELD OF INVENTION

The present invention relates to novel polypeptides and their use in the treatment of conditions and diseases associated with activation of complement C5a receptors and/or formylated peptide receptors. In particular, the invention provides variant forms of the Chemotaxis Inhibitory Protein of *Staphylococcus aureus* ('CHIPS') and uses of the same in the treatment of acute and chronic inflammatory disorders.

INTRODUCTION

*Staphylococcus aureus* is a common human pathogen causing a variety of diseases. The mechanisms by which *S. aureus* causes disease are multi-factorial. With the exception of some staphylococcal diseases caused by specific toxins like Toxic Shock Syndrome Toxin (TSST-1), responsible for Toxic Shock syndrome, or enterotoxin, the pathogenicity of *S. aureus* infections does not depend on a single factor. *S. aureus* possesses a large variety of different 'tools' to cause disease. The whole complex of these different factors acting together facilitates colonisation, growth and spread within the host. Phagocytosis and killing of staphylococci by phagocytes is the most important host defense mechanism. Phagocytes are attracted to the site of infections by cytokines and chemokines released by the invader (like formylated peptides) and upon activation of inflammatory cascades like the complement system. The release of these chemoattractants creates a gradient by which the phagocytes are attracted to the site of inflammation.

The interaction of the supernate of growing *S. aureus* with phagocytes was studied by Veldkamp et al. They found that although staphylococcal supernate was able to stimulate phagocytes there also was a factor present that could specifically downregulate the expression of the complement C5a receptor (C5aR) and formylated peptide receptor (FPR) as detected by monoclonal antibodies (see Veldkamp et al., 2000, *Infect Immun* 68(10):5908-13; Veldkamp et al., 1997, *Inflammation* 21(5):541-51). From the supernate of *S. aureus* they isolated a 14.1 kDa protein responsible for this action; this protein was named CHIPS, CHemotaxis Inhibitory Protein of *Staphylococcus aureus*. CHIPS is able to inhibit neutrophil chemotaxis and activation with C5a and fMLP. Furthermore, CHIPS was found to be very selective, since it did not affect a broad selection of other receptors, including other chemoattractant receptors present on neutrophils, like the FPR-like 1, C3aR, IL-8RA and IL-8RB, LTB4 receptor, and PAF receptor. This indicates that CHIPS specifically inhibits two members of the G-protein coupled receptor family, the C5aR and the FPR. CHIPS is not toxic for the cells and also inhibits C5aR on other cells like monocytes and mast cells.

Postma et al. showed that CHIPS binds directly to both the C5aR and FPR in an energy independent way. Furthermore, CHIPS is not internalised upon binding to its receptors. CHIPS binds both receptors with apparent Kd values of 1.1 and 35.4 nM for the C5aR and FPR, respectively (see Postma et al., 2004, *J Immunol* 172(111:6994-7001). These Kd values are in the same range as those described for their natural ligands (see Van Epps et al., 1993, *J Immunol* 150(1):246-252; Falk et al., 1982, *Infect Immun* 36(2):450-454; Huey & Hugli, 1985, *Immunol.* 135(3):2063-8; Pike et al., 1980, *J Exp Med* 152(1):31-40). The active site in CHIPS for binding the formylated peptide receptor and C5a receptor are located within distinct regions of the CHIPS molecule. The N-terminal and C-terminal end and particularly the first and third amino acids are involved in the CHIPS activity towards the formylated peptide receptor (see Haas et al., 2004, *J Immunol* 173(9):5704-11). At least the first thirty N-terminal amino acids do not play a role in CHIPS binding and blocking the C5aR. Therefore, a CHIPS protein without the first 30 amino acids, $CHIPS_{31-121}$, shows a complete preservation of C5aR blocking activity but completely lost the activity towards the FPR (see Haas et al., 2005, *J Mol Biol* 353(4):859-872).

In recent years it has become clear that, next to host defense, chemokine receptors, like the FPR and C5aR, are also involved in a variety of other inflammatory processes. The recent identification of a variety of novel and host-derived agonists for the FPR has broadened the spectrum of functional significance of the FPR in disease processes (see Le et al., 2002, *Trends Immunol* 23(11):541-8). A lot of research has been done on the evident role of the C5aR in a wide range of different disease processes including; sepsis, ischemia-reperfusion injury, rheumatoid arthritis, asthma and immune complex disease. Various experimental studies with animal models demonstrated the beneficial effects of targeting the C5aR in these disease processes (see Guo et al., 2004, *Shock* 21(1):1-7; Huber-Lang et al., 2001, *J Immunol* 166(2):1193-1199; Heller et al., 1999, *J Immunol* 163(2):985-94). The unique properties of CHIPS to specifically inhibit the FPR and C5aR make this protein a promising candidate antiinflammatory drug in those diseases in which FPR or C5aR stimulation play an important role.

Experiments with isolated human and mouse neutrophils show that the activity of CHIPS for the mouse C5aR is at least 30 times lower than for the human receptor. The human specificity of CHIPS as shown by this 30-fold difference in activity toward human cells as compared to mouse cells hampers testing of CHIPS in a mouse infection model or other animal models.

*S. aureus* is a normal commensal of the human skin and minor skin or wound infections caused by *S. aureus* are normally self-limiting. *S. aureus* can potentially infect any tissue of the body and occasionally spreads from the primary site of infection to cause life-threatening diseases like osteomyelitis, endocarditis, pneumonia, and septicaemia. The CHIPS gene is present in the majority of clinical *S. aureus* strains and strains from healthy carriers and CHIPS is produced in vivo as described by de Haas et al., using a mouse infection model (see Haas et al., 2004, *J Exp Med* 199(5):687-95). Since *S. aureus* is a very common bacterium, it is likely that most individuals encounter *S. aureus* and the CHIPS protein early in life, leading to the production of anti-CHIPS antibodies.

The amino acid sequence of the wildtype CHIPS protein is shown below (in which amino acid numbers 31 to 113 are underlined):

SEQ ID NO: 1
FTFEPFPTNEEIESNKKMLEKEKAYKESFKNSGLPTTLGKLDERLRNYLKKGTKNSAQF

EKMVILTENKGYYTVYLNTPLAEDRKNVELLGKMYKTYFFKKGESKSSYVINGPGKTNE

YAY

The amino acid sequence of the wildtype CHIPS protein is also disclosed in Database Accessions Nos. AAQ14339, CAG41022 and YP_041409.

Various fragments, variants and derivatives of the wildtype CHIPS protein, and their uses, are disclosed in EP 1 095 059 A, EP 1 244 790 A, PCT/EP2005/004156 and PCT/EP2007/001443, the disclosures of which are incorporated herein by reference.

The present invention seeks to provide new therapeutic agents based on novel mutated versions of the wildtype CHIPS protein, which exhibit advantageous properties.

SUMMARY OF INVENTION

A first aspect of the invention provides a polypeptide having a biological activity of the Chemotaxis Inhibitory Protein of *Staphylococcus auras* ('CHIPS'), the polypeptide comprising or consisting of the amino acid sequence of SEQ ID NO: 2, or a fragment or variant thereof having a biological activity of CHIPS, wherein the fragment or variant retains amino acid substitutions K40E, D42V, N77H, K100R, K105R, N111K and/or G112A relative to the wildtype CHIPS protein of SEQ ID NO:1.

```
                                    SEQ ID NO: 2
NSGLPTTLGELVERLRNYLKKGTKNSAQFEKMVILTENKGYYTVYLHTPLAEDRKNVEL

LGKMYKTYFFRKGESRSSYVIKAP
```

It will be appreciated that SEQ ID NO: 2 corresponds to amino acids 31-113 of SEQ ID NO: 1 with the following amino acid substitutions; K40E, D42V, N77H, K100R, K105R, N111K and G 112A (see bold, underlined amino acids in SEQ ID NO:2).

It will be further appreciated that the polypeptide of SEQ ID NO: 2 may be expressed with or without an N-terminal methionine (not shown in SEQ ID NO:2). All references to a polypeptide of SEQ ID NO: 2 herein are to be construed accordingly.

For the avoidance of doubt, unless specified otherwise, in this specification the numbering of all amino acids with respect to CHIPS protein fragments, variants or derivatives etc is relative to the wildtype CHIPS protein (i.e. SEQ ID NO: 1). For example, a substitution K40E relative to SEQ ID NO: 1 corresponds to a lysine to glutamic acid substitution in the tenth amino acid of SEQ ID NO: 2 (since SEQ ID NO: 2 does not include the first 30 amino acids of SEQ ID NO: 1).

The first aspect of the invention encompasses fragments and variants of SEQ ID NO:2 having a biological activity of CHIPS, wherein the variant retains amino acid substitutions K40E, D42V, N77H, K100R, K105R, N111K and/or G112A relative to the wildtype CHIPS protein of SEQ ID NO:1. By "retains" in this context we mean that in the event that the variant comprises an amino acid corresponding to positions 40, 42, 77, 100, 105, 111 and/or 112 of SEQ ID NO:1, then that amino acid is glutamic acid, valine, histidine, arginine, arginine, lysine and/or alanine, respectively. For example, where the polypeptide is a variant of the 52 C-terminal amino acids of SEQ ID NO: 2, it contains a histidine at the amino acid corresponding to position 77 of SEQ ID NO:1, an arginine at the amino acid corresponding to position 100 of SEQ ID NO:1, an arginine at the amino acid corresponding to position 105 of SEQ ID NO:1, a lysine at the amino acid corresponding to position 111 of SEQ ID NO:1, and an alanine at the amino acid corresponding to position 77 of SEQ ID NO:1. However, since this exemplary variant lacks amino acids 1 to 51 of SEQ ID NO: 2, it does not contain an amino acid corresponding to position 40 or 42 of SEQ ID NO:1.

The polypeptide defined by SEQ ID NO: 2 contains 83 amino acids. However, it will be appreciated by persons skilled in the art that the polypeptides of the invention may be of greater or shorter length. For example, the polypeptides may comprise or consist of greater or fewer than 83 amino acids, or may comprise or consist of 83 amino acids exactly. Preferably, the polypeptide is fewer than 500 amino acids in length, for example fewer than 400, 300, 200, 150, 140, 130, 125, 121, 120, 119, 118, 117, 116, 115, 114, 113, 112, 111, 110, 109, 108, 107, 106, 105, 104, 103, 102, 101, 100, 95, 90, 85, 80, 79, 78, 77, 76, 75, 74, 73, 72, 71, 70, 65, 60, 55, 50, 40, 30 or fewer amino acids in length.

For example, the polypeptide may be between 70 and 110 amino acids in length, for example between 75 and 90 amino acids in length, e.g. 75, 76, 77, 78, 79, 80, 81, 82, 83, 84, 85, 86, 87, 88, 89 or 90 amino acids. In one embodiment, the polypeptide is 83 amino acids in length.

Thus, in one embodiment of the first aspect of the invention, the polypeptide comprises or consists of a fragment of the amino acid sequence of SEQ ID NO: 2, or variant thereof.

By "fragment" we include at least 10, 20, 30, 40, 50, 60, 70, 71, 72, 73, 74, 75, 76, 77, 78, 79, 80, 81 or 82 contiguous amino acids of the amino acid sequence of SEQ ID NO: 2.

In a further embodiment, the polypeptide comprises or consists of one or more additional amino acids, inserted at the N- and/or C-terminus or internally within the amino acid sequence of SEQ ID NO: 2. For example, the polypeptide may comprises or consist of at least 2, 3, 4, 5, 6, 7, 8, 9, 10, 15 or 20 additional amino acids. Advantageously, the additional amino acids are located at the C-terminus of the amino acid sequence of SEQ ID NO: 2.

In a still further embodiment of the first aspect of the invention, the polypeptide comprises or consists of a variant of the amino acid sequence of SEQ ID NO: 2, or of a fragment thereof.

By "variant" we mean that the polypeptide does not share 100% amino acid sequence identity with SEQ ID NO: 2, i.e. one or more amino acids of SEQ ID NO: 2 must be modified. For example, the polypeptide may comprise an amino acid sequence with at least 60% identity to the amino acid sequence of SEQ ID NO: 2, more preferably at least 70% or 80% or 85% or 90% identity to said sequence, and most preferably at least 95%, 96%, 97%, 98% or 99% identity to said amino acid sequence.

Percent identity can be determined by methods well known in the art, for example using the LALIGN program (Huang and Miller, Adv. Appl. Math. (1991) 12:337-357) at the Expasy facility site (worldwide web at ch.embnet.org/software/LALIGN_form-.html) using as parameters the global alignment option, scoring matrix BLOSUM62, opening gap penalty −14, extending gap penalty −4.

Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

By "modified" we mean that the amino acid at the specified position is altered compared to the amino acid in the polypeptide according to SEQ ID NO: 2. For example, the amino acid at the specified position may be non-natural, deleted, or substituted or may be the site of an insertion/addition of one or more amino acids. It will be appreciated by persons skilled in the art that the substitutions may be conservative or non-conservative.

In one embodiment, the variant comprises or consists of an amino acid sequence of SEQ ID NO: 2, or a fragment thereof, in which one or more amino acids is conservatively substituted. By "conservatively substituted" we mean a substitution of one amino acid with another with similar properties (size, hydrophobicity, etc), such that the function of the polypeptide is not significantly altered. Thus, by "conservative substitutions" is intended combinations such as Gly, Ala; Val, Ile, Leu; Asp, Glu; Asn, Gln; Ser, Thr, Lys, Arg; and Phe, Tyr.

In a further embodiment, the variant comprises a modification at one or more amino acids exposed at the polypeptide surface. Surface exposed amino acids may be determined using techniques well known in the art (see Example B). However, it will be appreciated that modification of a non-exposed amino acid may also result in a structural change at the surface of the variant polypeptide (relative to the wildtype CHIPS protein or the polypeptide according to SEQ ID NO: 2).

It will be appreciated by skilled persons that the amino acid molecules may also be modified in other ways, for example by chemical modification. Thus, the polypeptides of the present invention may be composed of amino acids joined to each other by peptide bonds or modified peptide bonds, e.g. peptide esters, and contain amino acids other than the 20 gene-encoded amino acids. For example, the polypeptides may contain L-amino acids and/or D-amino acids, as well as modified amino acids such as hydroxyproline, γ-carboxy glutamate, O-phosphoserine and O-phosphotyrosine. The polypeptides may be modified by natural processes, such as post-translational modification, or by chemical modification techniques well known in the art. Modifications can occur anywhere within the amino acid sequence of the variant CHIPS polypeptide, including the peptide backbone, the amino acid side chains and the amino- or carboxy-termini.

In one embodiment, however, the polypeptides of the present invention comprise or consist of natural L-amino acids.

Modified or variant forms of a known polypeptide can be produced using techniques well known in the art (see Sambrook & Russell, 2000, *Molecular Cloning, A Laboratory Manual*, Third Edition, Cold Spring Harbor, N.Y., which is incorporated herein by reference). For example, point mutations may be introduced at specific amino acid residues by site-directed mutagenesis (see Sambrook & Russell, supra, Chapter 13). Additional methods for generating variants of a parent polynucleotide are described below.

As used herein, "biological activity" with respect to CHIPS refers to an effect of the wildtype CHIPS protein upon a living organism, tissue or cell. Included herein, but not limited to, is binding to a natural ligand or ligands, as well as down-stream events therefrom, causing direct or indirect effects on a living organism. Thus, by "a biological activity" of the CHIPS protein we include inhibition of the chemotaxis and/or activation of neutrophils induced by the complement component C5a and/or the N-formyl-peptide, fMLP. For example, the maintained activity may comprise antagonism of the C5a receptor (C5aR) and/or antagonism of the formylated peptide receptor (FPR).

In one embodiment, however, the variant CHIPS polypeptide of the present invention lacks the FPR binding site (e.g. the polypeptide lacks amino acids 1 to 30 of SEQ ID NO:1).

In a further embodiment, the polypeptide of the invention exhibits one or more biological activities of the CHIPS protein in vivo.

Assays for determining the biological activities and binding properties of the wildtype CHIPS protein and variants thereof are well known in the art (see Examples).

Of course, it will be appreciated by persons skilled in the art that the polypeptide of the first aspect of the invention may exhibit the biological activity at a level which is less than, the same as or greater than the level exhibited by the wildtype CHIPS protein. Preferably, the polypeptide of the invention exhibits the biological activity at a level of at least 10% of the level exhibited by the wildtype CHIPS protein, for example at least 20%, 30%, 40%, 50%, 60%, 70%, 80%, 90%, 100% or more. More preferably, the polypeptide of the invention exhibits the biological activity at the same level or more compared to the biological activity exhibited by the wildtype CHIPS protein. Most preferably, the polypeptide of the invention exhibits the biological activity at a greater level (i.e. is more active) than the wildtype CHIPS protein. For example, the polypeptide of the invention may exhibit the biological activity at a level of at least 110% of the level exhibited by the wildtype CHIPS protein, for example at least 120%, 130%, 140%, 150%, 160%, 170%, 180%, 190%, 200%, 250%, 300%, 500% or more.

In a further embodiment, the polypeptide of the invention has a specific binding activity for the C5aR and/or FRP which is equal to or greater than the corresponding activity exhibited by the wildtype CHIPS protein.

Thus, the polypeptide of the invention exhibits only biological activities of the CHIPS protein, i.e. the activity of the polypeptide is selective. For example, the polypeptide of the invention may inhibit the chemotaxis and/or activation of neutrophils induced by the complement component C5a and/or the by the N-formyl-peptide, fMLP selectively. By 'selective' we mean that the polypeptide inhibits said biological activity to a greater extent than it modulates the activity of other proteins in the cells. Thus, the polypeptide preferably inhibits only the biological activity of the wildtype CHIPS protein, although it will be appreciated that the expression and activity of other proteins within cells may change as a downstream consequence of a selective inhibition. Thus, we exclude agents which have a non-specific effect on cellular processes.

In a still further embodiment of the first aspect of the invention, the polypeptide is a variant of the polypeptide according to SEQ ID NO: 2 wherein one or more surface epitopes is modified. Such modifications can either be direct (i.e. modification of an amino acid within the epitope itself) or indirect (i.e. modification of an amino acid which is not in an epitope but, when modified, leads in the modification of an amino acid within the epitope or the structure of such an epitope).

By "surface epitope" we mean a conformation of exposed amino acid residues at the surface of the wildtype CHIPS protein which is recognised by anti-CHIPS antibodies produced in response to a challenge with the CHIPS antigen and/or by antibodies produced in response to a challenge with *S. aureus*.

In a particular embodiment of the first aspect of the invention, the polypeptide is less immunogenic in humans than the polypeptide according to SEQ ID NO: 1.

By "immunogenic" we mean that the ability of the polypeptide to induce an immune response (i.e. production of anti-polypeptide antibodies) in the host organism. Preferably, the polypeptide is less immunogenic than the polypeptide according to SEQ ID NO: 1 in humans.

Immunogenicity may be determined by methods well known in the art. For example, rabbits or other animal species (such as mice, rats, guinea pigs, dogs, etc) may be immunised with the polypeptide of the invention and the formation of immuno-complexes determined. Ideally, immune responses are studied in several different species, in order to exclude species-specific effects. One suitable method for assessing likely immunogenicity in humans involves purifying human anti-CHIPS IgG and determining the affinity of the variant polypeptide for such antibodies, e.g. using ELISA (see Examples below).

In a further embodiment, the polypeptide of the invention is capable of inhibiting C5a-induced activation of neutrophils. Such inhibition may be partial or complete. Thus, the C5a-induced activation of neutrophils may be inhibited in response to the polypeptide of the invention by at least 10%, for example at least 20%, 30%, 40%, 50%, 60%, 70%, 80%, 90%, 95% and preferably by 100% compared to activation in the absence of the polypeptide.

In a preferred embodiment of the first aspect of the invention, the polypeptide exhibits one of more (for example, all) of the following properties:
(a) An $IC_{50}$ for the inhibition of neutrophil migration (chemotaxis) of less than 1 nM, preferably 0.5 nM or less (see Examples); and/or
(b) A serum IgG titre of 2% or less of that for wildtype CHIPS (see Examples); and/or
(c) An $IC_{50}$ for the blockade of C5aR less than four times that of wildtype CHIPS (see Examples); and/or
(d) A melting temperature, $T_m$, of greater than 50° C., preferably greater than 60° C. (see Examples).

Thus, in one embodiment, the polypeptide comprises the amino acid sequence of SEQ ID NO: 2. For example, the polypeptide may consist of the amino acid sequence of SEQ ID NO: 2 with an additional N-terminal methionine.

In a further embodiment, the polypeptide consists of the amino acid sequence according to SEQ ID NO: 2.

Polypeptides of the invention may be made by methods well known to persons skilled in the art (for example, see Sambrook & Russell, 2000, *Molecular Cloning, A Laboratory Manual*, Third Edition, Cold Spring Harbor, N.Y., which is incorporated herein by reference).

In brief, expression vectors may be constructed comprising a nucleic acid molecule which is capable, in an appropriate host, of expressing the polypeptide encoded by the nucleic acid molecule.

A variety of methods have been developed to operably link nucleic acid molecules, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, e.g. generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease site are commercially available from a number of sources including International Biotechnologies Inc., New Haven, Conn., USA.

A desirable way to modify the DNA encoding the polypeptide of the invention is to use PCR. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide may be used in accordance with known techniques, appropriately modified in view of the teachings contained herein, to construct an expression vector, which is then used to transform an appropriate host cell for the expression and production of the compound of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker (which is incorporated herein by reference).

The DNA (or in the case or retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector of the invention are then cultured for a sufficient time and under appropriate conditions known to those skilled in the art in view of the teachings disclosed herein to permit the expression of the polypeptide, which can then be recovered.

Many expression systems are known, including bacteria (for example, *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA. Particularly preferred prokaryotic vector plasmids include the pET system (Novagene), pRSET and pHIP (Invitrogen, California, USA).

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CRL 1658, 293 cells which are human embryonic kidney cells, and NS0 cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook at al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cells, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5 PEB using 6250V per cm at 25 µFD.

Methods for transformation of yeast by electroporation are disclosed in Becker & Guarente (1990) *Methods Enzymol.* 194, 182.

Successfully transformed cells, i.e. cells that contain a DNA construct of the present invention, can be identified by well-known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity.

Samples of cells suspected of being transformed are harvested and assayed for the protein using suitable antibodies.

The host cell may be a host cell within a non-human animal body. Thus, transgenic non-human animals which express a compound according to the first aspect of the invention (or a binding moiety thereof) by virtue of the presence of the transgene are included. Preferably, the transgenic non-human animal is a rodent such as a mouse. Transgenic non-human animals can be made using methods well known in the art.

Methods of cultivating host cells and isolating recombinant proteins are well known in the art. It will be appreciated that, depending on the host cell, the compounds of the invention (or binding moieties thereof) produced may differ. For example, certain host cells, such as yeast or bacterial cells, either do not have, or have different, post-translational modification systems which may result in the production of forms of compounds of the invention (or binding moieties thereof) which may be post-translationally modified in a different way.

It is preferred that compounds of the invention (or binding moieties thereof) are produced in a eukaryotic system, such as a mammalian cell.

According to a less preferred embodiment, the compounds of the invention (or binding moieties thereof) can be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

Thus, a second aspect of the invention provides a nucleic acid molecule encoding a polypeptide according to the first aspect of the invention. In one embodiment, the nucleic acid molecule is a DNA molecule. Advantageously, the nucleic acid molecule further comprises a signal peptide recognisable by the host cell in which the polypeptide of the invention is expressed.

A third aspect of the invention provides a vector comprising a nucleic acid molecule according to the second aspect of the invention. In one embodiment, the vector is an expression vector (such as any vector from the pET-system, pRSET or pHIP).

A fourth aspect of the invention provides a host cell comprising a nucleic acid molecule according to the second aspect of the invention or a vector according to the third aspect of the invention.

In one embodiment, the host cell is an *E. coli* cell.

A fifth aspect of the invention provides a method for producing a polypeptide according to the first aspect of the invention comprising culturing a population of host cells comprising a nucleic acid molecule according to the second aspect of the invention or a vector according to the third aspect of the invention under conditions in which the polypeptide is expressed, and isolating the polypeptide therefrom. By "isolating" the expressed polypeptide we include removing some or all impurities from the culture medium, such as cell debris. In one embodiment, the polypeptide is substantially pure.

It will be appreciated by persons skilled in the art that the polypeptides of the invention are preferably provided in the form of a pharmaceutical composition comprising the compound and a pharmaceutically acceptable carrier. Thus, a sixth aspect of the invention provides a pharmacological composition comprising a polypeptide according to the first aspect of the invention.

By "pharmaceutically acceptable" is included that the formulation is sterile and pyrogen free. Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used. Thus, "pharmaceutically acceptable carrier" and "pharmaceutically acceptable excipient" includes any compound(s) used in forming a part of the formulation that is intended to act merely as a carrier, i.e., not intended to have biological activity itself. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The polypeptides of the invention can be formulated at various concentrations, depending on the efficacy/toxicity of the compound being used. Preferably, the formulation comprises the agent of the invention at a concentration of between 0.1 μM and 1 mM, more preferably between 1 μM and 100 μM, between 5 μM and 50 μM, between 10 μM and 50 μM, between 20 μM and 40 μM and most preferably about 30 μM. For in vitro applications, formulations may comprise a lower concentration of a compound of the invention, for example between 0.0025 μM and 1 μM.

It will be appreciated by persons skilled in the art that the medicaments and agents (i.e. polypeptides) will generally be administered in admixture with a suitable pharmaceutical excipient diluent or carrier selected with regard to the intended route of administration and standard pharmaceutical practice (for example, see *Remington: The Science and Practice of Pharmacy*, 19$^{th}$ edition, 1995, Ed. Alfonso Gennaro, Mack Publishing Company, Pennsylvania, USA, which is incorporated herein by reference).

For example, the medicaments and agents can be administered orally, buccally or sublingually in the form of tablets, capsules, ovules, elixirs, solutions or suspensions, which may contain flavouring or colouring agents, for immediate-, delayed- or controlled-release applications. The medicaments and agents may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The medicaments and agents of the invention can also be administered parenterally, for example, intravenously, intra-articularly, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the medicaments and agents will usually be from 1 to 1000 mg per adult (i.e. from about 0.015 to 15 mg/kg), administered in single or divided doses.

The medicaments and agents can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the medicaments and agents can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For application topically to the skin, the medicaments and agents can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Where the medicament or agent is a polypeptide, it may be preferable to use a sustained-release drug delivery system, such as a microsphere. These are designed specifically to reduce the frequency of injections. An example of such a system is Nutropin Depot™ which encapsulates recombinant human growth hormone (rhGH) in biodegradable microspheres that, once injected, release rhGH slowly over a sustained period.

Sustained-release immunoglobulin compositions also include liposomally entrapped immunoglobulin. Liposomes containing the immunoglobulin are prepared by methods known per se. See, for example Epstein et al., *Proc. Natl. Acad. Sci. USA* 82: 3688-92 (1985); Hwang et al., *Proc. Natl. Acad. Sci. USA* 77: 4030-4 (1980); U.S. Pat. Nos. 4,485,045; 4,544,545; 6,139,869; and 6,027,726. Ordinarily, the liposomes are of the small (about 200 to about 800 Angstroms), unilamellar type in which the lipid content is greater than about 30 mole percent (mol. %) cholesterol; the selected proportion being adjusted for the optimal immunoglobulin therapy.

Alternatively, polypeptide medicaments and agents can be administered by a surgically implanted device that releases the drug directly to the required site.

Electroporation therapy (EPT) systems can also be employed for the administration of proteins and polypeptides. A device which delivers a pulsed electric field to cells increases the permeability of the cell membranes to the drug, resulting in a significant enhancement of intracellular drug delivery.

Proteins and polypeptides can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of protein and polypeptide delivery is the thermo-sensitive ReGel® injectable. Below body temperature, ReGel® is an injectable liquid while at body temperature it immediately forms a gel reservoir that slowly erodes and dissolves into known, safe, biodegradable polymers. The active drug is delivered over time as the biopolymers dissolve.

Protein and polypeptide pharmaceuticals can also be delivered orally. One such system employs a natural process for oral uptake of vitamin B12 in the body to co-deliver proteins and polypeptides. By riding the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the drug portion of the complex.

Thus, one aspect of the invention provides a polypeptide according to the first aspect of the invention for use in medicine.

A further aspect of the invention provides a polypeptide according to the first aspect of the invention for use in inhibiting a biological activity of complement 5a (C5a) and/or the N-formyl-peptide, fMLP.

A related aspect of the invention provides the use of a polypeptide according to the first aspect of the invention in the preparation of a medicament for inhibiting a biological activity of complement 5a (C5a) and/or the N-formyl-peptide, fMLP.

The anaphylatoxin C5a mediates a wide array of inflammatory responses. Acting on the C5aR it plays an important role in the activation and recruitment of phagocytes and is crucial for an effective clearance of invading microorganisms. In recent years it has become clear that C5a also plays an important role in destructive inflammatory processes like tissue damage and severe inflammatory syndromes that lead to organ failure. Additionally, C5a has also been associated with several other biologic processes that affect normal organ development, early differentiation of various cell lineages, and protection of cells from apoptotic death (see Table 1).

TABLE 1

C5a-associated biologic processes

Activation of MAPK
Angiogenesis
Apoptosis
Arachidonic acid metabolism
Astrocyte activation
Basophil activation
Blood coagulation
Bone remodeling
Bone resorption
Catecholamine biosynthesis
Cell adhesion
Cell cycle
Cell differentiation
Cell growth
Cell invasion
Cell migration
Cyclooxygenase pathway
Eicosanoid biosynthesis
Endocytosis
Endothelial cell activation
Eosinophil chemotaxis
Exocytosis
Fertilization
Fibrinolysis
Glucose metabolism
Glycolysis
Hexose transport
Hyperphosphorylation
Lipid metabolism
Lipoxygenase pathway
Lymphocyte activation
Lymphocyte chemotaxis
Lymphocyte proliferation
Macrophage activation
Macrophage chemotaxis
Macrophage differentiation
Mast cell activation
Microtubule polymerization
Monocyte activation
Myelination
Neutrophil activation
Neutrophil chemotaxis
Phospholipase C activation
Phospholipid metabolism
Platelet activation
Protein kinase C activation
Regulation of actin polymerization
Respiratory burst
Smooth muscle contraction
Spermatogenesis
Superoxide release
T-cell proliferation
Vasoconstriction
Vasodilation
Viral entry
Wound healing The human formyl-peptide-receptor (FPR) and its variants FPRL-1 (FPR-like 1) and FPRL-2 (FPR-like 2) belong to the seven transmembrane domain Gi-protein-coupled receptors. Both receptors are present in high levels on neutrophils and monocytes. The FPR is defined as the high affinity formyl-peptide receptor and FPRL-1 as the low affinity receptor based on its activation only by high concentrations of fMLP. Since the only source of formyl peptides in nature is bacterial and mitochondrial protein synthesis, it is thought that these receptors act as mediators for the recruitment of phagocytes towards a site of bacterial invasion or tissue damage. This is supported by the observation that FPR knockout mice are more susceptible to infection with *Listeria monocytogenes*. Also, dysfunctional FPR alleles are associated with localised juvenile periodontitis.

Over the last years a large number of non-formylated peptide ligands for these receptors have been identified (see Table 2) These ligands originate from different sources including random peptide libraries, endogenous sources and pathogens. Some of them are associated with human diseases including Alzheimer's disease, amyloidosis and prion disease. Therefore, formyl-peptide receptors are a target in the treatment of different inflammatory processes.

TABLE 2

FPR and FPRL-1 agonists and antagonists

| | Origin | Receptor | $EC_{50}$ or $IC_{50}$ |
|---|---|---|---|
| Agonists | | | |
| Bacterial peptides | | | |
| fMLF and analogues | Bacteria and mitochondria | FPR | 0.1-1 nM |
| | | FPRL-1 | 1 μM |
| | | mFPR1 | 1 μM |
| | | mFPR2 | 10 μM |
| Hp(2-20) | *Helicobacter pylori* | FPRL1 | 0.3 μM |
| | | FPRL-2 | 10 μM |
| HIV-1 envelope peptides | | | |
| T20 (DP178) | HIV-1$_{LAV}$gp41 (aa643-678) | FPR | 0.5 μM |
| | | mFPR1 | 1 μM |
| | | mFPR-2 | 0.5 μM |
| T21 | HIV-1$_{LAV}$gp41 (aa558-595) | FPR | 0.1 μM |
| | | FPRL-1 | 50 nM |
| N36 | HIV-1$_{LAV}$gp41 (aa546-581) | FPRL-1 | 12.5 μM |
| F peptide | HIV-1$_{Bru}$gp120 (aa414-434) | FPRL1 | 10 μM |
| V3 peptide | HIV-1$_{MN}$gp120 (V3 loop) | FPRL-1 | 2 μM |
| Peptide library derived agonists | | | |
| W-peptide (WKYMVm) | Random peptide library | FPR | 1 nM |
| | | FPRL-1 | 1 pM |
| | | FPRL-2 | 5 nM |
| | | mFPR-1 | 50 nM |
| | | mFPR-2 | 1 nM |
| MMK-1 | Random peptide library | FPRL-1 | 0.5 nM |
| | | mFPR2 | 0.5 nM |
| WKYMVM | Random peptide | FPRL-1 | 2 nM |
| | | FPRL-2 | 80 nM |
| Host-derived agonists | | | |
| MHC binding peptide | NADH dehydrogenase subunit I | FPRL-1 | 0.5 nM |
| LL-37 | hCAP18$_{1-37}$ | FPRL-1 | 1.0 μM |
| Ac1-26 | Annexin(aa1-26) | FPR | 5 μM |
| Ac9-25 | Annexin(aa9-25) | FPR | 10 nM |
| D2D388-274 | uPAR(aa88-274) | FRPL1 | 5 pM |
| LXA4 | Lipid metabolite | FPRL1 | 1.0 nM |
| SAA | Acute phase protein | FPRL-1 | 0.1 μM |
| | | mFPR-2 | 1 μM |
| Aβ$_2$42 | APP(aa1-42) | FPRL-1 | 1 μM |
| | | mFPR-2 | 2 μM |
| PrP$_{106-1262}$ | Prion(aa106-126) | FPRL-1 | 25 μM |
| Antagonists | | | |
| Boc-FLFLF | Synthetic | FPR | 2 μM |
| Cylosporin H | Fungus | FPR | 0.5 μM |
| DCA | Bile acid | FPR | 100 μM |
| CDCA | Bile acid | FPR | 175 μM |
| | | FPRL-1 | 300 μM |
| Spinorphin | Cerebrospinal fluid | FPR | 50 μM |

Thus, the polypeptide is for use as an antagonist at the C5aR. Conveniently, the polypeptide is capable of binding directly to this receptor.

In one embodiment, the polypeptide is for inhibiting, in whole or in part, the function of C5a receptors.

In a further embodiment, the C5a receptors are located on neutrophils, monocytes and/or endothelial cells.

Thus, the polypeptide may be for inhibiting the activation of neutrophils induced by complement 5a (C5a).

In one embodiment, the polypeptide is for treating inflammation, for example acute or chronic inflammatory reactions.

The terms "treating", and "treatment", and the like are used herein to generally mean obtaining a desired pharmacological and physiological effect. Further, it refers to any process, action, application, therapy, or the like, wherein a mammal, including a human being, is subject to medical aid with the object of improving the mammal's condition, directly or indirectly. Thus, treatment includes both therapeutic and prophylactic use.

In further embodiments, the polypeptide is for use in treating a disease or condition selected from the group consisting of acute reactive arthritis, acute transplant rejection, adult respiratory distress syndrome (ARDS), alcoholic hepatitis, allotransplantation, Alzheimer's disease, arteriosclerosis, arthus reaction, asthma, atherosclerosis, atopic dermatitis, bacterial meningitis, bronchogenic carcinoma, bullos pemphigoid, burns, cardiopulmonary bypass, cardiovascular diseases, chronic bronchitis, chronic lymph leukaemia, chronic obstructive pulmonary disease (COPD), contact dermatitis, Crohn's disease, cutaneous T-cell lymphoma, cystic fibrosis, dermatoses, diseases of the central nervous system, endometriosis, experimental allergic encephalomyelitis (EAE), experimental allergic neuritis (EAN), frost bite, gastric carcinoma, gastrointestinal diseases, genitourinary diseases, gout, *Heliobacter pylori* gastritis, haemodialysis, hereditary angioedema, hypersensitive pneumonia, idiopathic pulmonary fibrosis, immune-complex (IC)-induced vasculitis, ischaemic shock, ischaemic reperfusion episodes, ischaemic reperfusion injury, joint diseases, (large) vessel surgery, metal fume fever, multiple sclerosis, multiple system organ failure, myasthenia gravis, myocardial infarction, pancreatitis, peritonitis, pleural emphesema, post-cardiopulmonary bypass (CPB) inflammation, psoriasis, repetitive strain injury (RSI), respiratory diseases, rheumatoid arthritis, sepsis, septic shock, sinusitis, skin diseases, stroke, systemic lupus erythematosis (SLE), transplantation, (traumatic) brain injury, ulcerative colitis, urinary tract infection, vascular leak syndrome, vasculitis and xenotransplantation.

In one embodiment, the polypeptide is for use in treating reperfusion injury. For example, the reperfusion injury may be associated with acute myocardial infarction (AMI), a coronary artery bypass graft (CABG), stroke and/or organ transplantation.

In a further embodiment, the polypeptide is for use in treating acute respiratory distress syndrome (ARDS).

Thus, the invention further provides a method of treatment of a subject in need of treatment with an inhibitor of a biological activity of complement 5a (C5a) and/or the N-formyl-peptide, fMLP, the method comprising administering to the subject a polypeptide according to the first aspect of the invention or a pharmaceutical composition according to the sixth aspect of the invention.

Persons skilled in the art will appreciate that the subject is human.

The polypeptide or pharmaceutical composition of the invention is administered to the patient in an effective amount. A 'therapeutically effective amount', or 'effective amount', or 'therapeutically effective', as used herein, refers to that amount which provides inhibition of a biological activity of complement 5a (C5a) and/or the N-formyl-peptide, fMLP. This is a predetermined quantity of active material calculated to produce the desired therapeutic effect. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Thus, in one embodiment, the method comprises administering to the individual an amount of the compound sufficient to act as an antagonist at C5aR and/or FPR.

It will be appreciated by persons skilled in the art that such an effective amount of the compound or formulation thereof may be delivered as a single bolus dose (i.e. acute administration) or, more preferably, as a series of doses over time (i.e. chronic administration).

Variant CHIPS proteins according to the present invention may be produced by directed evolution technology, such as the Fragment-Induced Nucleotide Diversity (FIND®) methodology developed by Alligator Bioscience AB. The FIND® methodology is described in detail in WO 98/58080, WO 02/48351 and WO 03/97834.

Thus, a further aspect of the invention provides a method for producing a polypeptide according to the first aspect of the invention, the method comprising the following steps:

(a) providing one or more parent polynucleotide molecules encoding the polypeptide according to SEQ ID NO: 2 or variant(s) thereof;

(b) digesting the one or more parent polynucleotide molecules with a nuclease (e.g. an exonuclease) to generate polynucleotide fragments;

(c) contacting said polynucleotide fragments generated in step (b) with each other; and (d) amplifying the fragments that anneal to each other to generate at least one polynucleotide sequence encoding a variant CHIPS polypeptide having an altered amino acid sequence as compared to those encoded by the one or more parent polynucleotide molecules.

It will be appreciated by skilled persons that the parent polynucleotides provided in step (a) may be double-stranded or single-stranded. Preferably, however, parent polynucleotide molecules in step (a) are single-stranded.

In one embodiment, step (d) comprises adding oligonucleotides of predefined variability in order to control the degree of variability introduced into defined regions of the parent polynucleotides.

In a further embodiment, the method additionally comprises step (e) of expressing the at least one polynucleotide sequence produced in step (d) and screening the resultant polypeptide for a biological activity of the wildtype CHIPS protein, such as the ability to inhibit C5a-induced activation of neutrophils and/or fMLP-induced activation of neutrophils.

Step (e) may also comprise testing the resultant polypeptide for the ability to bind to C5aR and/or FPR. Such binding properties may be assessed using techniques well known in the art, for example affinity chromatography and phage display.

More preferably, the method further comprises step (f) of screening the resultant polypeptide for reduced immunogenicity relative to the polypeptide according to SEQ ID NO: 2.

For example, step (e) may comprise one or more of the following screening procedures:

(i) Assay for ability of variant CHIPS polypeptides to bind to C5aR.

For example, phage selection may be used to screen for binding of variant polypeptides to a peptide corresponding to the N-terminal part of the C5aR. After the first positive selection, eluted phages may be amplified and a subsequent positive selection performed. In the second positive selection, human anti-CHIPS antibodies may be added to absorb unwanted CHIPS molecules with retained binding to anti-CHIPS antibodies; this can increase the possibility of identifying clones which are less immunogenic.

Directly after the second positive selection, the eluted phages may be incubated with human anti-CHIPS antibodies coated to magnetic beads. Pools of eluates are then collected, as follows; (1) phages that did not bind the antibodies, (2) phages eluted after washing steps, (3) phages eluted with low or (4) high concentration of CHIPS. Clones from pools (1) and (2) may be preferentially selected for further screening.

The genes from the selected pool of mutants may be cloned into the pRSET vector and protein produced in HT format.
(ii) Assay for the concentration of each variant CHIPS polypeptide by expression ELISA.
(iii) Assay for the binding activity of the variant CHIPS polypeptides to anti-CHIPS antibodies, for example by inhibition ELISA and/or human anti-CHIPS antibody ELISA.
(iv) Selected variant CHIPS polypeptides may also be re-expressed and analysed in expression ELISA and peptide ELISA.

Further details of exemplary screening procedures are provided in the Examples (see below).

It will be appreciated that screening assays which are capable of high throughput operation will be particularly preferred. Examples may include cell-based assays and protein-protein binding assays. An SPA-based (Scintillation Proximity Assay; Amersham International) system may be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

Alternative methods of detecting binding of a polypeptide to macromolecules, for example DNA, RNA, proteins and phospholipids, include a surface plasmon resonance assay, for example as described in Plant et al (1995) *Analyt Biochem* 226(2), 342-348 (which is incorporated herein by reference). Methods may make use of a polypeptide that is labelled, for example with a radioactive or fluorescent label.

A further method of identifying a polypeptide that is capable of binding to a target macromolecule (such as C5aR or FPR) is one where the target macromolecule is exposed to the polypeptide and any binding of the polypeptide to the said macromolecule is detected and/or measured. The binding constant for the binding of the polypeptide to the macromolecule may be determined. Suitable methods for detecting and/or measuring (quantifying) the binding of a polypeptide to a macromolecule are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips or arrays have probes arranged in arrays; each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips or arrays are useful in a variety of screening techniques for obtaining information about either the probes or the target molecules. For example, a library of peptides can be used as probes to screen for drugs. The peptides can be exposed to a receptor, and those probes that bind to the receptor can be identified. See U.S. Pat. No. 5,874,219 issued 23 Feb. 1999 to Rava et al.

It will be understood that it will be desirable to identify polypeptides that may block C5aR and/or FPR in vivo. Thus it will be understood that reagents and conditions used in the method may be chosen such that the interactions between the said and the interacting polypeptide are substantially the same as between a said naturally occurring polypeptide and a naturally occurring interacting polypeptide in vivo.

Exemplary embodiments of the invention are described in the following non-limiting examples, with reference to the following figures:

FIG. 1—Frequency distribution of IgG anti-CHIPS titres in healthy human donors (n=168). The titre was defined as the log dilution that gives an absorbance of 0.300 after subtraction of background value. The mean titre was 3.62 with an SD of 0.72. The insert depicts the anti-CHIPS titres of the 6 subjects before study entry (mean of 3 values corrected for human pooled serum as reference in every ELISA).

Figure 2:
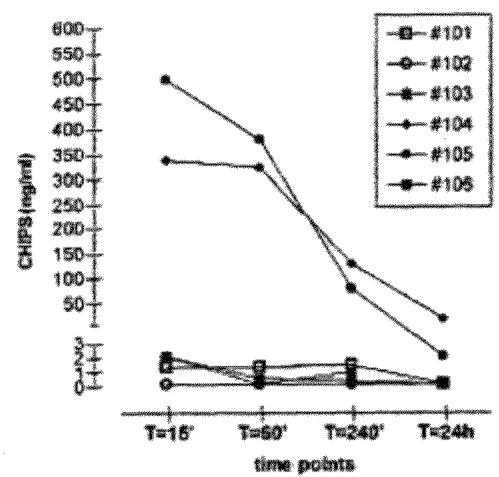

FIG. 2—Pharmaco dynamic of CHIPS detected in the sera of the volunteers. CHIPS was measured by a specific capture ELISA at the various time points after iv injection of CHIPS. Open symbols represent placebo and closed symbols CHIPS receiver.

Figure 3:
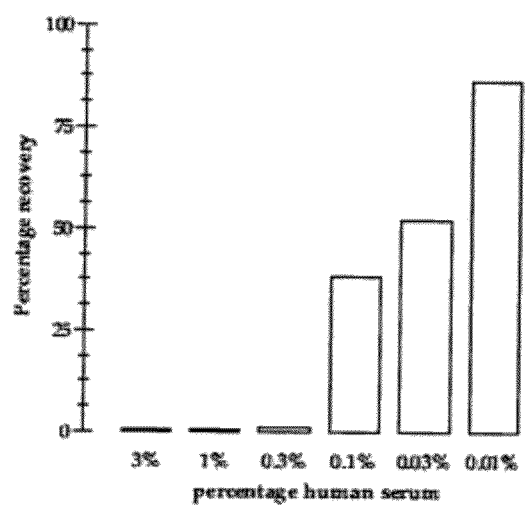
Figure 3:
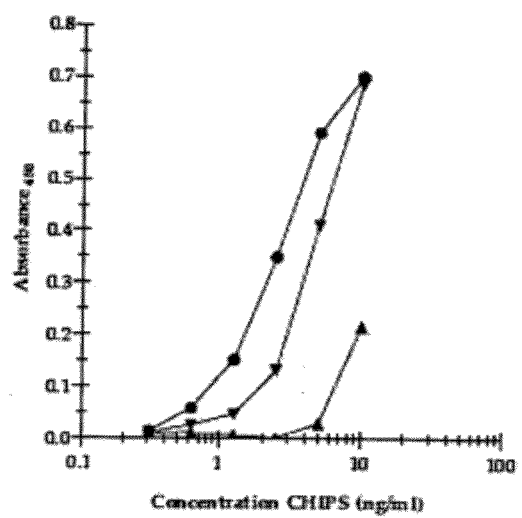

FIG. 3—Human anti-CHIPS IgG inhibits detection of CHIPS by capture ELISA. Recovery of 2.5 ng·mL$^{-1}$ CHIPS spiked into various concentrations pooled human serum and measured by capture ELISA (a). Depletion of IgG from human serum by passage over Protein-G-Sepharose eliminates the inhibitory effect on the CHIPS capture ELISA (b). Various concentrations CHIPS were incubated with buffer (●), 1% human serum (from a single donor; ▲), or 1% serum after Protein-G-Sepharose passage (▼). Data show one representative experiment.

Figure 4:
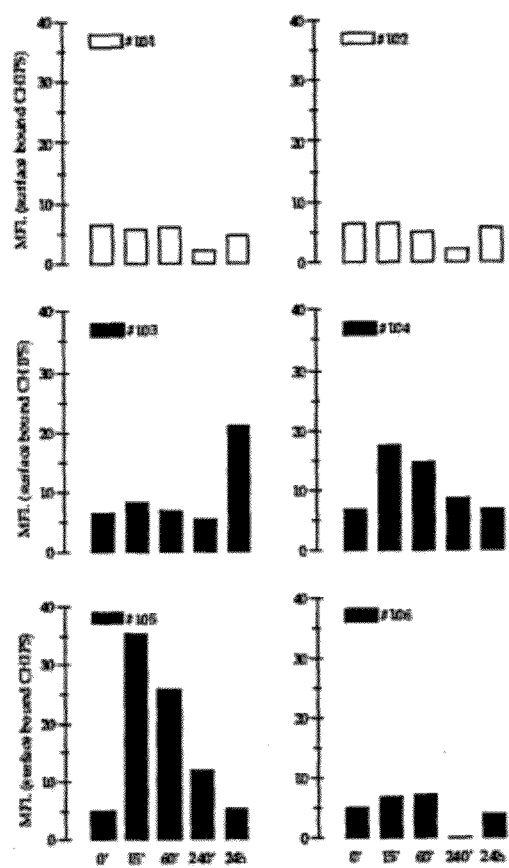

FIG. 4—CHIPS is recovered on the surface of peripheral blood neutrophils. At various time points after iv injection of CHIPS, the presence of CHIPS bound to the surface of neutrophils was detected with a rabbit-anti-CHIPS antibody. Individual subjects are shown; white bars represent placebo and black bars CHIPS receiver. Values are expressed as mean fluorescence (MFL) of gated neutrophils in EDTA whole blood samples at various time points (T=0, 15, 60, 240 min and after 24 hours). Background MFL value for the secondary FITC labelled conjugate was 6.

Figure 5A:
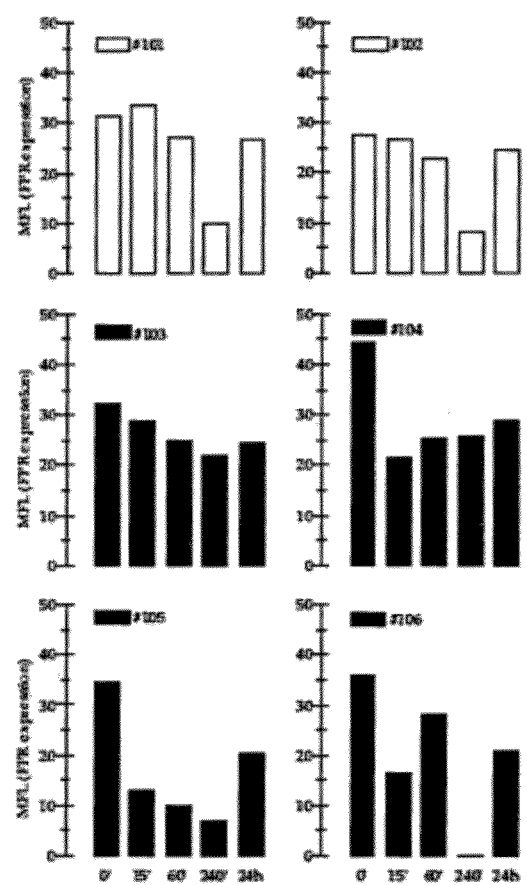
Figure 5B:
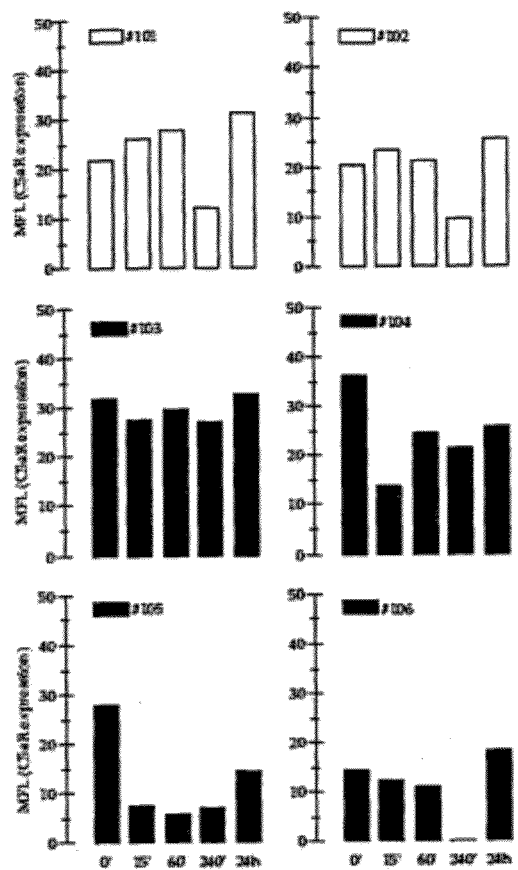

FIG. 5—Expression of FPR (a) and C5aR (b) on human peripheral blood neutrophils. At various time points after iv injection of CHIPS, the presence of FPR on the surface of neutrophils was detected with FITC-labelled fMLP and the presence of C5aR with a FITC labelled anti-CD88 mAb.

White bars represent placebo and black bars CHIPS receiver. Values are expressed as mean fluorescence (MFL) of gated neutrophils.

Figure 6:
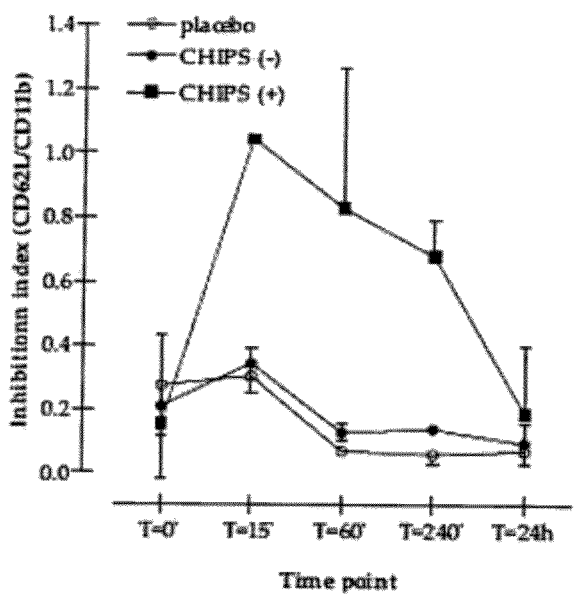

FIG. 6—Inhibition index of peripheral blood neutrophils after ex vivo whole blood fMLP stimulation. At various time points after iv injection of CHIPS, EDTA anticoagulated blood was incubated with buffer and fMLP for 30 min at 37° C. and analysed for the expression of both CD11b and CD62L. For every time point the expression of CD11b and CD62L was expressed relative to the buffer treated control sample (relative increase for CD11b and relative decrease for CD62L expression). These values were used to calculate the activation index for each subject at every time point (relative value for CD62L/relative value for CD11b). Data are expressed as the mean±SD of placebo (O), serum and neutrophil CHIPS negative (−) subjects (●) and CHIPS positive (+) subjects (■).

Figure 7:
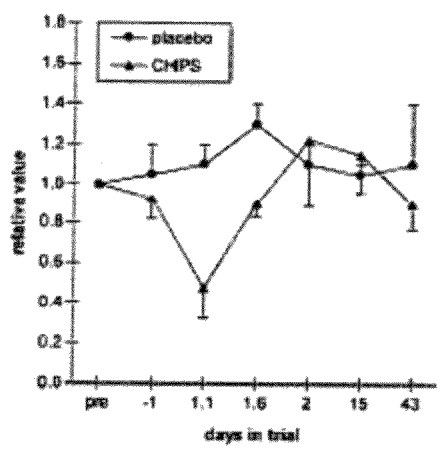
Figure 7:
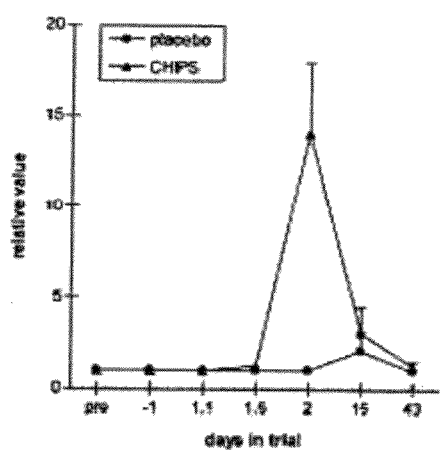

FIG. 7—Level of circulating peripheral white blood cells (a) and serum inflammation marker CRP (b). At various time points after iv injection of CHIPS, WBC counts and CRP measurements were performed. (1.1 and 1.6 indicate 1 day and 1 or 6 hours respectively). Data for WBC are expressed relative to the value at T=0 and data for CRP are expressed as mg·L$^{-1}$. Values are mean±SD for placebos (●) and CHIPS receivers (▲).

Figure 8:
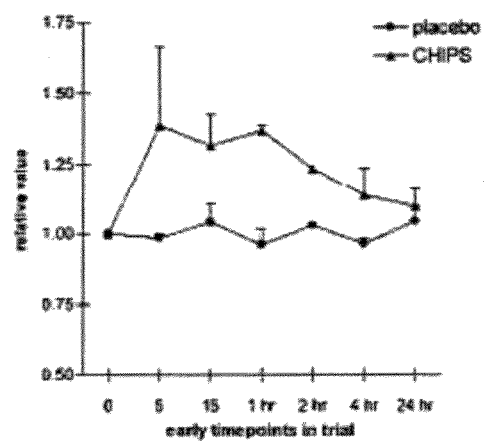
Figure 8:
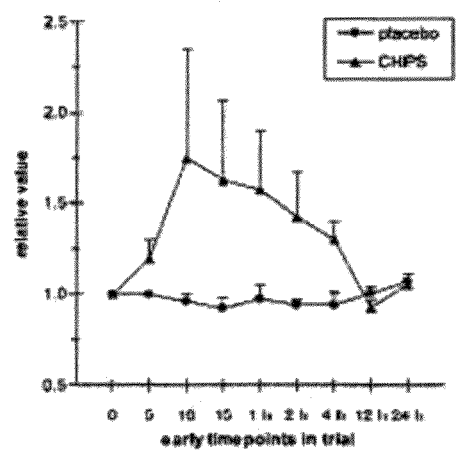

FIG. 8—Adverse effects of CHIPS as measured by levels of Circulating Immune Complexes (CIC; (a)) and mast cell marker tryptase (b). At various time points after iv injection of CHIPS, specific assays were performed for both markers. Data are expressed relative to the value at T=0 and shown as mean±SD for placebos (●) and CHIPS receivers (▲).

Figure 9A:
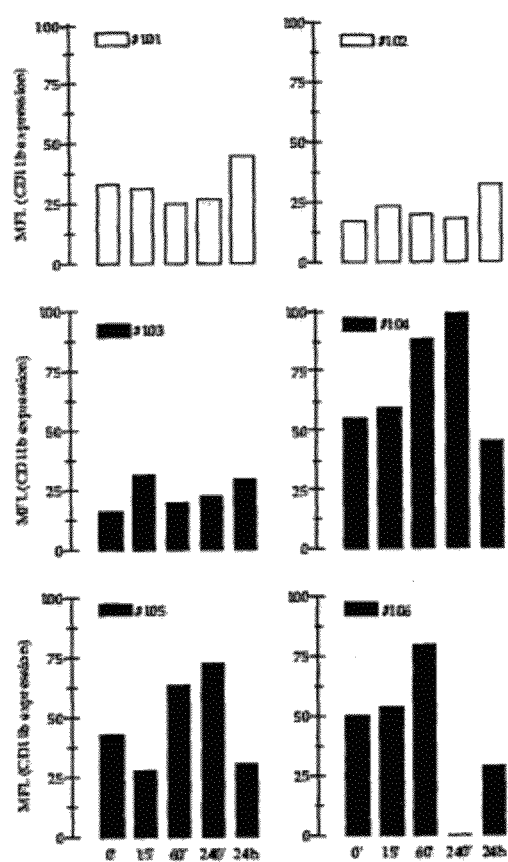
Figure 9B:
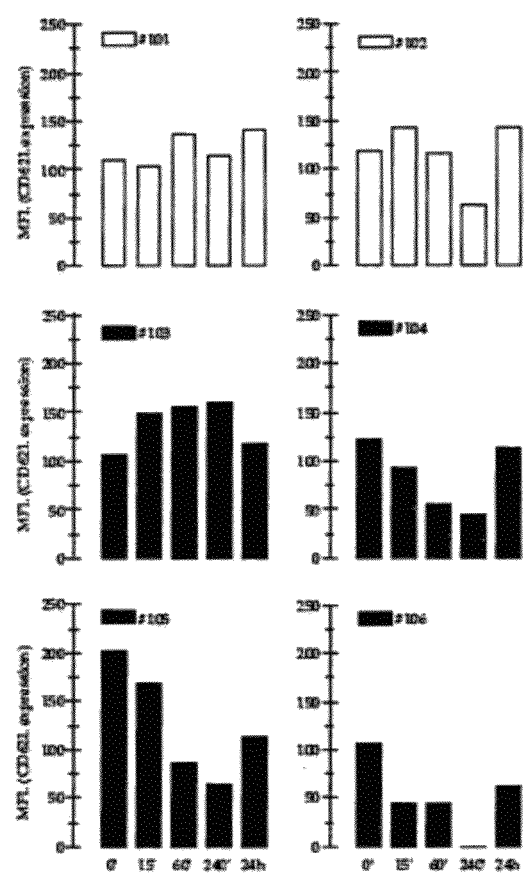

FIG. 9-E*xpression* index of CD 11b (a) and CD62L (b) on circulating peripheral blood neutrophils at various time points after iv injection of CHIPS. For each subject the expression of CD11b and CD62L was normalised for every time point relative to the initial expression level at T=0. These values were used to calculate the activation index for each subject at every time point (relative value for CD11b/relative value for CD62L).

Figure 10:
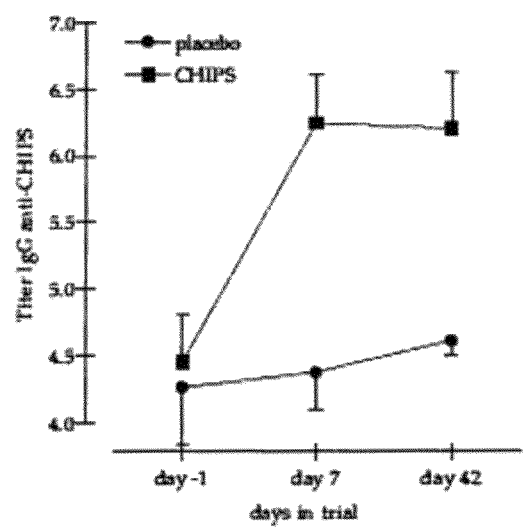

FIG. 10—Immunogenicity of CHIPS in healthy human subjects. Specific IgG titers towards CHIPS were determined in all subjects before trial start and 7 and 42 days after trial closing. Values are mean±SD for placebos (●) and CHIPS receivers (■).

Figure 11:
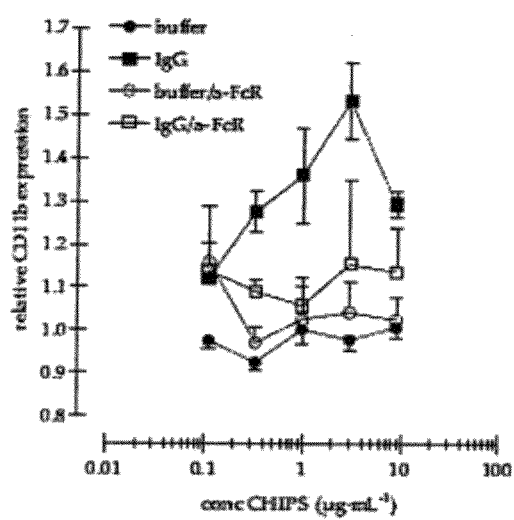

FIG. 11—Relative CD11b expression on neutrophils induced by CHIPS-IgG complexes in vitro. Isolated neutrophils from healthy volunteers were challenged with increasing concentration of CHIPS with (■) or without (●) 20 μg·mL$^{-1}$ affinity purified human α-CHIPS IgG. To address the role of FcγR, cells were pretreated with blocking mAb anti-FcRII (IV-3) and F(ab')2 anti-FcRIII (3G8), washed and used to stimulate with CHIPS in buffer (□) or anti-CHIPS IgG (○). After challenge cells were incubated on ice with fluorescent-labelled anti-CD11b mAb to determine the level of cell activation. Data are expressed relative to the CD11b expression of cells in buffer only (without CHIPS or IgG) and shown as mean±SEM (n≥3).

Figure 12:
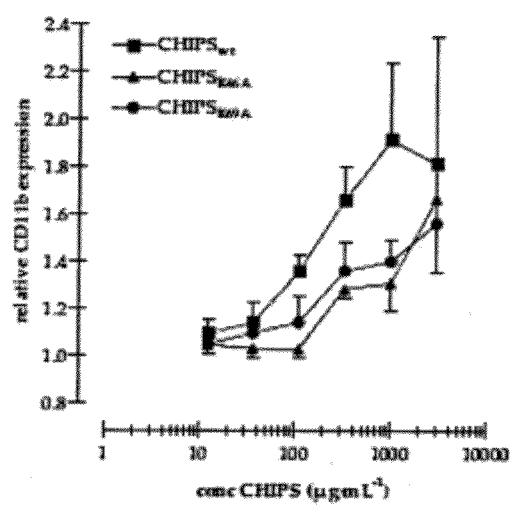

FIG. 12—Relative CD11b expression on whole blood neutrophils induced by CHIPS and alanine substitution mutants ex vivo. EDTA blood from healthy volunteers was challenged with increasing concentrations wild-type CHIPS(CHIPS$_{WT}$), alanine substitution mutant for arginine at position 46 (CHIPS$_{R46A}$) and mutant for lysine at position 69 (CHIPS$_{K69A}$). CD11b expression was determined with a specific mAb on ice and data expressed as relative to buffer only cells as means±SEM (n≥3).

Figure 13:
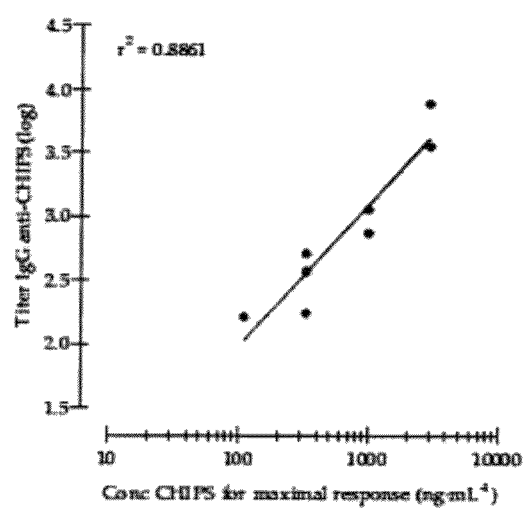

FIG. 13—Correlation between specific anti-CHIPS IgG titre and amount of CHIPS required for maximal stimulation of whole blood neutrophils ex vivo. EDTA blood from healthy volunteers was challenged with increasing concentrations CHIPS and CD11b expression measured as indication for cell activation. IgG anti-CHIPS titers were determined by ELISA and defined as the log serum dilution that gives an absorbance of 0.300. Regression analysis was performed using the formula: y=intercept+slope×ln(x).

Figure 14:
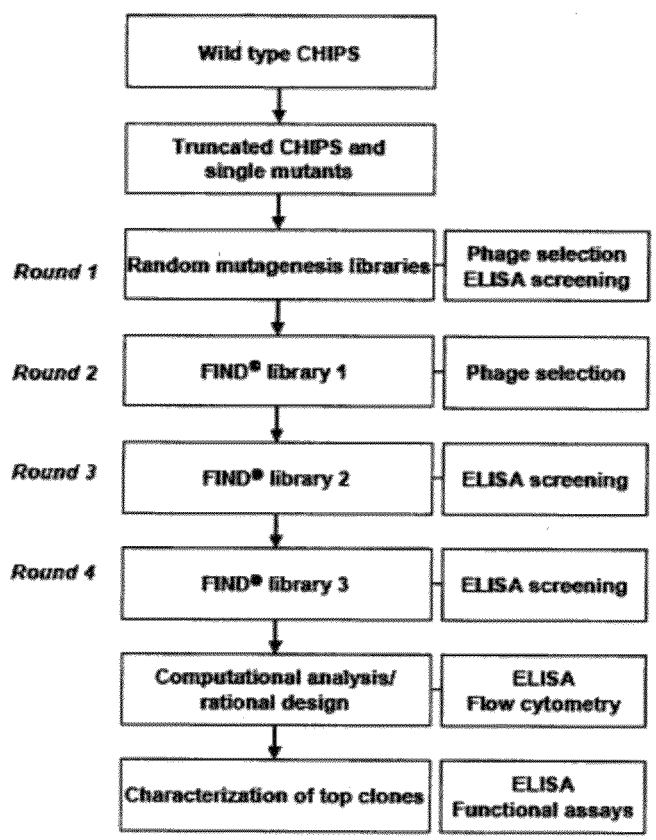

FIG. 14—Experimental strategy to decrease CHIPS interaction with human anti-CHIPS IgG, yet retaining C5aR blocking activity. An initial round of random mutagenesis and phage selection/ELISA screening was followed by three rounds of FIND® and phage selection/ELISA screening for decreased IgG binding and retained C5aR peptide binding. Then the structural distribution of the mutations in the improved clones was analyzed and new mutations were introduced by rational design. These clones were further analyzed for decreased IgG interaction and retained C5aR binding and inhibition.

Figure 15:
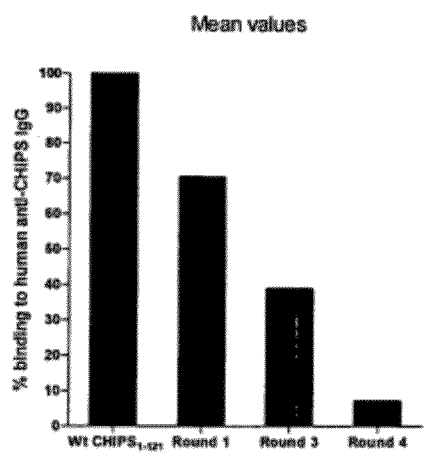
Figure 15:
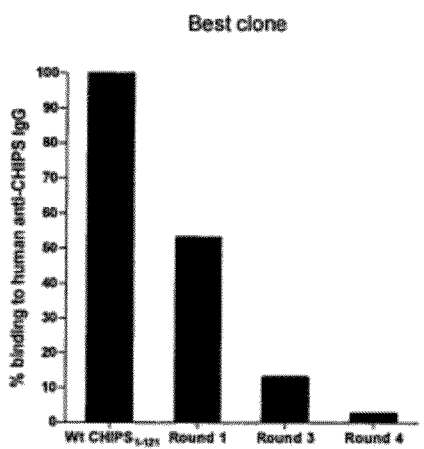
Figure 15:
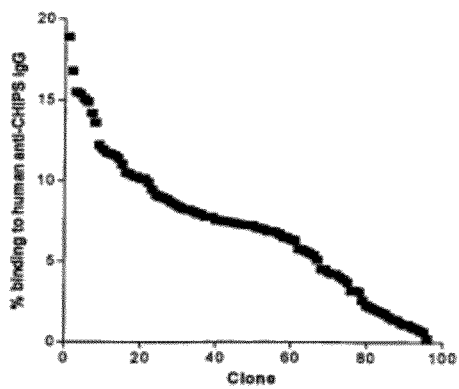

FIG. 15—Comparison of the mean values of clones (A) and best clones (B) from Round 1 (n=360), Round 3 (n=320) and Round 4 (n=96) to the wt CHIPS$_{1-121}$ as measured by % binding to human anti-CHIPS$_{31-113}$ IgG. The distribution of the 96 clones from Round 4 is shown in C.

Figure 16:
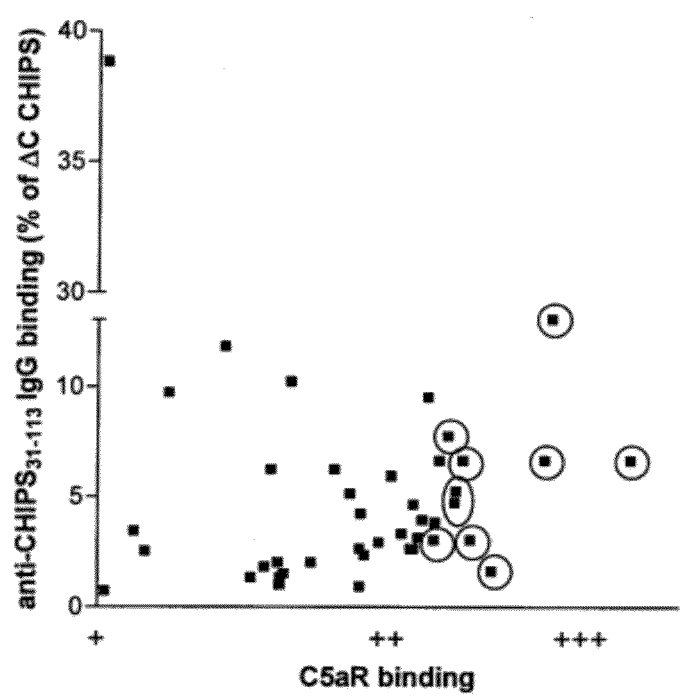

FIG. 16—Plot of the 42 best clones identified after the fourth round of diversification during the screening for decreased anti-CHIPS$_{31-113}$ IgG binding and retained C5aR binding. The 10 clones showing the highest binding to the human C5aR (in circles) were selected for further computational/rational design.

Figure 17:
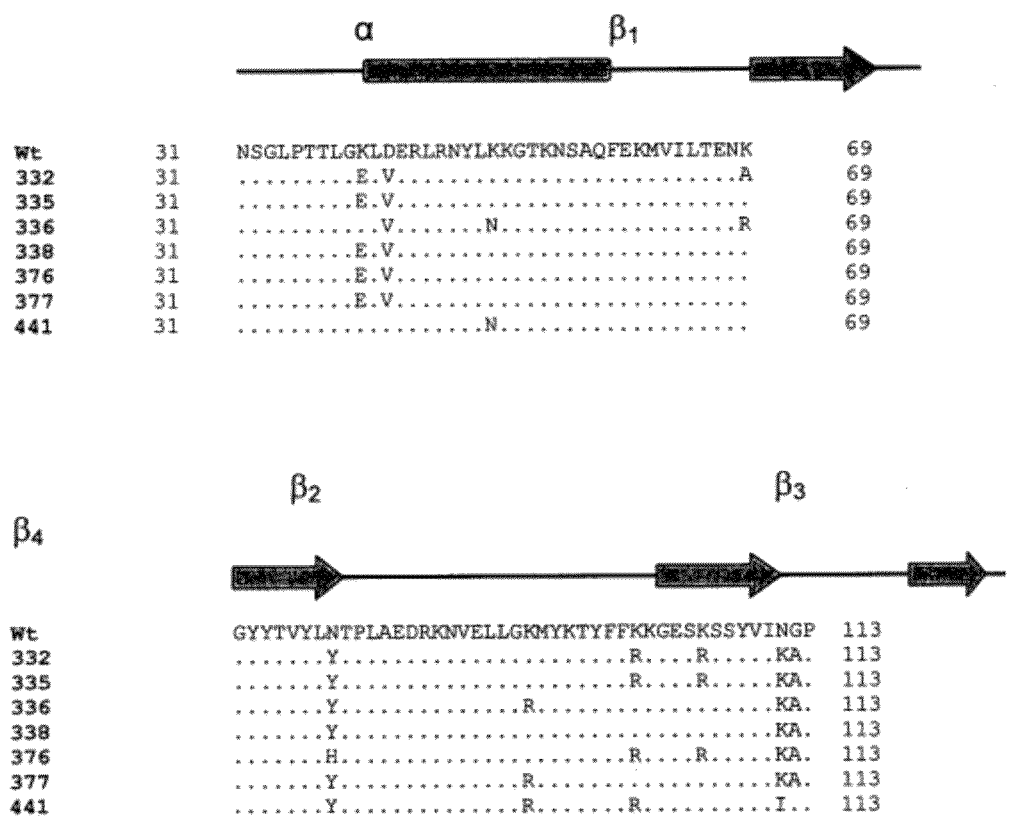

FIG. 17-S*equence* alignment of the top seven clones (SEQ ID NO.:7 (clone 332), SEQ ID NO.:8 (clone 335, SEQ ID NO.:9 (clone 336), SEQ ID NO.:10 (clone 338), SEQ ID NO.:2 (clone 376), SEQ ID NO.:11 (clone 377), SEQ ID NO.:12 (clone 441)) after random mutagenesis, FIND® and rational design. Positions K40, D42, N77, N111 and G112 are mutated in almost all clones in different combinations with mutations in positions K50, K69, K92, K100 and K105 (SEQ ID NO.: 5) compared to the wild type polypeptide (residues 31-113 (SEQ ID NO.:6)). The mutated positions are positioned in the α-helix, in the loop between the β$_1$ and β$_2$ sheets, in the loop between the β$_2$ and β$_3$ sheets, in β sheet 3, in the loop between the β$_3$ and β$_4$ sheets and in β sheet 4.

Figure 18:
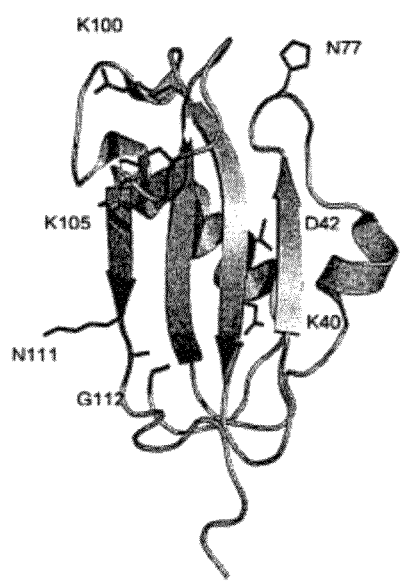

FIG. 18—Structural distribution of ADC-1004 mutations. Surface representation of ADC-1004 mutations. The known NMR structure of CHIPS$_{31-121}$ (PDB code: 1XEE) was used to show the structural distribution of the amino acid substitutions, K40E, D42V, N77H, K100R, K105R, N111K and G112A of ADC-1004. The figure was generated by the PyMol molecular graphics program (DeLano, 2002. The PyMol Molecular Graphics System. Delano Scientific, San Carlos).

Figure 19:
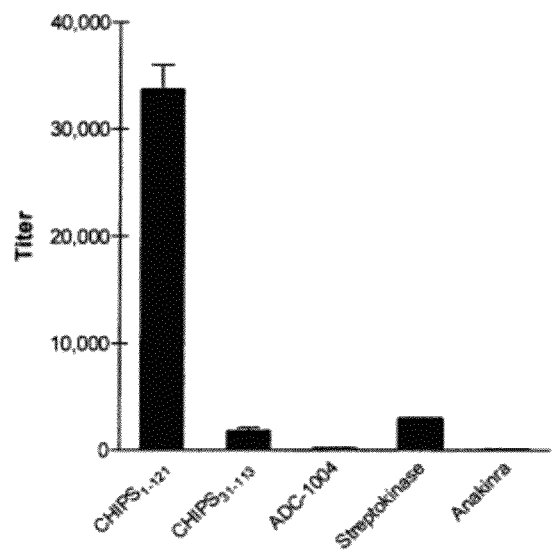
Figure 19:
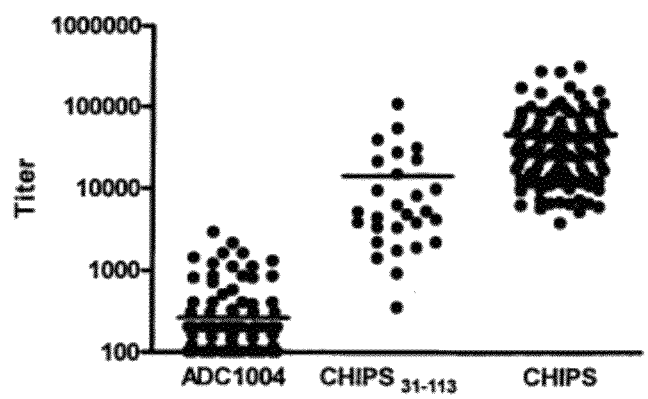

FIG. 19—ADC-1004 shows very low interaction with antibodies in human serum. The IgG binding in human serum of ADC-1004 was compared to the binding of CHIPS$_{1-121}$, CHIPS$_{31-113}$, Streptokinase and Anakinra in ELISA. Serial dilutions of human serum was added to a plate coated with CHIPS variants or PBS. The IgG titer of a pool of human serum is shown in (A) and the titer of 28 different individual human sera is shown in (B). The line represents the median value.

Figure 20:
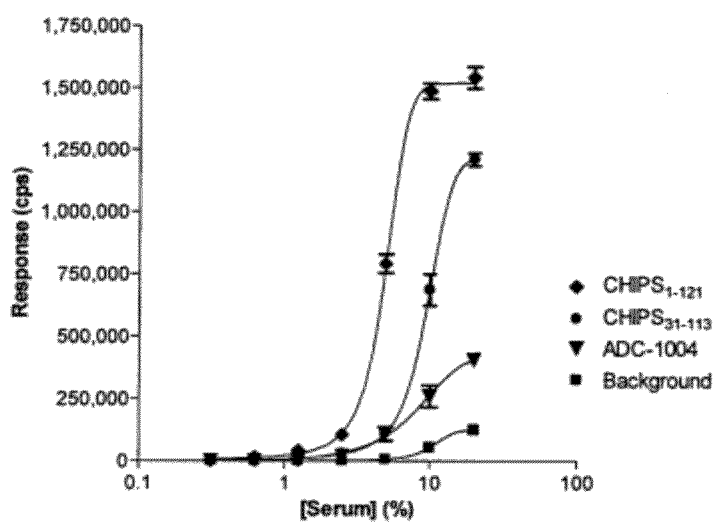
Figure 20:
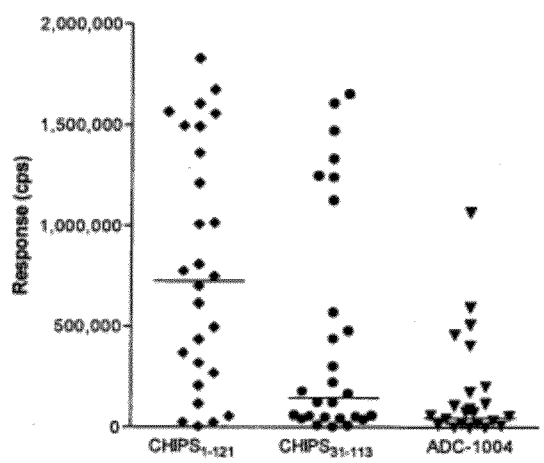

FIG. 20—ADC-1004 is a low-level inducer of complement activation. Complement fragment C3c deposition mediated by interaction between anti-CHIPS antibodies from human serum and CHIPS variants was studied in ELISA. ADC-1004 mediated C3c deposition was compared to the C3c deposition of CHIPS$_{1-121}$ or CHIPS$_{31-113}$. Serial dilutions of human serum was added to a plate coated with CHIPS variants or PBS. Deposition of complement fragment C3c was quantitated and plotted against the serum concentration. The C3c deposition using a pool of human serum is shown in (A) and the deposition at 10% serum using 28 different individual human sera is shown in (B). The line represents the median value.

Figure 21:
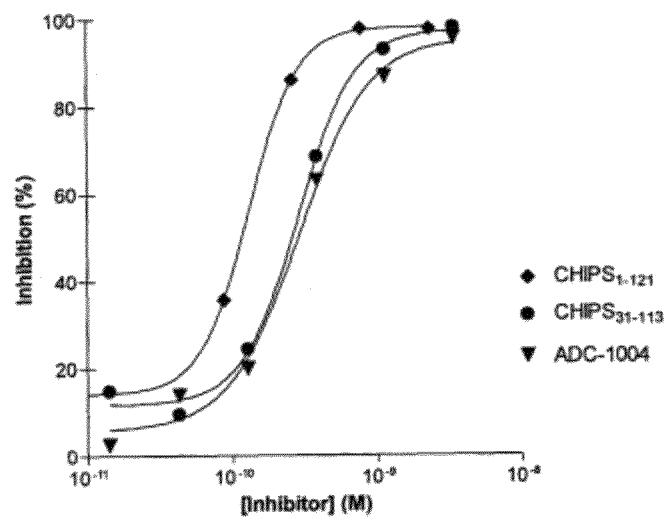
Figure 21:
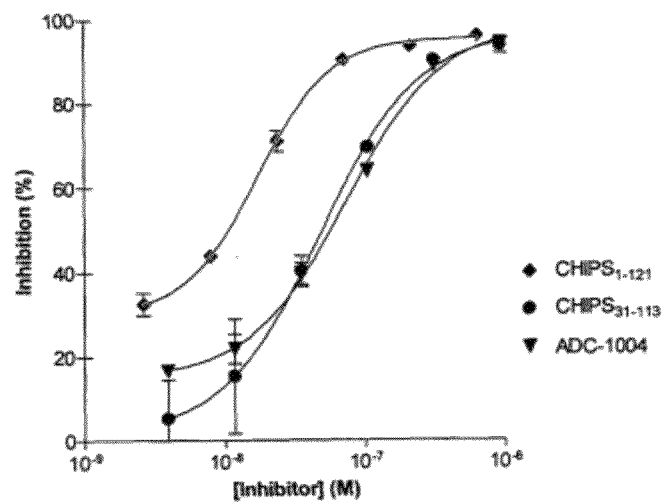

FIG. 21—ADC-1004 inhibits C5a induced neutrophil activation and migration. (A)—Fluo-3 labeled neutrophils were preincubated with an increasing concentration of CHIPS variants (CHIPS$_{1-121}$, CHIPS$_{31-113}$ or ADC-1004) and stimulated with a constant concentration of C5a (3 nM). Results are expressed as percent inhibition of buffer treated cells and are from a representative experiment. (B)—Calcein labeled neutrophils and a titration of CHIPS variants (CHIPS$_{1-121}$, CHIPS$_{31-113}$ or ADC-1004) were added to the upper compartment and 1 nM C5a to the lower compartment of a transwell system. Migration of labeled neutrophils was measured in a plate reader. Results are presented as percent inhibition of chemotaxis as compared to cells without addition of CHIPS.

Figure 22:
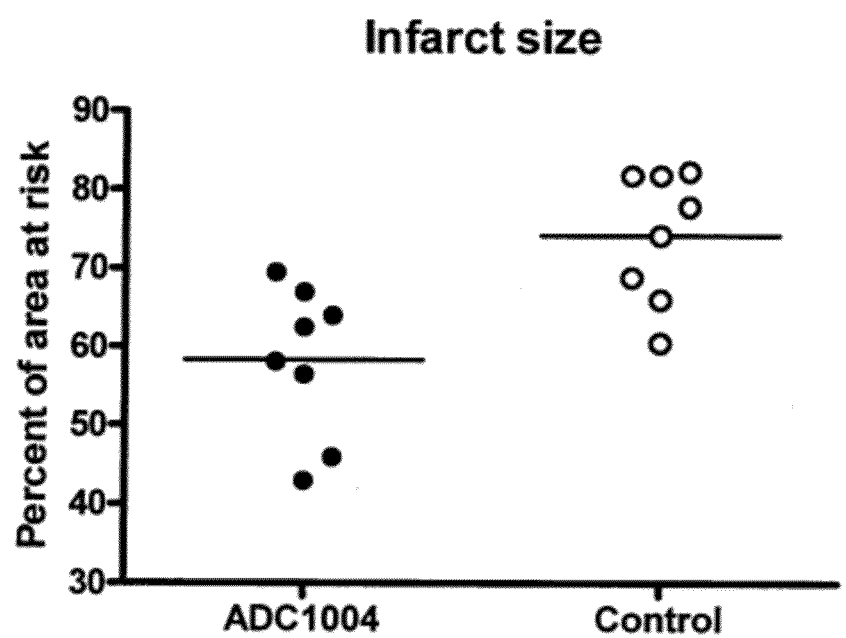

FIG. 22—ADC-1004 significantly reduces infarct size in relation to the ischemic area (area at risk) measured by MR/SPECT ($p<0.007$, Mann-Whitney U-test).

Figure 23:
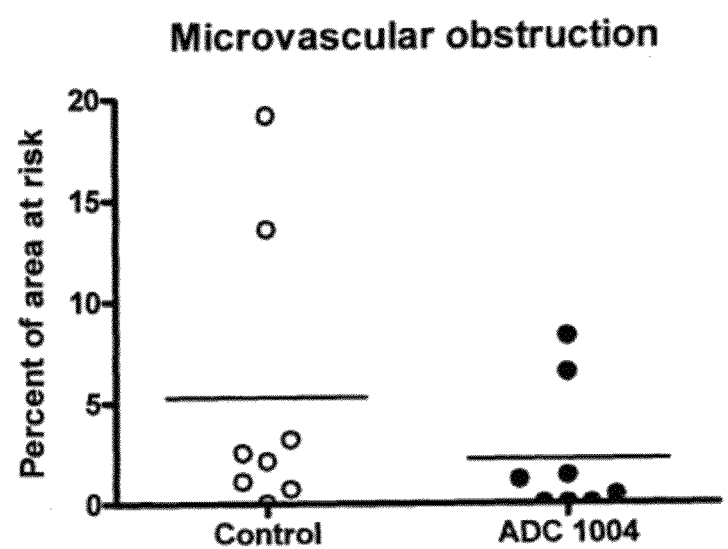

FIG. 23—ADC-1004 reduces micro vascular obstruction.

Figure 24A:
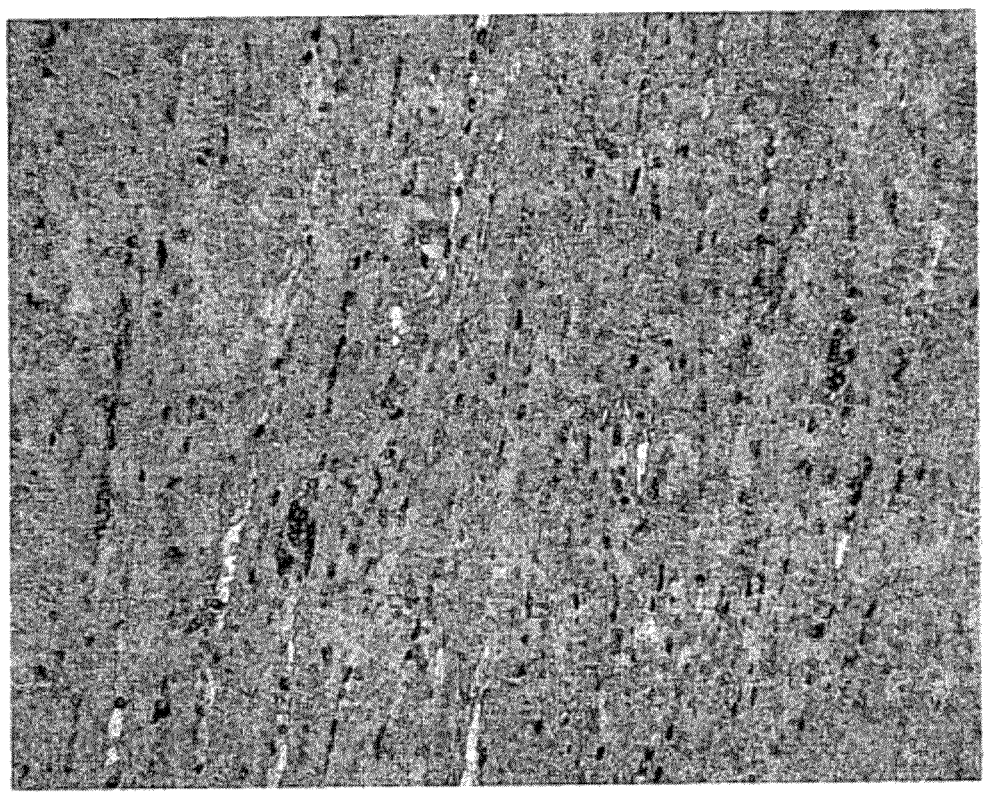

FIG. 24—Heart muscle tissue from infarct area from a placebo (A) and a ADC-1004 (B) treated animal stained for CD18 expression. Image analysis of the sections showed a lower staining in the ADC-1004 treated animal indicating a decrease in inflammatory cell activation.

Figure 25:
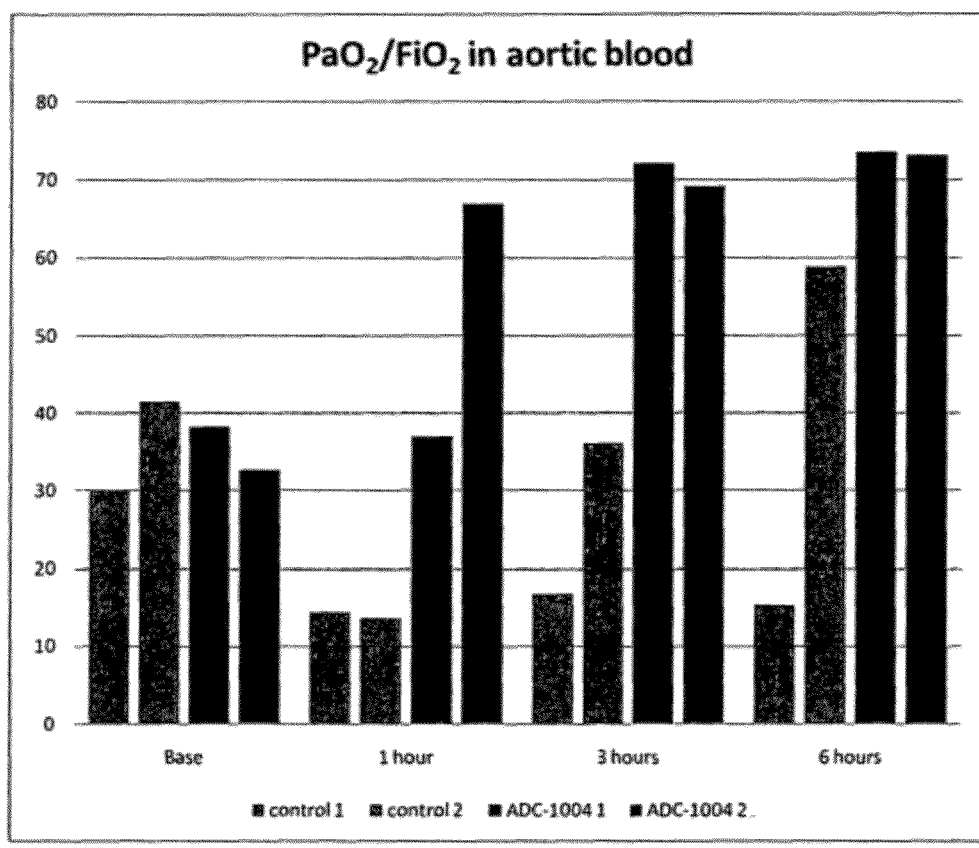

FIG. 25—PaO2/FiO2 in aortic blood at base (before transplantation), at 1, 3 and 6 hours after transplantation of two placebo treated animals (control 1 and 2) and two ADC-1004 treated subjects (ADC-1004 1 and 2).

EXAMPLE A

CHIPS Activity In vivo

Materials & Methods

Preclinical Assessment of CHIPS Toxicity in Animal Models

Different pre-clinical toxicology studies were preformed to investigate the safety of CHIPS. These included; (i) the effects of CHIPS on various cardiovascular and respiratory parameters in one group of three anesthetized beagle dogs. The dogs were administered CHIPS in incremental doses 0.2, 2.0 and 20 mg·kg$^{-1}$, infused intravenously over 1 minute at approximately 30 minute intervals. (ii) Behavioral ('Irwin') test in mice: CHIPS was administered as a single intravenous injection to male ICR CD-1 mice (3 per group) at doses of 7.5, 25 and 75 mg·kg$^{-1}$ in order to assess effects on general behavior. An additional group received an equivalent volume (10 mL·kg$^{-1}$) of vehicle (0.9% w/v sterile saline). (iii) Acute intravenous toxicity study in rat: Intravenous administration of 96.1 mg·kg$^{-1}$ CHIPS as a single dose (the maximum practically achievable due to volume considerations) to 5 male and 5 female rats. (iv) Acute intravenous toxicity in mice: Intravenous administration of 96.1 mg·kg$^{-1}$ CHIPS as a single dose to 5 male and 5 female mice. (v) Seven-day intravenous bolus preliminary toxicity study in rats (24 males and 24 females, max dose 10 mg·kg$^{-1}$). (vi) Seven day intravenous bolus toxicity study in rats (76 males and 76 females, max dose 10 mg·kg$^{-1}$). (vii) Seven day intravenous bolus dose range finding study in dogs (2 males and 2 females, max dose 20 mg·kg$^{-1}$). (viii) Seven day intravenous bolus toxicity study in the dogs (12 males and 12 females, max dose 20 mg·kg$^{-1}$).

Including Human Volunteers

Inclusion criteria for healthy volunteers were as follows: (i) Subjects should be men. (ii) Subjects should meet the following body mass index (BMI) range: 18-30 (kg·m2) and age range: 18-50 years, both inclusive. (iii) Medical screening was divided in 2 parts. Subjects were pre-screened for anti-CHIPS antibody levels. Only subjects with a low titer were screened for the second part within 3 weeks before dosing and include: medical history, physical examination, measurement of blood pressure, heart rate, respiration and temperature, alcohol breath test, blood and urine tests, electrocardiogram (ECG) and drug screening.

Admission and Follow-Up

Six selected subjects (4 receiving CHIPS and 2 controls) were admitted to the Clinical Pharmacology Unit (Kendle, Utrecht, The Netherlands) on the day before dosing. Baseline measurements, including blood samples for safety, urinalysis, interim medical history, physical examination, vital signs and ECG were done. On the day of dosing wildtype CHIPS (0.1 mg·kg$^{-1}$ administered as a single dose of sterile frozen isotonic saline solution containing CHIPS at a concentration of 5 mg·mL$^{-1}$) or placebo (0.9% NaCl) was administered by iv infusions over 5 minutes. Subjects were connected to a telemetry system for cardiac monitoring from 30 minutes before dosing until 4 hours after start of dosing. The blood pressure of subjects was measured continuously using a Finapres from 5 minutes before dosing until 30 minutes after start dosing. Vital signs were measured and ECGs were made at certain time points during the admission period. For safety, clinical status and laboratory values (haematology, biochemistry, coagulation and urinalysis) of all subjects were monitored. Adverse events were documented and characterised according to their severity and relationship to CHIPS or placebo. The subjects were discharged at 24 hours after dosing. Two weeks after dosing subjects returned to the Unit for a visit to evaluate vital signs, ECG, blood and urine and anti-CHIPS antibody level. A follow up visit was scheduled 6 weeks after dosing.

Cloning and Expression of CHIPS

CHIPS was cloned and expressed as described in Haas et al. (2004) *J. Immunol.* 173:5704-11. Briefly, the gene, without the signal sequence, was cloned into the pRSET vector directly downstream of the enterokinase cleavage site and before the EcoRI restriction site by overlap extension PCR. Bacteria were lysed with CelLytic B Bacterial Cell lysis/Extraction Reagent (Sigma) and lysozym according to the manufacturer's description. The histidine-tagged protein was purified using a nickel column (HiTrap® Chelating HP, 5 mL, Amersham Biosciences) following the manufacturer's instructions and cleaved afterwards with enterokinase (Invitrogen). Samples were checked for purity and presence of protein by means of 15% SDS-PAGE (Polyacrylamide gel electrophoresis, Mini Protean® 3 System, Bio-Rad) and Coomassie Brilliant Blue (Merck) staining.

Purification of CHIPS for iv Use

Full length CHIPS was expressed in an *E. coli* strain containing the coding sequence of CHIPS directly downstream a PelB coding sequence in a growth media consisting of Soya peptone and yeast extract in 8 L fermentation media. CHIPS was isolated both from the growth media and the cells by a two-stage cation exchange purification process followed by a desalting step. Bacterial cell pellet was re-suspended in phosphate buffer (30 mM; pH 7.0), containing NaCl (10 mM), DTT (10 mM) and frozen. This was subsequently thawed at 37° C., incubated on ice and sonicated. After centrifugation at 15,000 rpm an amber coloured "cell" supernatant was recovered. The supernatant was diluted four-fold with 30 mM phosphate buffer and passed over a Source S-30 column. Material was eluted with a phosphate buffer salt gradient and fractions containing CHIPS were combined and purified further by using a polishing column with a shallow salt gradient. Fractions containing CHIPS with purity greater than 97% (by HPLC) were combined and passed through a Sephadex® G 25 desalting column to remove phosphate and excess of sodium chloride. Endotoxin was removed by gently shaking over an affimix resin (Biorad) and the preparation was sterilized through ultra filtration. The purity was checked by HPLC-MS on a Microbondapac CN-RP column with a gradient mobile phase consisting of water-TFA to Methanol-TFA. CHIPS generally eluted at about 13 minutes. The product was diluted with sterile saline to the required concentration and stored at −20° C.

Anti CHIPS Antibodies

Rabbits were immunised with recombinant CHIPS using Freund's Complete Adjuvants and boosted with Freund's incomplete adjuvants. Bleedings were checked for reactivity with CHIPS by ELISA as described earlier (see Haas et al., 2004, *J Immunol* 173(9):5704-11). From the final bleeding, IgG was purified by standard Protein-G (Pharmacia) affinity chromatography according to the manufacturer's instructions. Specific mouse monoclonals towards CHIPS were generated as described and IgG purified with Protein-G Sepharose columns (see Haas et al., 2004, *J Immuno/*173(9): 5704-11).

Isolation of Affinity Purified Human-α-CHIPS IgG $CHIPS_{1-121}$ was coupled to a solid matrix using CNBR-activated Sepharose 4B according to the manufacturer's general instructions (Pharmacia, GE). Approximately 8 mg of purified CHIPS was coupled onto 1 gram Sepharose. A small column (±1 mL) was packed with the material, equilibrated with PBS and slowly perfused with human IgG for intravenous use (IgG-IV; Sanquin, Amsterdam, The Netherlands) diluted in PBS. The column was extensively washed with PBS and subsequently eluted with 0.1 M Glycine HCl buffer at pH 3. Fractions of 0.5 mL were collected into tubes containing 50 µL 1 M Tris/HCl pH8, for neutralization. Fractions with the highest $OD_{280}$ were pooled and dialyzed against PBS. The final preparation was analyzed for IgG content with an ELISA. Therefore plates were coated with sheep anti-human IgG (ICN) at $2\,\mu g \cdot mL^{-1}$ in PBS, blocked with 5% BSA and incubated with serial dilutions of a standard IgG preparation (reference serum; Boehringer) and unknowns. Captured IgG was detected with a peroxidase labeled goat anti-human IgG (Southern) and TMB as substrate. The IgG concentration was calculated from the reference curve.

Anti-CHIPS ELISA

Microtitre plates (Greiner) were coated with 50 µL CHIPS per well at $1\,\mu g \cdot mL^{-1}$ in PBS overnight at 4° C. All wash steps were performed thrice with PBS-0.05% Tween-20 and subsequent incubations were done for 1 hour at 37° C. Plates were blocked with PBS-0.05% Tween-20 4% BSA, washed and incubated with sera or antibodies diluted in PBS-0.05% Tween-20 1% BSA. Bound antibodies were detected with species-specific goat anti-IgG conjugated with peroxidase (all from Southern, Birmingham, USA) and TMB as substrate. The reaction was stopped with H2SO4 and the absorbance measured at 450 nm in a BioRad ELISA-reader.

Capture ELISA

Microtitre plates were coated with 50 µL α CHIPS mAb 2G8 at 3 µg·mL-1 in PBS overnight at 4° C. Plates were blocked with 4% BSA in PBS containing 0.05% Tween-20, washed and incubated with diluted samples and a two-fold dilution range of CHIPS as standard in PBS/Tween containing 1% BSA. Subsequently, plates were incubated with 0.33 µg·mL"1 rabbit α-CHIPS IgG and 1:5000 diluted peroxidase-conjugated goat anti-rabbit IgG (Southern). Bound antibodies were quantified with TMB as substrate, the reaction stopped with 1 N H2SO4 and measured at 450 nm on a BioRad ELISA reader.

Isolation of Human PMN

Blood obtained from healthy volunteers was collected into tubes containing sodium heparin (Greiner Bio-One) as anticoagulant. Heparinised blood was diluted 1/1 (v/v) with PBS and layered onto a gradient of 10 mL Ficoll® (hydrophilic polysaccharide, Amersham Biosciences, Uppsala, Sweden) and 12 mL Histopaque® Histopaque (hydrophilic polysaccharide and sodium diatrizoate; density $1.119\,g\,mL^{-1}$; Sigma-Aldrich, St. Louis, Mo.). After centrifugation (320×g, for 20 min at 22° C.), the neutrophils were collected from the Histopaque® phase and washed with cold RPMI 1640 medium containing 25 mMHEPES buffer, L-glutamine (Invitrogen Life Technologies) and 0.05% HSA (Sanguin). The remaining erythrocytes were lysed for 30 s with ice-cold water, after which concentrated PBS (10×PBS) was added to restore isotonicity. After washing, cells were counted and resuspended in RPMI-1640/0.05% HSA at 107 neutrophils mL-1.

Neutrophil Antigen Expression

Whole blood was collected into K3-EDTA tubes and put on ice. Optimal dilutions of fluorescent-labeled mAb were alliquoted into Falcon tubes and mixed with 50 µL blood for 30 min on ice under gentle agitation. Red blood cells were lysed with FACS-Lysing solution (BD) followed by a buffer wash and cell pellets resuspended into 0.5% paraformaldehyde in PBS with 0.1% azide. Neutrophil surface antigen expression was analyzed in a FACsCalibur™ FACsCalibur based on forward and sideward scatters for gating. Calibration beads (Calibrite™; BD) and isotype matched controls were used to set appropriate background values and electronic compensation. The following mAb and probes were used: anti-CD11b (CR3) APC-labeled (clone 44; BD); anti-CD62L (L-selectin) PE-labeled (clone Dreg 56 BD); anti-CD88 (CSaR) FITC-labeled (clone W17/1; Serotec); Fluorescein labeled formyl-Nle-Leu-Phe-Nle-Tyr-Lys ('FITC-fMLP'; Molecular Probes); Rabbit anti-CHIPS IgG (EWI) and FITC-labeled F(ab)'2 Goat anti-Rabbit IgG (Sigma).

Whole Blood Ex vivo Stimulation

Part of the K3-EDTAblood was kept at room temperature and used for ex vivo neutrophil stimulation. Therefore blood was mixed with 10-fold concentrated stimuli (buffer control, $1\times10^{-8}$ MfMLP) and incubated for 30 min at 37° C. with gentle shaking. Tubes were put on ice to stop the reaction and mixed with anti-CD11b plus anti-CD62L mAb. After 30 min on ice samples were treated as described above.

CD11b expression on CHIPS/IgG Stimulated Neutrophils

Different concentrations CHIPS (final concentration 0-9 $\mu g \cdot mL^{-1}$) were incubated with affinity purified human-α-CHIPS-IgG (0-40 $\mu g \cdot mL^{-1}$) for 30 min at 37° C. Thereafter, 50 µL isolated human neutrophils ($10^7\,mL^{-1}$) were added to the CHIPS/α-CHIPS mixture and incubated with gentle shaking for 30 min at 37° C. Cells were put on ice for 10 min after which 3.5 µL flourescent mouse-α-human-CD11b (BD-biosciences, San Diego, Calif.) was added and incubated on ice for 30 min. Cells were washed with RPMI 1640/0.05% HSA and fixed with 200 µL 0.5% paraformaldehyde.

CD11b expression on cells in whole blood was performed using blood collected from human volunteers, selected for different α-CHIPS titers. Since IgG is already present in the whole blood the samples (50 µL) were only incubated with CHIPS (0-9 $\mu g \cdot mL^{-1}$) for 30 min at 37° C. The sample was put on ice for 10 min after which 3.5 µL fluorescent labeled mouse-anti human-CD11b was added and incubated on ice for 30 min. The erythrocytes were lysed and cells were fixed by adding 1 mL FACS lysing solution diluted 1:10 with $H_2O$ for 4 min. Cells were spun for 10 min at 1200 rpm and pellet was washed with ice cold RPMI 1640/0.05% HSA. Finally cells were resuspended in 175 µL RPMI 1640/0.05% HSA. Receptor expression representing cell activation was measured in a FACSCalibur flowcytometer (BD Biosciences).

Circulating Immune Complexes (CIC)

CIC were determined by 2 different ELISAs from Quidel (San Diego, Calif.): the CIC-C1q enzyme immunoassay is based on the principle that complement fixing IC will bind to immobilised human C1q purified protein; the CIC-Raji Cell Replacement enzyme immunoassay measures IC containing C3 activation fragments by using a mAb that specifically binds the iC3b, C3dg and C3d activation fragments of C3 in a manner which is analogous to the classical Raji cell CR2 binding reaction. The data of both assays were combined and results expressed relative to the value at time point 0.

Serum Tryptase Concentration

Serum derived tryptase (both α and β form) was measured on the UniCAP®-100 (autoimmunoassay) using the ImmunoCAP™ technology (solid phase immunodiagnostic) from Pharmacia Diagnostics (Woerden, The Netherlands). The normal geometric mean for healthy controls is 5.6 µL-1 (Pharmacia). Results were expressed relative to the value at time point 0.

The study protocol and any amendments were approved by an independent ethics committee. The study was performed in compliance with the European Community (EC) rules of Good Clinical Practice (GCP) and the 'Declaration of Helsinki' (2000).

Results

CHIPS Shows No Evident Toxicity in Pre-Clinical Toxicology Studies

In none of the toxicology animal studies did administration of CHIPS cause any CHIPS related toxicologically significant changes in clinical observations, body weight, food consumption, haematology, coagulation, blood chemistry parameters, ophthalmoscopy, electrocardiograms, macroscopic or microscopic pathology or behavior.

The effects of CHIPS on various cardiovascular and respiratory parameters in anesthetized beagle dogs was examined. In the dogs receiving low dose CHIPS (0.02 and 2 $mg \cdot kg^{-1}$) there was no evidence of cardiovascular or respiratory effects when compared to infusion of vehicle (isotonic saline). Following intravenous administration of 20 $mg \cdot kg^{-1}$ CHIPS a transient decrease in mean arterial blood pressure (−40%) was recorded approximately 1 minute after start of administration. Mean arterial blood pressure levels returned to pre-dose levels within approximately 5 minutes following the start of dosing. The effect on blood pressure coincided with transient, inconsistent changes in heart rate. One dog was administered a repeat intravenous dose of CHIPS (20 $mg \cdot kg^{-1}$) approximately 30 minutes following the first administration of CHIPS. Transient effects on cardiorespiratory parameters similar to those recorded following the first dose were not apparent after the repeat administration of CHIPS. However, the second administration produced a prolonged reduction in mean arterial blood pressure reaching a maximum of 18% at approximately 30 minutes following the second administration. In this animal only, twelve minutes following the repeated administration of CHIPS a generalized skin reaction appeared consistent with some form of mild allergic reaction.

The results of this study suggested that cardiorespiratory effects are unlikely to be observed in the human subjects in the used dose range (0.1 $mg \cdot kg^{-1}$). Furthermore, any effects that might occur were expected to be transient and reversible.

Distribution of α-CHIPS Antibody Titers

Since *S. aureus* is a common bacterium and the CHIPS gene is present in the majority of *S. aureus* strains we hypothesized that all individuals possess circulating α-CHIPS antibodies. Therefore we tested the amount of α-CHIPS IgG in serum of healthy volunteers. FIG. 1 shows the distribution of α-CHIPS IgG titers in a set of 168 healthy human volunteers. In the set of measured samples there were no titers below the detection limit of the used ELISA. The studied population is considered representative for the general population. Concluding from this data, over 99% of people in the general population have detectable α-CHIPS IgG serum levels. Also indicated in FIG. 1 are the titers of the subjects included in the trial.

Pharmokinetics of iv Administered CHIPS

At four different time points after CHIPS administration the CHIPS serum titers were determined by ELISA (FIG. 2). Increase in CHIPS titer was observed only in individuals receiving CHIPS that had a low α-CHIPS antibody titer, (subjects 104 and 105). We determined the effect of human serum on the CHIPS ELISA. CHIPS was spiked into various concentrations pooled human serum and detected by capture ELISA. FIG. 3*a* shows that serum inhibits the capture ELISA. Depletion of IgG using a protein G-sepharose column eliminates the inhibitory effect (FIG. 3*b*).

CHIPS binds the FPR and C5aR in vivo

CHIPS binds the FPR and C5aR on neutrophils with high affinity and can be detected with α-CHIPS antibodies as described earlier for mouse mAb.158 At various timepoints after CHIPS administration the amount of CHIPS present on the surface of neutrophils was determined using a rabbit-α-CHIPS antibody as shown in FIG. 4. Only in subjects with a low α-CHIPS antibody titer (subjects #104 and #105) CHIPS was detected on the surface of neutrophils. Moreover, within these two subjects the detection of CHIPS negatively correlates to the α-CHIPS antibody titer. Since α-CHIPS antibodies present in serum interfere with the direct detection of CHIPS a negative result of this direct detection can not exclude CHIPS binding the receptor. However, CHIPS bound to the FPR and C5aR interferes with the detection of these receptors by α-FPR and α-C5aR antibodies as described earlier (see Veldkamp et al., 2000, *Infect Immun* 68(10):5908-13). FIG. 5 shows the FPR and C5aR receptor expression determined by FITC-fMLP and α-C5aR antibody binding. Subjects with a low α-CHIPS antibody titer show a decrease in FPR and C5aR expression indicating that CHIPS has occupied the receptors. In the subjects with a high α-CHIPS antibody titer (103 and 106) there is no change in FPR and C5aR expression indicating that α-CHIPS antibodies interfere with CHIPS binding to the receptor.

CHIPS Inhibits fMLP Induced Neutrophil Activation Ex vivo Dependent of α-CHIPS Antibody Titer Upon cell activation there is a decrease in CD62L expression and an increase in CD11b expression. In order to test the effects of intravenous CHIPS on neutrophil inhibition we measured ex vivo fMLP-induced expression of CD62L and CD11b. Neutrophils were activated ex vivo with fMLP in a whole blood assay. As shown in FIG. 6, intravenous administered CHIPS is able to inhibit fMLP induced activation of neutrophils ex vivo. This inhibition is only observed in subjects with a detectable CHIPS serum concentration (subject 104 and 105).

CHIPS Induced Adverse Effects

Serious side effects were observed directly after administration of CHIPS. Most serious adverse events were observed for subject 106, these included: muscle pain, dyspnea, abdominal pain, vomiting, muscle spasms, chills, sweating, edema orbita and dizziness. The conclusive diagnosis of these symptoms is anaphylactoid reaction. The subject was treated with clemastine, IV fluids, tramadol and prednisolone.

Other adverse events reported include: palpitations, feeling warm, chest pain, flushing, feeling cold, tired legs, postural dizziness, fever, headache, nausea, blurred vision. Apart from the severe back pain for subject 106, subjects 103 and 105 reported mild back pain. Subject 104 reported muscle cramps. Fever up to 38.6° C. was observed for subjects 104 and 105 starting approximately 4 hours post dosing with resolution in the evening of day 1.

There were no changes in blood pressure and no ECG abnormalities. No abnormalities in oxygen saturation were observed except for intermittent low readings for subject 106 (89% oxygen saturation) during the adverse events described above. No adverse events were reported in subjects receiving placebo.

Intravenous CHIPS Induces a Leukocytopenia and Increased CRP Levels

We measured the white blood cell count (WBC) and C-reactive protein concentration (CRP) pre- and post-dosing as shown in FIG. 7. CHIPS induced a transient leuko-cytopenia in the subjects receiving CHIPS that resolved within 2 days. Furthermore there is an increase in CRP concentration starting at day 1 post dose that had returned to normal levels when subjects were screened during follow up at day 15. (FIG. 7b).

Circulating Immune Complexes and Increase Serum Tryptase Indicate an Anaphylactoid Reaction We measured the amount of circulating immune complexes and the serum tryptase concentration. Intravenous administration of CHIPS induces the formation of immune complexes in subjects receiving CHIPS (FIG. 8a). We also observed an increase in tryptase serum concentration that reached a maximum at approximately 10 minutes post dose (FIG. 8b).

CHIPS Induces Cell Activation In vivo

To study the direct effect, of CHIPS on cell activation we determined the CD62L and CD11b receptor expression on neutrophils. Receptor expression was measured immediately after collection of blood samples without any further cell stimulation. Subjects 104, 105 and 106 show a decrease in CD62L and a increase in CD11b expression on neutrophils representing in vivo cell activation (FIG. 9).

α-CHIPS Antibody Titers Increase after CHIPS Administration

The immunogenicity of a protein is characterized by the potency to induce antibodies. We determined the immunogenicity of CHIPS in healthy human subjects. The subjects that received intravenous CHIPS show an increase in α-CHIPS IgG (FIG. 10).

CHIPS Activation of Neutrophils In vitro is Dependent on Antibody Concentration

We studied the activation of neutrophils by CHIPS-IgG complexes in vitro. Different concentrations CHIPS were preincubated with 20 µg·mL$^{-1}$ human affinity purified-α-CHIPS IgG and used to stimulate isolated neutrophils as shown in FIG. 11. Affinity purified-α-CHIPS IgG was not able to activate neutrophils in the absence of CHIPS (data not shown). CHIPS-IgG complexes were able to stimulate neutrophils in a dose dependant way. FIG. 11 also shows that there is an optimal CHIPS concentration needed for maximal cell activation. The CHIPS-IgG induced cell activation was completely inhibited by FcR blocking antibodies. Therefore we conclude that the CHIPS-IgG induced cell activation in this assay is Fc-receptor mediated.

CHIPS$_{R46A}$ (arginine at position 46 replaced with alanine) and CHIPS$_{K69A}$ (lysine at position 96 replaced with alanine) are two CHIPS mutants with a single amino acid substitution, described earlier (see Haas et al., 2005, *J Mol Biol* 353(4): 859-872). These CHIPS mutants show a decreased affinity for purified-α-CHIPS IgG as measured by ELISA (data not shown). When used in the whole blood cell activation assay these mutants have a lower cell activating potential compared to wild type CHIPS (FIG. 12). For CHIPS$_{R46A}$ and CHIPS$_{K69A}$ a ten fold higher concentration is needed to give the same cell activation compared to wild type CHIPS. This shows that next to the antibody titer the level of reactivity with the antigen determine the amount of cell activation.

Ex Vivo Activation of Neutrophils by CHIPS is Also Dependent on α-CHIPS IgG Concentration We measured the effect of CHIPS on neutrophil activation in a whole blood ex vivo assay. Since α-CHIPS antibodies are already present in whole blood we did not preincubate CHIPS with affinity purified-α-CHIPS IgG. Different concentrations CHIPS were added to blood from human volunteers and CD11b expression, representing cell activation was measured. FIG. 13 shows the CHIPS concentration needed for maximal neutrophil stimulation measured by CD11b expression in whole blood from 8 healthy volunteers with different α-CHIPS IgG titers. As shown in the in vitro experiments maximum neutrophil stimulation depends on the CHIPS/α-CHIPS ratio. This is also observed in this ex vivo assay. A higher concentration CHIPS is needed for maximum stimulation of neutrophils when a higher α-CHIPS concentration is present.

Discussion

The Chemotaxis Inhibitory Protein of *S. aureus* is a very potent inhibitor of the human C5a-receptor and formyl-peptide-receptor. Both receptors, but especially the C5aR, have been described as important targets in the treatment of a variety of inflammatory diseases. The potent capacity of CHIPS to inhibit the C5aR and FPR make this protein a candidate therapeutic agent in the treatment of these diseases. Furthermore the fact that the activity towards the C5aR and the FPR are located on distinct regions of the CHIPS molecule allows for specific receptor targeting (see Haas et al., 2004, *J Immunol* 173(9):5704-11). The human specificity of the CHIPS protein, as evident from a 30 fold difference in activity toward human cells compared to mouse cells, hampers the evaluation of in vivo CHIPS activity in an animal model (see de Haas et al., 2004, *J Exp Med* 199(5):687-95).

We studied the activity, pharmokinetics and toxicity of the Chemotaxis Inhibitory Protein of *S. aureus* in a set of six healthy human subjects. Pre-clinical toxicology studies with administration of high concentrations CHIPS (single intravenous doses up to 96.1 mg·kg$^{-1}$ in mouse) in different animal models show no remarkable signs of toxicity. Therefore a starting dose of 0.1 mg·kg$^{-1}$ administered intravenously over 5 minutes was considered safe.

Since *S. aureus* is a common bacterium and the CHIPS protein is expressed in the majority of *S. aureus* strains we hypothesized that α-CHIPS antibodies are present in all individuals. This was confirmed by screening of α-CHIPS IgG titres in a pool of 168 randomly collected sera from human volunteers. Experiments with mouse monoclonal antibodies showed that these monoclonal antibodies can interfere with CHIPS activity in vitro (see Haas et al., 2004, *J Immunol* 173(9):5704-11). Therefore, it is reasonable to assume that α-CHIPS antibodies present in the healthy subjects receiving the CHIPS protein also interfere with activity.

The administration of CHIPS to human subjects was an unique opportunity to study activity and pharmokinetics in vivo. After intravenous administration of 0.1 mg·kg$^{-1}$ CHIPS we measured the CHIPS serum concentration. FIG. 2 shows the CHIPS serum concentration on different time points post dosing. In only two out of four subjects that received the CHIPS protein we measured an increase in CHIPS serum concentration (subject 104 and 105). Interesting was the observation that these two individuals also showed the lowest α-CHIPS IgG titers. This shows that α-CHIPS antibodies interfere with the detection of CHIPS. Consequently, because of this interference the measured CHIPS serum concentration in subjects 104 and 105 is an underestimation. Based on these data we calculated a predicted half life of CHIPS in vivo of at least 1.5 hours.

We observed the same correlation with α-CHIPS IgG titer when detecting the amount of CHIPS present on the neutrophil membrane surface. CHIPS could be detected on the surface of neutrophils from subjects 104 and 105 only. Furthermore, we showed that these CHIPS molecules occupy the FPR and C5aR since there is a downregulation in the detection of both receptors by α-FPR and α-C5aR antibodies in these individuals. Also, only neutrophils from subjects 104 and 105 showed a decreased activation upon stimulation with fMLP. Unfortunately, experiments with C5a stimulation failed due to technical problems. However these experiments clearly show that intravenous administered CHIPS has an inhibitory effect on neutrophil activation ex vivo and that this effect is inhibited by α-CHIPS antibodies.

No relevant adverse effects were observed in pre-clinical animal toxicity studies. The administration of 0.1 mg·kg$^{-1}$ CHIPS in human subjects was tolerated by 2 subjects (subjects 103 and 104) moderately tolerated in subject 105 but subject 106 developed serious symptoms directly after the CHIPS infusion, which were diagnosed as an anaphylactoid reaction. We measured the neutrophil CD11b surface expression in all subjects to investigate CHIPS-induced cell-activation. Activation of cells was observed for subjects 104, 105 and 106. Within the group of subjects that received CHIPS there was a increase in C-reactive protein at day 2 post dose compared to controls.

Mast cells, which are leukocytes found in peripheral tissue, play a central role in inflammation and immediate allergic reactions. The release of tryptase from the secretory granules is a characteristic feature of mast cell degranulation. Serum mast cell tryptase concentration is increased in anaphylaxis and in other allergic conditions (see Payne & Kam, 2004, *Anaesthesia* 59(7):695-703). The anaphylactoid reaction, observed after CHIPS administration, was confirmed by an increase in tryptase levels representing mast cell activation. The rise in tryptase levels was preceded by an increase in circulating immune complexes. Immune complexes can activate mast cells by FcγR crosslinking and through activation of complement and the generation of C5a (see Jancar & Crespo, 2005, *Trends Immunol* 26(1):48-55).

In vitro experiments confirmed the cell activating properties of CHIPS in the presence of α-CHIPS antibodies. CHIPS induced neutrophil activation was inhibited by blocking FcγRII and FcγRIII blocking antibodies. This indicates that the CHIPS induced activation of these cells is most likely caused by CHIPS/α-CHIPS immune complexes. When we look for circulating immune complexes in the tested subjects we also find an increase in immune complexes in the subjects receiving intravenous CHIPS. The relation between α-CHIPS antibody titer and CHIPS induced cell activation is also clear from the in vitro and ex vivo experiments. This is in contrast with the observation that subject 103, who has the highest α-CHIPS antibody titer, reports only minor adverse effects. Of course, the studied population was limited to only 4 subjects and a large amount of different factors influence the development and perception of the adverse effects within an individual. Furthermore, in vitro experiments demonstrate that there is an optimal antibody concentration that induces cell activation. It is possible that a very high α-CHIPS antibody titer decreases the development of an anaphylactoid reaction. Earlier studies showed that CHIPS does not bind other cells than those expressing the C5aR and FPR and there is no evidence of direct cell activation by CHIPS. Although antibodies clearly play a role in cell activation the small number of observations and the complexity of in vivo hampers interpretation of these data.

We demonstrated that two CHIPS mutants with a reduced affinity for α-CHIPS IgG (CHIPS$_{R46A}$ and CHIPS$_{K69A}$) show a decreased cell activating potential in vitro. Despite the neutralizing effect of α-CHIPS antibodies we were able to detect significant serum concentrations of the CHIPS protein. Moreover intravenous administered CHIPS was detected on circulating neutrophils, bound to the FPR and C5aR and able to inhibit neutrophil responses upon ex vivo stimulation with fMLP. This indicates that the CHIPS protein is able to find its target, the FPR and C5aR, in vivo.

We showed that the half-life of the CHIPS protein in serum is approximately 1.5 hours. Furthermore, the same half life was also observed for CHIPS bound to its receptors on the cell surface indicating a functional half life in the same order of magnitude. This indicates that the CHIPS protein is not immediately cleared from the blood. It might be possible to increase the half life of the CHIPS protein by introducing point mutations, as has been shown for streptokinase, a protein drug used for thrombolysis in acute myocardial infarction (see Wu et al., 1998, *Appl Environ Microbiol* 64(3):824-829). However, a half-life of 1.5 hours implies that any (immunosuppressive) effect will rapidly disappear when dosing is stopped. This could be an advantage over antibody drugs with a long half-life, like Infliximab, that has been associated with an increase in the incidence of infections (see Listing et al., 2005, *Arthritis Rheum* 52(11):3403-3412; Crum et al., 2005, *Medicine (Baltimore)* 84(5):291-302).

EXAMPLE B

Directed Evolution of CHIPS to Generate Functional Variants with Reduced Interaction with Human Antibodies Abstract Chemotaxis Inhibitory Protein of *Staphylococcus aureus* (CHIPS) is a protein that binds and blocks the C5a receptor (C5aR) and formylated peptide receptor, thereby inhibiting the immune cell recruitment associated with inflammation. If CHIPS was less reactive with existing human antibodies, it would be useful as an anti-inflammatory drug. Therefore, we applied directed evolution and computational/rational design to the CHIPS gene in order to generate new CHIPS variants displaying lower interaction with human IgG, yet retaining biological function. The optimization was performed in four rounds; one round of random mutagenesis to add diversity into the CHIPS gene and three rounds of DNA recombination by Fragment INduced Diversity (FIND®). Every round was screened by phage selection and/or ELISA for decreased interaction with human IgG and retained C5aR binding. The mean binding of human anti-CHIPS IgG decreased with every round of evolution. For further optimization, new amino acid substitutions were introduced by rational design, based on the mutations identified during directed evolution.

Finally, seven CHIPS variants with low interaction with human IgG and retained C5aR blocking capacity could be identified.

Introduction

Inflammation is the tissue response to injury or infection by pathogens. The attraction of immune cells and soluble molecules to the site of damage or infection initiates the healing process. Even though the ability to raise an inflammatory response is crucial for survival, the ability to control inflammation is also necessary for health. Anti-inflammatory drugs aim at blocking key events in inflammation for treatment of disorders with excessive or uncontrolled inflammation. Examples of such drugs are Remicade® and Kineret®, approved for treatment of rheumatoid arthritis.

Many bacteria have evolved strategies to evade the human immune system, for example by avoiding recognition, or by secreting proteins that neutralize the antibacterial effects mediated by the immune system. Chemotaxis Inhibitory Protein of Staphylococcus aureus (CHIPS) is a 14.1 kDa protein which is a potent inhibitor of immune cell recruitment and activation associated with inflammation, through binding and blocking the C5a receptor (C5aR) and the formylated peptide receptor (De Haas et al., 2004; Postma at al., 2004). This way, CHIPS is a promising anti-inflammatory protein for treatment of several inflammatory diseases, e.g. sepsis (Rittirsch et al., 2008) or ischemia-reperfusion injury and immune complex disease (Heller et al., 1999) However, most individuals have pre-formed titers of antibodies specific for CHIPS (Wright et al., 2007). These antibodies might neutralize the function of CHIPS or induce an immune reaction, hence the CHIPS molecule would benefit from optimization to function well as a drug in the human circulation.

Directed evolution is an established approach for improving proteins. It has been utilized to improve many protein functions such as stability, activity or affinity (Johannes et al., 2006). Importantly for the development of protein therapeutics, directed evolution has proven to be a useful tool for generating protein variants with enhanced therapeutic potential (Yuan et al., 2005). The directed evolution approach is particularly efficient as it does not require prior knowledge of the structure of the protein. Instead of using inefficient and time consuming methods based on site-directed mutagenesis, rounds of gene recombination and high-throughput screening can be performed to identify improved variants. The process can be repeated and beneficial mutations will be accumulated while mutations not required for the property of interest will be excluded, as reviewed by (Yuan et al., 2005) and (Zhao, 2007).

Several distinct methods for directed evolution have been described in the literature; among them DNA shuffling (Stemmer, 1994a; Stemmer, 1994b) and the Staggered Extension process (StEP) (Yuan et al., 2005; Zhao et al., 1998). Another DNA recombination technology called Fragment INduced Diversity (FIND®), has previously proven to be useful in the optimization of thermostability of carboxypeptidase U (Knecht et al., 2006) and the activity of IL-1 receptor antagonists (Dahlen et al., 2008).

Even though directed evolution has been successfully utilized to identify new and improved protein variants, a limitation with this type of technology is the incapability of screening the entire sequence space of a protein. However, sequence space can be explored more efficiently if directed evolution is combined with computational tools and rational design (Wong et al., 2007; Zhao, 2007).

In this example, FIND® was used in combination with rational/computational design of the CHIPS gene with the aim to create new protein variants with lower interaction with pre-existing specific human IgG. An improved CHIPS molecule would be characterized by decreased reactivity with pre-existing antibodies, but also preserved activity towards the C5aR. Therefore, receptor binding was monitored in parallel with the screening process for decreased IgG interaction. This way, we were able to isolate new CHIPS variants with significantly reduced interaction with human anti-CHIPS IgG yet preserved C5aR blocking activity.

Materials & Methods

Cloning, Expression and Purification of Recombinant Proteins

Wild-type (Wt) CHIPS$_{1-121}$ was cloned, expressed and purified as described earlier (De Haas et al., 2004). CHIPS with truncated C-terminus (CHIPS AC) was 112 amino acids long with two additional non-relevant amino acids included in the C-terminal end of the expressed protein as a result of cloning (CHIPS$_{1-112}$). Genes encoding CHIPS AC and its corresponding single mutants K61A, K69A and K100A as well as CHIPS ΔN/C(CHIPS$_{31-113}$) were created from the gene encoding wt full-length CHIPS$_{1-121}$ by truncation and site-directed mutagenesis. These CHIPS variants were then cloned and expressed as described above. Single mutants were used for structural analysis by Haas et al. (Haas et al., 2005), but were also screened for anti-CHIPS IgG binding and mutants K61A, K69A and K100A showed decreased binding (data not shown).

CHIPS variants selected from libraries in this study were expressed in the same way, but purified from inclusion bodies (Gustafsson et al., 2009) or expressed by the Expressway Cell-Free E. coli Expression System (Invitrogen, Carlsbad, Calif.) as recommended by the manufacturer.

Library Construction

Random Mutagenesis

To create diverse libraries of CHIPS variants in Round 1 (see FIG. 14), two different methods of random mutagenesis were used to create in total four libraries. Error-prone PCR was performed as described previously (Leung et al., 1989). One library with high mutation frequency (Library 1.1) and one with low mutation frequency (Library 1.2) were created. A 20 cycle PCR was performed using primers (Fw: 5'-TCGCGGCCCAGCCGGCCATGGCCTT-TACTTTTGAACCG-3' [SEQ ID NO: 3] and Rev: 5'-GCCT-GCGGCCGCAGATCTACCATTAATTACATAAG-3' [SEQ ID NO: 4]) in the presence of 7.5 mM MgCl$_2$ and 0.64 mM MnCl$_2$. 2.5 U AmpliTaq® Thermostable DNA polymerase (Applied Biosystems, Foster City, Calif.) was added and the reaction was performed using the program 94° C., 5 min/(94° C., 30 s/55° C., 30 s/72° C., 40 s) 20 times and finally elongation at 72° C. for 10 minutes. GeneMorph® II (error-prone PCR random mutagenesis kit, Stratagene, La Jolla, Calif.) was used as recommended by the manufacturer. 10 μg DNA (a mixture of CHIPS AC and the corresponding K61A, K69A and K100A single mutants) was used for the design of the low mutation frequency library (library 1.4) and 1 ng DNA for the library with higher mutation frequency (library 1.3). The PCR reaction contained the primers described and finally elongation at 72° C. for 10 minutes. To increase the mutation frequency in the 1 ng library, it was subjected to one more round of GeneMorph® II mutagenesis. This time, the amount of DNA in the PCR reaction was 10 ng. After purification, the PCR products were sub-cloned into the pGEM-T vector (Promega, Madison, Wis.) according to the manufacturer's recommendations and the sequences were analyzed and base exchanges evaluated.

FIND®

FIND® recombinations were performed in Rounds 2 to 4 to create diverse libraries of recombined clones, as described in e.g. patents EP 1 341 909 and EP 1 504 098. Briefly, single-stranded DNA was prepared by generating PCR products using one biotinylated and one regular primer. The PCR product was immobilized on a column containing streptavidin-conjugated magnetic beads (Miltenyi Biotec GmbH, Bergisch Gladbach, Germany) and placed in the magnetic field of a pMACS separator. The PCR product was denatured with 0.1 M NaOH and the eluted non-biotinylated DNA strand was collected and purified by agarose gel electrophoresis using Recochips (Takara Bio Inc., Shiga, Japan) according to the manufacturer's recommendations.

The FIND® experiments were initiated by fragmenting 200 ng sense and antisense ssDNA, respectively, with Exonuclease I (Exo I). (New England Biolabs, Ipswich, Mass.) (100 U/µg DNA) for 10 minutes, Exonuclease V (Exo V) (USB, Cleveland, Ohio) (25 U/µg DNA) for 45 minutes and Exonuclease VII (Exo VII) (USB) (10 U/µg DNA) for 30 minutes in separate tubes in buffers as recommended by the manufacturers. The ssDNA fragments resulting from the exonuclease digestions were recombined in a PCR-like reaction, without added primers, followed by amplification using a standard PCR protocol. After purification, PCR products were subcloned into the pGEM-T vector (Promega) according to the manufacturer's recommendations and sequences were analyzed.

Protein Expression in Plate Format

CHIPS libraries created by random mutagenesis or FIND® were cloned into a modified pRSET B vector (Invitrogen) in BbsI and BglII sites for expression in *E. coli*. Libraries were transformed into *E. coli* BL21 star DE3 pLysS (Invitrogen), plated on 20 cm Qtray plates with LB agar supplemented with 50 µg/ml ampicillin and 34 µg/ml chloramphenicol and incubated at 37° C. overnight. The following day, *E. coli* colonies were picked and inoculated in 96 well round bottom plates containing 150 µl Luria Broth (LB) supplemented with 50 µg/ml ampicillin and 34 µg/ml chloramphenicol using a colony picker robot. The cultures were incubated at 37° C. with 78% humidity and shaking at 700 rpm in a Multitron plate shaker (Infors HT, Bottmingen, Switzerland) overnight. Day cultures were prepared from the overnight cultures by 1/100 dilution into fresh medium with 50 µg/ml ampicillin and incubation was continued at 37° C. as above. To induce protein expression, 0.5 mM IPTG (isopropyl β-D-thiogalactoside) was added to the cultures after three hours, and the cultures were then cultivated for another three hours. *E. coli* cultures were pelleted by centrifugation and pellets were frozen at −20° C. Lysates were prepared by freeze-thawing the *E. coli* pellet in PBS 0.05% Tween 20 with Complete EDTA-free protease inhibitor (Roche, Basel, Switzerland), 25 U/ml Benzonase® (endonuclease, Sigma-Aldrich, St Louis, Mo.) and 1 KU/ml rLysozyme (EMD Chemicals, Darmstadt, Germany) and incubation for 10 min at room temperature with shaking.

Site-Directed Mutagenesis

Site-directed mutagenesis was performed using the QuikChange II mutagenesis kit (Stratagene) according to the manufacturer's recommendations with primers carrying the specific mutation. The new CHIPS variants were sequence verified and transformed into *E. coli* BL21 Star(DE3)pLysS (Invitrogen) for protein expression.

Affinity Purification of Human Anti-CHIPS$_{31-113}$ IgG

Purified CHIPS$_{31-113}$ was coupled to CNBr activated Sepharose® 4B (crosslinked, beaded-form of a polysaccharide polymer; Amersham Biosciences, Uppsala, Sweden) and packed on a Tricon 5/20 column (Amersham Biosciences) according to the manufacturer's instructions. Affinity purification was performed on an AKTAprime® (liquid chromatography) system (Amersham Biosciences) according to the manufacturer's protocol. Total human IgG (1 g) (IV-IgG) (Sanquin, Amsterdam, The Netherlands) was run over the column and then bound human IgG was eluted with 0.1 M glycine pH 3.0 and the pH neutralized with 1 M Tris, pH 8.0. Eluted fractions containing protein were pooled and buffer was changed to PBS on PD-10 columns (Amersham Biosciences).

Phage Selection

Random mutagenesis libraries and FIND® libraries were cloned into the SfiI and NotI sites of the phagemid pFAB75 (Johansen et al., 1995) and transformed into *E. coli* TOP10 F' (Invitrogen) for expression on phage particles. Phage stocks were prepared according to standard protocols, using VSCM13 (Stratagene) as helper phage (Cicortas Gunnarsson et al., 2004). Positive selections were performed on a biotinylated C5aR peptide with sulfated tyrosines consisting of amino acids 7-28 (biotin-C5aR peptide) (AnaSpec, San José, Calif.) at a final concentration of $10^{-7}$ M and streptavidin-coated magnetic Dynabeads (Invitrogen). The mixture was incubated for 1 hour on rotation at room temperature, followed by extensive washing in PBS 0.05% Tween 20 with 1% bovine serum albumin (BSA) (selection buffer). Elution of peptide binders was performed with 1M Glycine 0.1% BSA, pH 2.2, followed by addition of 1M Tris pH 9.0 to neutralize the eluate. The selection protocol was then repeated once as described above. Directly after the second round of positive selection, CHIPS phage stocks were subjected to a round of negative selection for human anti-CHIPS$_{31-113}$ IgG binding. Estapor 0.83 µm magnetic beads (Bangs-Laboratories Inc., Fishers, Ind.) coated with human anti-CHIPS$_{31-113}$ IgG were washed three times in selection buffer and then blocked in selection buffer for 1 hour on rotation at room temperature. The eluate from the positive selection was added to the beads and they were incubated for another 15 minutes at room temperature. After separation on a magnet, the supernatant was saved and used for infection of exponentially growing *E. coli* TOP10 F' and phagemids were purified from the *E. coli*.

ELISA

ELISA was used for screening and characterization of binding throughout the study. Maxisorb clear or white 96 or 384 well plates (Nunc, Roskilde, Denmark) were coated overnight at 4° C. with the specific protein or antibody in PBS. Incubations were carried out in a volume of 100 or 25 µl for 1 hour at room temperature if not described differently, always followed by washing three times with PBS 0.05% Tween 20. SuperSignal® ELISA Pico Chemiluminescent Substrate (Pierce, Rockford, Ill.) was used and luminescence was measured.

Analysis of Protein Expression

For quantification of expressed proteins, plates were coated with 3 µg/ml monoclonal anti-CHIPS antibody 2H7 recognizing a peptide of CHIPS amino acids 24-30 (Haas et al., 2004). Plates were blocked in PBS 0.05% Tween 20 with 3% milk powder, washed and incubated with dilutions of lysates from the ΔC CHIPS variants. Binding was detected with 3 µg/ml polyclonal rabbit anti-CHIPS N-terminal IgG (IgG produced by immunization of a rabbit with a KLH-coupled synthetic peptide corresponding to CHIPS N-terminal amino acids 1-14) and horseradish peroxidase (HRP) conjugated goat anti-rabbit IgG (Southern Biotech, Birmingham, Ala.).

Analysis of Anti-CHIPS IgG Binding

For detection of binding of human anti-CHIPS$_{31-113}$ IgG to CHIPS AC variants, plates were coated, blocked and incubated with *E. coli* lysates as described for analysis of protein expression. Affinity purified human anti-CHIPS$_{31-113}$ IgG was added and binding was detected with goat-anti-human IgG HRP (Jackson ImmunoResearch, West Grove, Pa.). During initial screenings, single point measurements were performed on the CHIPS lysates and were compared to a titration curve of Wt CHIPS$_{1-121}$. Results were correlated to the results from the expression ELISA. Full titration curves were made for a limited number of variants in later screenings/characterizations.

Analysis of Peptide Binding

In order to measure the binding of CHIPS variants towards the C5aR peptide, 5 µg/ml Streptavidin (Sigma-Aldrich) was coated. Furthermore, the biotin-C5aR peptide (Anaspec) was added to a final concentration of 0.3 µg/ml after washing and blocking the plates (2% BSA in PBS 0.05% Tween 20). Plates were then incubated with CHIPS lysates and detection was performed with 1 µg/ml mAb 2H7 and HRP-conjugated rabbit anti-mouse IgG (Dako, Glostrup, Denmark).

Analysis of Anti-CHIPS IgG Binding in Competition with CHIPS$_{1-121}$

Five-fold dilution series of the CHIPS variants were pre-incubated with 60 ng/ml affinity purified human anti-CHIPS$_{31-113}$ polyclonal IgG in a polypropylene plate (Nunc) for 2 hours at room temperature. Purified wt CHIPS$_{1-121}$ was coated in the ELISA plate. After blocking with 4% BSA in PBS-0.05% Tween-20, the IgG/CHIPS variant mixtures were added to the plate and further incubated for 2 hours at room temperature. Detection was performed with goat-anti-human IgG HRP and o-phenylenediamine dihydrochloride (OPD) substrate.

Analysis of Serum IgG Binding

IgG from human pooled serum was tested for reactivity with CHIPS variants in ELISA. The plate was coated with equimolar amounts of the proteins or PBS. After blocking in PBS-0.05% Tween-20 with 3% milk powder, serially diluted human serum was added. IgG binding to CHIPS variants was detected with rabbit anti-human IgG-HRP (Dako). The IgG titre reported was calculated by plotting the luminescence data against the dilution factor followed by analysis in a non linear curve fitting model. The titre was reported as the dilution factor of serum at which a cut-off value was reached. This cut-off value was set by coating wildtype CHIPS1-121 and analyzing binding of IgG in pooled human serum of different dilutions. The signal generated by serum diluted 1/40,000 was set as a cut-off value, since IgG binding to CHIPS1-121 at this dilution was shown to be in the dynamic interval of the binding curve.

Biological Assays

Binding to the Human C5aR

Human neutrophils were prepared from buffy coats obtained from Lund University Hospital (Lund, Sweden) The buffy coats were diluted 1/1 (v/v) with PBS with 2% new born calf serum (NBS) (Lonza), and added on top of Ficoll Paque plus (GE Healthcare, Uppsala, Sweden). neutrophils were collected and in PBS after centrifugation at 1000×g for 30 minutes. Then, erythrocytes were lysed by incubation with ice-cold H$_2$O for 30 seconds and 4×PBS was added and the suspension was centrifuged at 600×g 4° C. for 7 minutes. Neutrophils were collected in PBS with 2% NBS and remaining erythrocytes were lysed by incubation with ice-cold H$_2$O for 30 seconds and 4×PBS was added. Neutrophils were collected by centrifugation at 1000×g 4° C. for 5 minutes.

Binding to the human C5aR was studied on human neutrophils as well as on the stably transfected cell line U937/C5aR, a generous gift from Dr. E. Prossnitz (University of New Mexico, Albuquerque, N. Mex.). Cells were grown in 75 cm$^2$ cell culture flasks in a 5% CO$_2$ incubator at 37° C. and were maintained in RPMI 1640 medium with L-glutamine (Lonza) and 10% fetal bovine serum (FBS) (Lonza, Basel, Switzerland). Binding to the C5aR was analyzed in two ways by flow cytometry. In the first method, dilution series of ΔC CHIPS variants (expressed by the Expressway Cell-Free E. coli Expression System from Invitrogen) were incubated with cells and CHIPS binding was detected by the 2H7 monoclonal anti-CHIPS antibody, followed by a R-phycoerythrin (RPE) labeled goat anti-mouse immunoglobulin (Dako). In the second method, CHIPS ΔC variants were incubated with cells as above, then the degree of inhibition of binding was quantified by adding a monoclonal anti-C5aR antibody and the RPE-labeled goat anti-mouse immunoglobulin to the cells.

C5aR Blocking

C5a induced calcium mobilization in human neutrophils was studied by flow cytometry. 5×10$^6$/ml neutrophils were incubated with 2 µM Fluo-3AM (Sigma-Aldrich) in RPMI 1640 medium with 0.05% BSA for 30 min at room temperature (RT), followed by washing and resuspension in RPMI 1640 with 0.05% BSA. Cells were then preincubated with a 3-fold dilution series of purified CHIPS variants (re-cloned into the ΔN/C format) at room temperature for 30 min and C5a (Sigma-Aldrich) (final concentration 0.3 nM) was added to induce calcium release. This was measured by means of fluorescence on a FACScalibur flow cytometer (BD Biosciences, San José, Calif.).

C5a induced migration of human neutrophils (chemotaxis) was measured in a transwell system (Neuro Probe, Gaithersburg, Md.). Therefore 5×10$^6$/ml human neutrophils were labelled with 4 µM Calcein-AM (Sigma-Aldrich), washed in Hank's balanced salt solution (HBSS) with 1% human serum albumin (HSA) and resuspended in HBSS with 1% HSA. Cells were further incubated for 15 minutes at RT with a titration of purified CHIPS ΔN/C variants. C5a was added to the lower compartment of the wells to a final concentration of 1 nM. Labelled cells were added to the upper compartments. Plates were incubated for 30 minutes at 37° C. with 5% CO$_2$. Then filters were rinsed with PBS to remove non-migrating cells and fluorescence was measured at an excitation of 485 nm and emission of 530 nm in a fluorescence plate reader. The data were fitted in a non-linear regression model (sigmoidal dose response curve 0-100 with variable slope).

Thermal Denaturation by Circular Dichroism (CD) Spectroscopy

The CD signal at 212 nm was monitored during thermal unfolding of the CHIPS variants from 4-85° C. at a scan rate of 1° C./min, response of 16 s and bandwidth of 1 nm. The protein concentration was 0.5 mg/ml in PBS pH 7.2 and a quartz cuvette with 1 mm pathlength was used. To investigate the reversibility, a thermal scan from 85-4° C. was monitored after the upward scan. Structural changes were determined from far-UV CD spectra, at 4 or 85° C., before and after each thermal scan. Spectra were recorded between 250-195 nm, the scan rate was 20 nm/min, the response 8 s and the bandwidth 1 nm. All CD spectroscopy was carried out on a Jasco (Jasco Inc., Easton, Md.) J-720 spectropolarimeter with a JASCO PTC-343 Peltier type thermostated cell holder. Since the thermal unfolding was irreversible for all variants no thermodynamic stability could be obtained. However, since unfolding was monitored at the same speed for all variants the $T_m$ gives comparative thermal stabilities between the variants. The $T_m$ was obtained by fitting eq. 1 to CD data.

$$\varepsilon_{obs} = \frac{(k_N \cdot T + b_N) + (k_U \cdot T + b_U) \cdot}{e^{-(A(1-(T/T_m)) \div 3000(T-T_m-T \cdot \ln(T/T_m)))/RT}} \quad (eq. 1)$$
$$\varepsilon_{obs} = \frac{e^{-(A(1-(T/T_m)) \div 3000(T-T_m-T \cdot \ln(T/T_m)))/RT}}{(1 + e^{-(A(1-(T/T_m)) \div 3000(T-T_m-T \cdot \ln(T/T_m)))/RT})}$$

In eq. 1, $\varepsilon_{obs}$ is the observed ellipticity at 212 nm, $k_N$, $b_N$, $k_U$ and $b_U$ define the baselines of the native and unfolded states respectively. A is a parameter in the fitting process but has no value for an irreversible unfolding, T is the temperature in Kelvin and R is the gas constant. In the equation, the protein is assumed to follow a two-state denaturation process and have a constant $\Delta C°_p$ in the temperature region so that the denaturation follows Gibbs-Helmholtz equation. For such an unfolding the parameter A is $\Delta H°$ and 3000 is an estimated measure for $\Delta C°_p$ but these parameters have no relevance for an irreversible unfolding.

Molecular Modelling

Modelling was performed by the use of the available CHIPS$_{31-121}$ NMR structure (PDB code: 1XEE) (Haas et al., 2005) and the PyMol molecular graphics program (DeLano, 2008).

Results

Strategy to Create CHIPS Variants with Low IgG Binding

The evolution for decreased anti-CHIPS IgG interaction, yet preserved C5aR blocking activity was performed in one round of random mutagenesis and three rounds of FIND® recombination, followed by computational analysis and rational design (FIG. 14). A shorter CHIPS variant, truncated at both the N- and C-terminus (CHIPS ΔN/C) and comprising single mutants K61A, K69A and K100A previously shown to be less prone to bind human anti-CHIPS IgG (data not shown), was chosen as starting material for the optimization process. The first 30 N-terminal amino acids in CHIPS were kept as a recognition sequence (which was not subjected to mutagenesis or recombinations) for capture antibodies in ELISA. Selected clones were then re-cloned into the truncated (CHIPS ΔN/C) format before characterization of biological activity (C5aR inhibition).

In order to increase the probability to find new CHIPS variants with decreased IgG binding, several different ELISAs were applied for studying the interaction between CHIPS and affinity purified anti-CHIPS$_{31-113}$ IgG. Several screening rounds were performed in ELISA for each of the libraries in Rounds 1, 3 and 4. The primary screening of each round was performed by one-point measurements, whereas the assays were performed more comprehensively in later rounds of screening by making full titration curves for each of the selected mutants.

Furthermore, to preserve the biological functionality of the new CHIPS variants during selections and screening, binding to a peptide of the C5aR N-terminal amino acids 7-28 with sulfated tyrosines was continuously monitored. Residues 10-18 of the C5aR have previously been shown to be the binding domain for CHIPS (Postma et al., 2005). Tyrosines 11 and 14 of the C5aR have been shown to be sulfated, which was shown to be critical for C5a dependent activation of the C5aR (Farzan et al., 2001). A recent study on CHIPS binding to peptides of the C5aR N-terminus stresses the role for sulfated tyrosines in positions 11 and 14 for CHIPS binding and shows that CHIPS binds with high affinity to sulfated peptides of the C5aR N-terminus (Ippel et al., 2009).

Random Mutagenesis Libraries and Screening

Diversity was introduced into the CHIPS ΔC sequence by random mutagenesis. Four libraries with different mutation frequencies were created (details of the libraries are described in Table 3). All four libraries were subjected to phage selection; first for C5aR peptide binding (positive selection), followed by selection for decreased anti-CHIPS IgG binding (negative selection). Supernatants from the negative selection were pooled, allowed to infect E. coli and phagemids were purified. The CHIPS encoding sequences from the pool of mutants were re-cloned into the expression vector pRSET B and 360 CHIPS variants were subsequently expressed in plate format and screened in ELISA for decreased anti-CHIPS$_{31-113}$ IgG binding (FIG. 15A). The clones showed on average 70% anti-CHIPS$_{31-113}$ IgG binding as compared to wt CHIPS$_{1-121}$. The most improved clone showed 53% binding.

The 64 clones with lowest anti-CHIPS$_{31-113}$ IgG binding were further analyzed for retained C5aR peptide binding in ELISA. The average value of C5aR peptide binding was 80% binding as compared to wt CHIPS$_{1-121}$. The 30 clones with the highest C5aR peptide binding were selected for further analysis of decreased anti-CHIPS$_{31-113}$ IgG binding by making full titration curves in ELISA. Finally, 9 clones with significantly reduced anti-CHIPS$_{31-113}$ IgG binding, yet retained C5aR peptide binding were selected for DNA recombination by FIND®.

FIND® Libraries and Screening

FIND® Round 1

Two libraries with different recombination frequencies (i.e. different numbers of cross-overs) were created from the 9 clones (containing in total 18 amino acid substitutions) selected in the random mutagenesis step (Table 3). Library 2.1 was designed by FIND® with a short randomized oligonucleotide added to the reaction. This oligonucleotide was corresponding to amino acids 100-112 and was added to increase the number of mutations in the C-terminal end of CHIPS. Library 2.2 was designed by FIND® under error-prone conditions to increase the number of new mutations in the entire CHIPS sequence.

The libraries were subjected to phage selection as described above and supernatants from the negative selection were pooled, and phagemids were purified from E. coli. This pool of DNA was used as starting material for the second round of FIND®.

FIND® Round 2

In the second round of FIND®, one library (Library 3.1) was created (see Table 3). $6.3 \times 10^3$ clones were expressed in plate format and screened in ELISA for both interaction with anti-CHIPS$_{31-113}$ IgG and C5aR peptide. The average binding to the C5aR peptide was 92% of wt CHIPS$_{1-121}$ binding. The 320 clones that showed maximum 70% of wt CHIPS$_{1-121}$ binding to the anti-CHIPS$_{31-113}$ IgG and at least 80% of wt CHIPS$_{1-121}$ binding to the C5aR peptide were selected for a second round of ELISA-screening for lower anti-CHIPS$_{31-113}$ IgG binding. The response was correlated to expression levels by analysis in a separate ELISA. The most improved clone showed 13% anti-CHIPS$_{31-113}$ IgG binding as compared to wt CHIPS$_{1-121}$, and the average value among the clones was 39% binding (FIG. 15 A).

Of these, 40 clones showed <40% binding compared to wt CHIPS$_{1-121}$ and were then further analyzed in a dose-dependent set up in ELISA. The EC$_{50}$ value (i.e. the concentration of each CHIPS variant mediating half-maximal binding) and plateau value of each variant were determined and compared to the values of wt CHIPS$_{1-121}$. The 12 clones that were improved compared to the best clone from the random mutagenesis round were selected for a last round of FIND® recombination. These clones showed at least 2.4 higher EC$_{50}$ and a maximum of 54% of wt CHIPS$_{1-121}$ plateau value in anti-CHIPS$_{31-113}$ IgG binding.

FIND® Round 3

Two libraries were created in the final round of FIND®. The first library was based on six of the selected clones with 14 amino acid changes represented (Library 4.1) and the second library was made from all 12 clones selected during the previous round of FIND® (in total 25 amino acid changes) (Library 4.2). Both libraries were designed by the use of two repeated rounds of FIND® without any selection or screening in between, which generated a higher frequency of recombined clones (92%) than in the previous libraries (Table 3).

$9.6 \times 10^3$ clones were expressed in plate format and screened in ELISA for decreased human anti-CHIPS$_{31-113}$ IgG binding. 1000 clones showed maximum 10% of wt CHIPS$_{1-121}$ binding to anti-CHIPS$_{31-113}$ IgG and were further analyzed for C5aR peptide binding in ELISA. The mean value of C5aR peptide binding was 45% of wt $CHIPS_{1-121}$ binding. The 96 clones that showed at least 95% binding to the C5aR peptide as compared to wt $CHIPS_{1-121}$ (FIG. 15A), were selected for further analysis in ELISA for decreased anti-$CHIPS_{31-113}$ IgG binding and in flow cytometry for retained C5aR binding. The clones showed on average 7.1% binding of anti-$CHIPS_{31-113}$ IgG as compared to wt $CHIPS_{1-121}$. The most improved clone showed 2.5% binding as compared to wt $CHIPS_{1-121}$ (FIG. 15B). The distribution of the 96 clones is shown in FIG. 15 C.

After sequencing, 42 unique clones were identified. All 42 clones showed <10% binding to the anti-$CHIPS_{31-113}$ IgG as compared to wt $CHIPS_{1-121}$ after the last round of screening. These clones were expressed by a cell-free protein expression system to improve the yield of protein and the products were characterized further by ELISA and flow cytometry. During this thorough characterization, a small number of clones showed higher binding towards the anti-$CHIPS_{31-113}$ IgG than measured during the previous screening, hence the cut-off value was set to 13% instead of the previous 10%. The 10 clones showing the highest binding to the human C5aR as well as low binding to anti-$CHIPS_{31-113}$ IgG (<13% of wt $CHIPS_{1-121}$) (FIG. 16), were selected for further mutagenesis. These clones are shown in table 5.

Molecular Modelling and Rational Design

To decrease the interaction with anti-$CHIPS_{31-113}$ IgG even further, 27 new CHIPS variants were created by site-directed mutagenesis of four of the 10 selected clones (Table 5 and 6). By introducing new mutations into these specific clones, all 12 mutated positions identified during directed evolution were represented. The site-directed mutagenesis was designed by analyzing the protein structure, with special attention paid to the structural role of the mutated amino acid residues generated during the directed evolution. New substitutions were suggested in some of these, mutated positions and these were also joined in new combinations compared to the clones generated during directed evolution.

Characterization of CHIPS Variants

The mutants were first analyzed by ELISA for binding to the C5aR peptide. The clones that showed at least 90% binding to the peptide were selected for further analyses. In subsequent binding experiments performed with human neutrophils, clone S3.09 with alanine in position 112 was found to display improved binding to the C5aR (105 of wt $CHIPS_{1-121}$ binding) compared to the corresponding clone with valine in this position (F3.08; 84% of wt $CHIPS_{1-121}$ binding). For this reason, V112 was substituted to an alanine in position 112 in most of the selected clones. In addition, the clones were recloned into the ΔN/C format and were subsequently purified from inclusion bodies through extensive washing of the inclusion bodies, solubilization, refolding (dropwise addition of the protein solution into PBS) and gel filtration as described previously (Gustafsson et al., 2009). The 16 clones that showed the highest C5aR blocking activity (blocking of $Ca^{2+}$ release after C5a stimulation) in flow cytometry experiments on U937/C5aR cells were selected for further characterizations. After analyzing CHIPS binding to serum IgG by ELISA and biological functionality (C5aR blocking activity) by flow cytometry on human neutrophils, 7 clones could finally be selected as the most promising candidates (see Supplementary table III). This choice was based on the following criteria: Serum IgG titer at a maximum of 2.3% and C5aR blocking activity (in neutrophils) of at least 50%, of that observed for wt $CHIPS_{1-121}$. These clones were further characterized by studying inhibition of neutrophil migration (chemotaxis) and by determining $T_m$ values by CD spectroscopy (Table 4). The temperature denaturations show that all clones have a high melting temperature compared to CHIPS ΔN/C. Some variants show a minor transition at a low temperature and a major transition at a high temperature, indicating partial unfolding at the low temperature. CHIPS ΔN/C shows a reversible unfolding while all seven clones show an irreversible thermal unfolding. This suggests a higher aggregation propensity of the clones in the unfolded state compared to wt $CHIPS_{1-121}$ and CHIPS ΔN/C. The theoretical pl values of the seven clones are given in Table 6. These values are slightly higher than the pl of wt $CHIPS_{1-121}$ (pl of 9.36), hence wt $CHIPS_{1-121}$ and the seven variants carry a net positive charge at a pH lower than 9.36.

FIG. 17 shows a sequence alignment of the top seven clones. The clones contain between five and eight mutations per sequence. Three mutated positions are located in the α-helix, one in the loop between the $\beta_1$ and $\beta_2$ strands, two in the loop between the $\beta_2$ and $\beta_3$ strands, one in β strand 3, one in the loop between the $\beta_3$ and $\beta_4$ strands and two in β strand 4. More specifically, positions K40, D42, N77, K100, N111 and G112 are mutated in four or more clones in different combinations with mutations in positions K50, K69, K92 and K105. Substitutions N77Y, N111K and G112A are the most common among the clones, represented in six out of seven clones, respectively.

Out of the seven clones, one variant (376) was identified as the most interesting and selected to be further characterized in future studies. FIG. 18 shows a surface representation of clone 376 with the mutations marked in green. Although this candidate does not have the lowest IgG titer among the top seven clones, it has a titer that is decreased almost 180 times compared to wt $CHIPS_{1-121}$. The highly preserved ability of this mutant to block C5aR signalling and inhibit C5a induced chemotaxis was considered to be of greater importance.

Discussion

Although a certain characteristic of a protein can be of interest for drug development, other properties might need to be improved in order to design a promising drug candidate. Today, there are a number of drugs (approved or in clinical phase trials) that have been optimized by the use of protein engineering. Tissue plasminogen activator (t-PA) has been improved several times to finally have a longer half-life in serum as well as higher specificity for fibrin (Keyt et al., 1994). This engineered version of tPA (TNKase®) is now approved for the treatment of acute myocardial infarction. ANYARA is a superantigen coupled antibody with tumor specificity, currently in clinical trials. The antigenicity of the superantigen staphylococcal enterotoxin A, SEA, has been decreased to make ANYARA a more attractive anti-tumor drug candidate (Erlandsson et al., 2003).

In combination with a well designed screening method, directed evolution can be utilized to improve almost any characteristic of a protein, i.e. improved affinity, higher potency or decreased immunogenicity. However, when improving a specific property of interest, it is important to continuously monitor other significant characteristics of the protein that might also be altered during the optimization of the specific property.

In this study, we were able to decrease the interaction between CHIPS variants and human IgG to only 0.5% of wt $CHIPS_{1-121}$ while still keeping the C5aR blocking activity. This was achieved by continuously monitoring the C5aR binding during the rounds of directed evolution and screening to ensure that this property was not lost during the optimization process. Moreover, to increase the probability to find new CHIPS variants with decreased IgG binding, several methods for verifying this property were applied during the rounds of screening.

Directed evolution (random mutagenesis and FIND®) was applied in combination with computational/rational design to improve the CHIPS molecule towards lower interaction with specific human IgG. Diversity was first introduced into the sequence by random mutagenesis, followed by three rounds of FIND® performed sequentially with selection and/or screening after each round. Without need for prior knowledge of the epitopes for pre-existing IgG in CHIPS, the mutations found to be beneficial in the previous round were recombined to form new CHIPS variants and IgG binding was shown to decrease with every round. After the last round of FIND®, the best clones displayed a binding of human anti-$CHIPS_{31-113}$ IgG that was reduced to only 2.5% of the binding towards wt $CHIPS_{1-121}$. This was a significant decrease in binding achieved by the application of directed evolution. However, to decrease the binding even further, site-directed mutagenesis was designed by molecular modelling and additional mutations were introduced. The most improved final clone showed 0.5% of the IgG binding observed for wt $CHIPS_{1-121}$. This was accomplished by analyzing the structural distribution of the positions found to be of importance in the directed evolution process.

The combination of mutations in the top seven clones is responsible for the unique properties of these variants. In an attempt to investigate the contribution of the different mutated residues, a structural analysis of the most frequently mutated positions among the final seven clones; D42, N77, N111 and G112 was applied. D42 is an amino acid in the α-helix that seems to be important for intramolecular interactions. Substitution to a valine (V) potentially breaks the H—H bond formed between D42 and R46. This change may alter the structure of the CHIPS molecule and possibly also change an IgG epitope. The introduction of the hydrophobic valine at position 42 seems to increase the stability of the molecule. Most likely, this hydrophobic residue fits well into the interior of the structure and stabilizes the hydrophobic core and that may be the reason why it is represented in six out of the seven selected clones. However, the mutation might affect the reversibility and the aggregation propensity in the unfolded state due to increased hydrophobicity. N77, is mutated to a tyrosine (Y) in six of the clones and to a histidine (H) in one clone. It is exposed in the β2-β3 loop and could be directly involved in IgG binding. When comparing N77Y and N77H it appears that the tyrosine increases the stability compared to the histidine in this position. On the other hand clone 376, with a histidine in this position, has a better preserved biological function (inhibition of chemotaxis) as compared to clone 335 that is identical apart from a tyrosine in position 77. N111 is an exposed residue in β4. This position becomes more positively charged upon substitution to lysine (K), which is a significant change of the surface that was shown to be beneficial in six out of the seven clones. G112 in β4 is not particularly exposed. A small amino acid was found to be advantageous in this position. If a large amino acid, such as valine, is inserted in this position, it might collide with M93, and as a result the structure may be affected. Changing the G112V mutation, selected during directed evolution, to an alanine (A) was found to be beneficial for preserving C5aR blocking activity in all clones carrying the G112V mutation. Interestingly, three of the seven top clones (variants 335, 338 and 377) were the same as clones found during directed evolution, but with a substitution to A in position 112 instead of V.

Among the final seven clones, four out of 12 lysines are mutated to arginines. Arginine substitutions of the lysines in position 92 and 105 are found in three of the clones and in position 100 in four of the clones. There may be several explanations to why the four lysines have been substituted by arginines. The substitution from lysine to arginine can arise from only one base change and arginine has many similar properties to lysine, while several of the other amino acids, possible to achieve through one base change, are more different from lysine and therefore fit onto the surface of the protein with more difficulty. Arginines might stabilize the protein and are generally common in binding surfaces. In the CHIPS variants, arginines may contribute to the preserved C5aR binding.

The approach to combine random mutagenesis or directed evolution with computational/rational design has also been successfully applied by others (Buskirk et al., 2004). For example, mutagenesis can first been utilized to provide information on residues important to mutate. This way, mutagenesis can be directed from a randomized point of view instead of being based on rational choices (Lingen et al., 2002).

Our results demonstrate that epitopes for human IgG can be efficiently reduced in a protein of bacterial origin by the use of directed evolution and computational/rational design.

The removal of antibody epitopes is relevant in several disciplines within immunology. In allergy research, IgE epitopes are removed to create hypoallergenic allergen derivatives to be used as candidate vaccines (Linhart et al., 2008; Mothes-Luksch et al., 2008; Szalai et al., 2008; Vrtala et al., 2004). This work has been performed mainly by epitope mapping and subsequent genetic engineering or by the design of mosaic proteins or hybrid molecules, but there are also studies where hypoallergens have been created by the use of directed evolution. In a recent study (Gafvelin et al., 2007), directed evolution by multi-gene recombination to three group 2 mite allergen genes generated hypoallergen candidates with reduced IgE reactivity and preserved T-cell reactivity.

In conclusion, by the use of directed evolution, computational analysis and rational design we have generated new CHIPS molecules with decreased interaction with pre-existing specific human IgG without affecting the interaction between CHIPS and the C5aR to a high extent. This work has resulted in CHIPS variants that are better suited to therapeutic use than the wt $CHIPS_{1-121}$ protein, because of a significantly reduced tendency to form complexes with pre-existing human IgG, and thereby better tolerated and functionally more efficient than the wt $CHIPS_{1-121}$ protein as C5aR antagonists.

Out of these, one variant (376) was identified having unexpectedly advantageous properties. This clone was designated ADC-1004.

REFERENCES

Buskirk, A. R., Landrigan, A. and Liu, D. R. (2004)*Chem Biol*, 11, 1157-1163.

Cicortas Gunnarsson, L., Nordberg Karlsson,E., Albrekt, A. S., Andersson, M., Holst, O. and Ohlin, M. (2004) *Protein Eng Des Sel*, 17, 213-221.
Dahlen, E., et al. (2008) *J Immunotoxicol*, 5, 189-199.
De Haas, C. J., Veldkamp, K. E., Peschel, A., Weerkamp, F., Van Wamel, W. J., Heezius, E. C., Poppelier, M. J., Van Kessel, K. P. and Van Strijp, J. A. (2004) *J Exp Med*, 199, 687-695.
DeLano, W. L. (2008) The PyMOL Molecular Graphics System. Delano Scientific LLC, Palo Alto, Calif.
Erlandsson, E., et al. (2003) *J Mol Biol*, 333, 893-905.
Farzan, M., Schnitzler, C. E., Vasilieva, N., Leung, D., Kuhn, J., Gerard, C., Gerard, N. P. and Choe, H. (2001) *J Exp Med*, 193, 1059-1066.
Gafvelin, G., Parmley, S., Neimert-Andersson, T., Blank, U., Eriksson, T. L., van Hage, M. and Punnonen, J. (2007) *J Biol Chem*, 282, 3778-3787.
Gustafsson, E., Forsberg, C., Haraldsson, K., Lindman, S., Ljung, L. and Furebring, C. (2009) *Protein Expr Puff*, 63, 95-101.
Haas, P. J., de Haas, C. J., Kleibeuker, W., Poppelier, M. J., van Kessel, K. P., Kruijtzer, J. A., Liskamp, R. M. and van Strijp, J. A. (2004) *J Immunol*, 173, 5704-5711.
Haas, P. J., et al. (2005) *J Mol Biol*, 353, 859-872.
Heller, T., et al. (1999) *J Immunol*, 163, 985-994.
Ippel, J. H., de Haas, C. J., Bunschoten, A., van Strijp, J. A., Kruijtzer, J. A., Liskamp, R. M. and Kemmink, J. (2009) *J Biol Chem*. doi:10.1074/jbc.M808179200.
Johannes, T. W. and Zhao, H. (2006) *Curr Opin Microbiol*, 9, 261-267.
Johansen, L. K., Albrechtsen, B., Andersen, H. W. and Engberg, J. (1995) *Protein Eng*, 8, 1063-1067.
Keyt, B. A., et al. (1994) *Proc Natl Acad Sci USA*, 91, 3670-3674.
Knecht, W., et al. (2006) *Febs J*, 273, 778-792.
Leung, D. W., Chen, E. and Goeddel, D. V. (1989) *Technique*, 11-15.
Lingen, B., Grotzinger, J., Kolter, D., Kula, M. R. and Pohl, M. (2002) *Protein Eng*, 15, 585-593.
Linhart, B., Mothes-Luksch, N., Vrtala, S., Kneidinger, M., Valent, P. and Valenta, R. (2008) *Biol Chem*, 389, 925-933.
Mothes-Luksch, N., et al. (2008) *J Immunol*, 181, 4864-4873.
Postma, B., Kleibeuker, W., Poppelier, M. J., Boonstra, M., van Kessel, K. P., van Strijp, J. A. and de Haas, C. J. (2005) *J Biol. Chem*.
Postma, B., Poppelier, M. J., van Galen, J. C., Prossnitz, E. R., van Strijp, J. A., de Haas, C. J. and van Kessel, K. P. (2004) *J Immunol*, 172, 6994-7001.
Reetz, M. T. (2004) *Proc Natl Acad Sci USA*, 101, 5716-5722.
Rittirsch, D., et al. (2008) *Nat Med*, 14, 551-557.
Sneeden, J. and Loeb, L. (2003) Random oligonucleotide mutagenesis. In Arnold, F. and Georgiou, G. (eds.), *Directed evolution library creation. Methods and protocols*. Humana Press, Totowa, N.J., Vol. 231, pp. 65-73.
Stemmer, W. P. (1994a) *Proc Natl Acad Sci USA*, 91, 10747-10751.
Stemmer, W. P. (1994b) *Nature*, 370, 389-391.
Szalai, K., et al. (2008) *Mol Immunol*, 45, 1308-1317.
Wong, T. S., Roccatano, D. and Schwaneberg, U. (2007) *Environ Microbiol*, 9, 2645-2659.
Wright, A. J., Higginbottom, A., Philippe, D., Upadhyay, A., Bagby, S., Read, R. C., Monk, P. N. and Partridge, L. J. (2007) *Mol Immunol*, 44, 2507-2517.
Vrtala, S., Focke-Tejkl, M., Swoboda, I., Kraft, D. and Valenta, R. (2004) *Methods*, 32, 313-320.
Yuan, L., Kurek, I., English, J. and Keenan, R. (2005) *Microbiol Mol Biol Rev*, 69, 373-392.
Zhao, H. (2007) *Biotechnol Bioeng*, 98, 313-317.
Zhao, H., Giver, L., Shao, Z., Affholter, J. A. and Arnold, F. H. (1998) *Nat Biotechnol*, 16, 258-261.

TABLE 3

Library characteristics

| Round | Library[1] | Mutations in starting material[2] | New mutations/ clone[2] | Frequency recombined sequences (%) | Number of recombinations/ recombined clone | Frequency unique sequences (%) | Library size (clones) |
|---|---|---|---|---|---|---|---|
| 1 (Random mutagenesis) | 1.1 | (3) | 6.3 (3.6) | N/A[4] | N/A[4] | N/D[3] | $2 \times 10^6$ |
| | 1.2 | (3) | 2.2 (1.5) | N/A[4] | N/A[4] | N/D[3] | $2 \times 10^6$ |
| | 1.3 | (3) | 3.1 (2.5) | N/A[4] | N/A[4] | 90 | $2 \times 10^6$ |
| | 1.4 | (3) | 1.4 (1.1) | N/A[4] | N/A[4] | 100 | $2 \times 10^6$ |
| 2 (FIND ® round 1) | 2.1 | 26 (18) | 0.2 | 28 | 1.4 | 81 | $2 \times 10^5$ |
| | 2.2 | 26 (18) | 2.4 | 48 | 1.6 | 97 | $7 \times 10^5$ |
| 3 (FIND ® round 2) | 3.1 | N/D[3] | N/A[4] | 58 | 1.6 | 88 | $5 \times 10^3$ |
| 4 (FIND ® round 3) | 4.1 | 19 (14) | N/A[4] | 92 | 1.7 | 96 | $5 \times 10^3$ |
| | 4.2 | 36 (25) | N/A[4] | 92 | 1.8 | 96 | $1 \times 10^4$ |

[1]Sequence analysis was performed on 24 clones from each library.
[2]Mutations shown as base changes with amino acid changes in brackets.
[3]N/D Not determined
[4]N/A Not applicable

TABLE 4

Characteristics of the final seven clones in comparison to wt CHIPS$_{1-121}$ and CHIPS ΔN/C.

| Clone | Inhibition of $Ca^{2+}$ release in human neutrophils | Chemotaxis $IC_{50}$ (nM) | 95% confidence interval chemotaxis $IC_{50}$ (nM) | IgG titer | Theoretical isoelectric point (pI) | $T_m$ (°C.) | Comments on temperature denaturation |
|---|---|---|---|---|---|---|---|
| Wt CHIPS$_{1-121}$ | ++++ | 8.2 | 6.7-10 | 33667 | 9.36 | 60.5[1] | one transition, reversibility not determined |

TABLE 4-continued

Characteristics of the final seven clones in comparison to wt CHIPS$_{1-121}$ and CHIPS ΔN/C.

| Clone | Inhibition of Ca$^{2+}$ release in human neutrophils | Chemotaxis IC$_{50}$ (nM) | 95% confidence interval chemotaxis IC$_{50}$ (nM) | IgG titer | Theoretical isoelectric point (pI) | T$_m$ (° C.) | Comments on temperature denaturation |
|---|---|---|---|---|---|---|---|
| CHIPS ΔN/C | +++ | 51 | 38-68 | 1826 | 9.70 | 60.1 ± 0.4 | one transition, reversible |
| 332 | ++(+) | 796 | 568-1120 | 694 | 9.67 | 75.7 ± 1.8 | one transition, irreversible |
| 335 | ++(+) | 205 | 118-355 | 611 | 9.74 | 83.9 ± 0.6 | one transition, irreversible |
| 336 | ++(+) | 839 | 297-2370 | 382 | 9.85 | 81.2 ± 0.6 | one transition, irreversible |
| 338 | +(+) | 270 | 233-313 | 179 | 9.67 | 28.2 ± 1.8; 87.0 ± 1.3 | two transitions, irreversible |
| 376 | ++(+) | 49 | 39-60 | 196 | 9.78 | 64.4 ± 0.2 | one transition, irreversible |
| 377 | ++ | 244 | 158-377 | 210 | 9.71 | 30.0 ± 2.8; 85.7 ± 0.8 | two transitions, irreversible |
| 441 | ++(+) | 528 | 316-885 | 784 | 9.67 | 30.2 ± 3.5; 60.2 ± 0.1 | two transitions, irreversible |

[1]Data from one separate experiment, in which both wavelength and temperature were scanned

SUPPLEMENTARY TABLE III

Characterization of site-directed mutants and clones selected after FIND ® recombinations. The final seven selected clones are marked in bold.

| Clone origin | Introduced mutations | Alternative clone name | Inhibition of Ca$^{2+}$ release in U937/C5aR cells | Inhibition of Ca$^{2+}$ release in human neutrophils | IgG titer |
|---|---|---|---|---|---|
| CHIPS$_{1-121}$ | — | — | ++++ | ++++ | 33667 |
| CHIPS ΔN/C | — | — | +++ | +++ | 1826 |
| S3.02 | 112A | 332 | +(+) | ++(+) | 694 |
| S3.09 | 112A | 335 | ++ | ++(+) | 611 |
| S3.21 | 112A | 336 | +++ | ++(+) | 382 |
| S3.04 | 112A | 376 | +++ | ++(+) | 196 |
| F3.85 | — | 441 | +++ | ++(+) | 784 |
| F3.46 | 112A | 377 | ++ | ++ | 210 |
| F3.39 | 112A | 338 | +(+) | +(+) | 179 |
| S3.06 | 112A | 334 | +(+) | +(+) | 434 |
| S4.01 | 112A | 382 | ++ | + | 127 |
| S4.02 | 112A | 383 | ++ | + | 124 |
| S4.04 | 112A | 385 | ++ | + | 293 |
| F3.50 | 112A | 374 | + | N/D | 230 |
| F3.57 | 112A | 375 | + | N/D | 464 |
| S3.05 | 112A | 333 | +(+) | N/D[1] | 494 |
| S3.17 | 112A | 378 | + | N/D | 338 |
| S3.20 | 112A | 380 | + | N/D | 435 |
| S3.22 | 112A | 337 | + | N/A[2] | N/A |
| S3.17 | 112A | 381 | + | N/A | N/A |
| S4.03 | 112A | 384 | + | N/A | N/A |
| F3.85 | 112A | 442 | + | N/A | N/A |
| S3.20 | — | 443 | + | N/A | N/A |
| S4.01 | 112V | 444 | + | N/A | N/A |

[1]Not determined
[2]Not applicable

TABLE 5

Mutations in 10 selected clones after the fourth round of diversification and screening

| Clone | K40 | D42 | K50 | K69 | N77 | D83 | L90 | K92 | K100 | K105 | N111 | G112 |
|---|---|---|---|---|---|---|---|---|---|---|---|---|
| F3.03 | . | . | N | R | Y | . | . | R | . | . | K | V |
| F3.08 | E | V | . | . | Y | . | . | . | R | R | K | V |
| F3.14 | . | . | N | . | Y | . | . | R | . | . | K | V |
| F3.39 | E | V | . | . | Y | . | . | . | . | . | K | V |
| F3.46 | E | V | . | . | Y | . | . | R | . | . | K | V |
| F3.50 | . | . | N | . | Y | . | . | . | . | . | K | V |
| F3.57 | E | V | N | . | Y | . | . | R | . | . | K | V |
| F3.70 | N | . | N | . | Y | . | . | R | . | . | I | . |
| F3.71 | N | . | . | . | Y | G | P | . | . | . | K | V |
| F3.85 | . | . | N | . | Y | . | . | R | R | . | I | . |

TABLE 6

Site-directed mutations made in four of the clones selected after FIND ® recombinations

| Clone | K40 | D42 | K50 | N68 | K69 | N77 | D83 | L90 | K92 | K100 | K105 | N111 | G112 |
|---|---|---|---|---|---|---|---|---|---|---|---|---|---|
| F3.08 | E | V | . | . | . | Y | . | . | . | R | R | K | V |
| S3.01 | . | . | E | . | . | . | . | . | . | . | . | . | . |
| S3.02 | . | . | . | . | A | . | . | . | . | . | . | . | . |
| S3.03 | . | . | . | . | T | . | . | . | . | . | . | . | . |
| S3.04 | . | . | . | . | . | H | . | . | . | . | . | . | . |
| S3.05 | . | . | . | . | . | . | H | . | . | . | . | . | . |
| S3.06 | . | . | . | . | . | . | . | E | . | . | . | . | . |
| S3.07 | . | . | . | . | . | . | . | . | E | . | . | . | . |
| S3.08 | . | . | . | . | . | . | . | . | . | A | . | . | . |
| S3.09 | . | . | . | . | . | . | . | . | . | . | . | . | A |
| S3.10 | . | . | E | . | . | . | . | . | R | . | . | . | . |
| S3.11 | . | . | . | . | . | . | . | . | . | . | . | N | . |
| S3.12 | . | . | . | . | . | . | . | . | . | . | . | . | G |
| S3.13 | . | . | . | H | . | . | . | . | . | . | . | . | . |
| F3.71 | N | . | . | . | . | Y | G | P | . | . | . | K | V |
| S3.14 | . | . | . | H | . | . | . | . | . | . | . | . | . |
| S3.23 | . | V | . | . | . | . | . | . | . | . | . | . | . |
| S4.01 | . | V | . | . | . | . | . | . | . | . | . | . | A |
| S4.02 | . | V | . | . | . | N | . | . | . | . | . | . | . |
| S4.03 | . | V | . | . | . | . | . | E | . | . | . | . | . |
| S4.04 | . | V | . | . | . | N | E | . | . | . | . | . | . |
| F3.03 | . | . | N | . | R | Y | . | . | R | . | . | K | V |
| S3.15 | . | . | . | H | . | . | . | . | . | . | . | . | . |
| S3.16 | . | . | . | . | . | . | . | . | . | A | . | . | . |
| S3.17 | . | . | . | . | . | A | . | . | . | . | . | . | . |
| S3.18 | . | . | . | . | . | A | . | . | . | A | . | . | . |
| S3.20 | E | . | . | . | . | . | . | . | . | . | . | . | . |
| S3.21 | . | V | . | . | . | . | . | . | . | . | . | . | . |
| S3.22 | E | V | . | . | . | . | . | . | . | . | . | . | . |
| F3.70 | N | . | N | . | . | Y | . | . | R | . | . | I | . |
| S3.19 | . | . | . | . | . | . | . | . | . | . | . | K | . |

EXAMPLE C

CHIPS Variant ADC-1004 is a Potent C5AR Antagonist Displaying Low Interaction with IgG from Human Serum CHIPS is encountered by a majority of the human population early in life since *Staphylococcus aureus* is a common bacterium and the CHIPS gene is present in over 60% of *S. aureus* strains. Consequently, circulating anti-CHIPS antibodies that interfere with CHIPS binding to the C5aR have been detected in human serum (Wright et al., 2007*, Mol Immunol* 44:2507). Circulating antibodies may neutralize the biological effect of proteins. Such neutralizing antibodies may affect the efficacy of drugs, like the presence of anti-IFN-β antibodies in MS patients (Bertolotto et al., 2000, *Immunopharmacology* 48:95). Furthermore, circulating specific antibodies may form immune complexes (ICs) with the protein. Immune complexes are known to cause disease if deposited in blood vessels or organs, e.g. the kidney. In addition, IC mediated activation of the classical complement pathway leads to leukocyte activation and subsequent tissue damage. Therefore, the potential of CHIPS to function as an anti-inflammatory molecule is hampered by the specific antibodies.

Besides reacting with pre-existing antibodies, a recombinant protein administered to humans can potentially induce a new $T_H$-cell dependent immune response. It can be difficult to predict whether recombinant or foreign proteins administered to humans are likely to induce a $T_H$-cell dependent antibody response; e.g. animal models are not always applicable for human responses. However, T-cell epitope algorithms have been developed for evaluation of candidate biopharmaceutical $T_H$-cell epitope content (De Groot et al., 2001, *Vaccine* 19:4385; Desmet, Spriet & Lasters, 2002, *Proteins* 48:31; Desmet et al., 2005, *Proteins* 58:53). Recent data confirm that these models can be utilized to predict human antibody responses (Koren et al., 2007, *Clin Immunol* 124:26).

The N-terminal amino acids of CHIPS were previously shown to be essential for FPR binding (Haas et al., 2005, *J Mol Biol* 353:859). As a result, N-terminal truncation will specify the CHIPS activity towards C5aR binding. To design a molecule with specific C5aR blocking activity and low interaction with human antibodies, a directed evolution approach was employed. The new improved CHIPS variant could be discovered by the use of DNA recombination, molecular modelling, site-directed mutagenesis and rounds of screening for decreased specific antibody interaction as well as preserved C5aR binding (see Example B above). In this study, we characterized the properties of the new CHIPS variant, called ADC-1004, with respect to interaction with IgG from human serum, complement activation, C5aR inhibition, immune complex formation and T-cell epitope content in different assays to evaluate the feasibility of using this protein as a pharmaceutical. Our data demonstrate that the IgG binding of a protein can be significantly decreased, while still retaining its biological function. ADC-1004 is indeed a protein with potent antagonistic activity towards the C5aR. Pre-existing human antibodies display very weak interaction with ADC-1004 and we speculate that an immediate response to neutralize ADC-1004 would most probably not occur in humans. Also, we show that ADC-1004 does not induce any of the antibody mediated effects to the same extent as full-length $CHIPS_{1-121}$ when compared in different in vitro models.

Materials & Methods

Cloning, Expression and Purification of Recombinant Proteins

Wild-type $CHIPS_{1-121}$ was cloned, expressed and purified as described earlier (10). $CHIPS_{31-113}$ and ADC-1004 were created by truncation and mutagenesis (manuscript in preparation). These CHIPS variants were then cloned and cultivated as described above, but were purified from inclusion bodies. Briefly, 100 ml *E. coli* culture was pelleted and the pellets were frozen overnight at −20° C. Inclusion bodies were purified by washing in three different buffers; buffer 1:50 mM Tris pH 8.0, 1 mM EDTA, 25% Sucrose, buffer 2: mM Tris pH 8.0, 0.2M NaCl, 0.5% Sodium Deoxycholate, 2 mM EDTA, and buffer 3:10 mM Tris pH 8.0, 0.25% Sodium Deoxycholate, 1 mM EDTA. The pellet was dissolved, sonicated on ice and incubated with shaking at RT for 30 min in each buffer. Inclusion bodies were then pelleted by centrifugation at 12,000 rpm after each round of washing. Purified inclusion bodies were solubilized in 50 mM Tris-HCl, 0.2 M NaCl, 2 mM EDTA, 7 M GuHCl pH 8.0 and refolded by rapid dilution into PBS (final protein concentration max 100 μg/ml) and incubated with rotation at RT o/n. Then, after concentration on AmiconUltra spin filters (Millipore, Billerica, Mass.), the proteins were further purified by gel filtration on a HiLoad® 16/60 Superdex® 75 (spherical composite of cross-linked agarose and dextran) prep grade column (GE Healthcare, Uppsala, Sweden). Protein concentrations were determined by QuantiPro BCA assay kit (Sigma Aldrich, St Louis, Mo.).

Isolation of Human Neutrophils

Human neutrophils were prepared from buffy coats obtained from Lund University Hospital (Lund, Sweden), by Percoll (Sigma-Aldrich) density gradient centrifugation. Remaining erythrocytes were lysed with ice-cold $H_2O$ for 30 s. Cells were finally collected in RPMI-1640/0.05% BSA.

Cell Culture

U937 cells (human promonocytic cell line) transfected with the C5aR (U937/C5aR) were a generous gift from Dr. E. Prossnitz (University of New Mexico, Albuquerque, N. Mex.). Cells were grown in 75 $cm^2$ cell culture flasks in a 5% $CO_2$ incubator at 37° C. and were maintained in RPMI 1640 medium with L-glutamine (Cambrex, Verviers, Belgium) and 10% FBS (Cambrex, Verviers, Belgium).

Interaction with Human Serum

Human pooled serum or sera from 128, 28 and 127 healthy individuals (3H Biomedical, Uppsala, Sweden) was tested for reactivity with $CHIPS_{1-121}$, $CHIPS_{31-113}$, ADC-1004, respectively in ELISA. Human pooled serum was also tested for binding to Streptokinase (Aventis-Behring, King of Prussia, Pa.) and Anakinra (Amgen Inc., Thousand Oaks, Calif.). The plate was coated with equimolar amounts of the proteins or PBS. Serially diluted human serum was added and allowed to bind. IgG binding to CHIPS variants were detected with a HRP conjugated rabbit anti-human IgG (Dako A/S, Glostrup, Denmark), followed by development with Super Signal ELISA Pico Chemiluminescent Substrate (Pierce, Rockford, Ill.). Serum diluted 1/40 000 binding to coated $CHIPS_{1-121}$ was used to regenerate a cut-off value. The luminescence was measured and plotted against the dilution factor and analysed in a non linear curve fitting model to calculate the dilution at which cut-off was reached, which was reported as the titer.

Complement Deposition

Complement deposition mediated by interaction between anti-CHIPS antibodies from human serum and CHIPS variants was studied in ELISA. Plates were coated with equimolar amounts of $CHIPS_{1-121}$, $CHIPS_{31-113}$, ADC-1004 or PBS, and incubated with human serum. Complement deposition was quantified with a mouse anti-human C3c antibody (Quidel, San Diego, Calif.) and a HRP conjugated anti-mouse Ig (Dako A/S) followed by addition of Super Signal ELISA Pico Chemiluminescent Substrate. Luminescence was measured and plotted against the serum concentration.

Biological Activity Assays

C5a induced chemotaxis of neutrophils was measured in a ChemoTx® transwell system with a filter size of 8.0 μm (Neuro Probe, Gaithersburg, Md.). $5\times10^6$/ml human neutrophils were labelled with 4 μM Calcein-AM (Sigma Aldrich) for 20 minutes at RT under gentle agitation, washed once in HBSS with 1% HSA and the cells were resuspended to $2.5\times10^6$/ml in HBSS with 1% HSA. Cells were further incubated for 15 minutes at RT with a titration of CHIPS variants. C5a (Sigma Aldrich) as added to the lower compartment of the wells to a final concentration of 1 nM. The upper wells were assembled and labelled cells were added to the upper compartments. Labelled cells were added to the lower compartment in control wells to represent total count. The plate was incubated for 30 minutes at 37° C. with 5% $CO_2$. Then the filters were rinsed with PBS to remove non-migrating cells and fluorescence was measured at an excitation of 485 nm and emission of 530 nm. Results are presented as % inhibition of chemotaxis as compared to cells without addition of CHIPS.

Purified CHIPS variants were tested for their ability to inhibit the C5a induced calcium mobilization in human neutrophils. Briefly, $5 \times 10^6$/ml neutrophils were incubated with 2 µM Fluo-3AM (Sigma Aldrich) in RPMI 1640 medium with 0.05% BSA for 30 min at room temperature, washed twice and resuspended in RPMI 1640 medium with 0.05% BSA to a concentration of $10^6$ cells/ml. Cells were preincubated with a 3-fold dilution series of CHIPS variants at room temperature for 30 min. Basal fluorescence level was measured on each sample for ~10 s before C5a (Sigma Aldrich) (final concentration 3 nM) was added and the sample quickly placed back in the sample holder to continue measurement in a FACScalibur flow cytometer (BD Biosciences, San José, Calif.). Samples were analyzed after gating the cell population on forward and side scatter. Results are expressed as percentage inhibition of cells without addition of CHIPS.

T-Cell Epitope Analysis

CHIPS variants were analyzed for T-cell epitope content using the Epibase® system (Desmet, Spriet & Lasters, 2002, *Proteins* 48:31; Desmet et al., 2005, *Proteins* 58:53) according to patent EP 1 226 528.

Molecular Modelling

Modelling was performed by the use of the available $CHIPS_{31-121}$ NMR structure (PDB code: 1XEE) (18) and the PyMol molecular graphics program (DeLano, 2002, The PyMol Molecular Graphics System. Delano Scientific, San Carlos).

Results

ADC-1004

ADC-1004 is a new CHIPS variant, based upon the $CHIPS_{31-113}$ sequence, with seven amino acid substitutions, namely; K40E, D42V, N77H, K100R, K105R, N111K and G112A. ADC-1004 was discovered by mutagenesis and screening of CHIPS libraries for decreased specific antibody interaction as well as preserved C5aR binding. The $CHIPS_{31-121}$ fold has previously been described to consist of an N-terminal amphipathic α-helix and a four-stranded antiparallel β-sheet as determined by multi-dimensional NMR (18). This model was used to show the structural distribution of the ADC-1004 mutations which contribute to the ADC-1004 characteristics that we have characterized in this study (FIG. 18).

ADC-1004 Shows Low-Level Interaction with IgG in Human Serum

In order to evaluate the usefulness of ADC-1004, its interaction with IgG in human serum was studied in ELISA. The IgG titer towards ADC-1004 was compared to the titers towards $CHIPS_{1-121}$, $CHIPS_{31-113}$, Streptokinase and Anakinra (a recombinant IL-1 receptor antagonist, approved for treatment of rheumatoid arthritis) using human serum from healthy volunteers. The titer for Anakinra was included as a negative control since no titer could be detected towards this molecule. The ADC-1004 antibody titer was shown to be significantly lower than the titers of $CHIPS_{1-121}$ (172 times lower), $CHIPS_{31-113}$ (9 times lower) and Streptokinase (15 times lower). (FIG. 19 A). Furthermore, analysis of the titer of individual sera showed that a significantly higher number of individuals are responsive towards $CHIPS_{1-121}$ and $CHIPS_{31-113}$ than to ADC-1004 (FIG. 19 B). The individuals giving the highest IgG response towards $CHIPS_{1-121}$ are also the highest responders towards $CHIPS_{31-113}$ and ADC-1004.

ADC-1004 Induces Low-Level Antibody-Dependent Complement Activation

Antibodies in the circulation can interfere with the action of recombinant proteins in many ways. Besides the neutralizing effect of the anti-CHIPS antibodies, the interaction between CHIPS and antibodies could potentially activate the complement cascade. Such an activation might lead to unwanted effects such as leukocyte activation and resulting tissue damage.

To study complement activation, CHIPS variants were coated in ELISA plates and incubated with serial dilutions of human serum and deposition of complement fragment C3c was quantified. In accordance with the results from the serum IgG interaction experiments presented above, ADC-1004 mediated the lowest C3c deposition. At 10% serum, ADC-1004 mediated C3c deposition was shown to be six times lower than that induced by $CHIPS_{1-121}$ and three times lower than $CHIPS_{31-113}$ induced C3c deposition (FIG. 20 A). In addition, analysis of sera from 28 individuals also showed a significantly lower C3c deposition upon incubation with ADC-1004 as compared to $CHIPS_{1-121}$ and $CHIPS_{31-113}$ at 10% serum (FIG. 20 B).

ADC-1004 Inhibits C5a Induced Neutrophil Activation and Migration

CHIPS inhibits C5a dependent neutrophil activation and migration by blocking the C5aR. To investigate whether ADC-1004 was functional in inhibiting C5a induced chemotaxis and activation, this CHIPS variant was compared to $CHIPS_{1-121}$ and $CHIPS_{31-113}$ in two assays.

First, C5aR signalling inhibition was investigated by measuring the mobilization of intracellular calcium by flow cytometry. Serial dilutions of the CHIPS variants were preincubated with Fluo-3 labeled neutrophils and the cells were stimulated with C5a. The flow cytometry data show that the concentration needed for 50% inhibition of calcium release ($IC_{50}$) of ADC-1004 was 0.4 nM±0.12, which is a mean value calculated from three independent experiments. The mean value was the same as the $IC_{50}$ of $CHIPS_{31-113}$ and twice that of the $IC_{50}$ of $CHIPS_{1-121}$. A representative example is shown in FIG. 21A. Second, neutrophil migration was studied in a transwell system where serial dilutions of the CHIPS variants were preincubated with Calcein labeled neutrophils in the upper compartment of the transwell. The labeled neutrophils were then allowed to migrate towards a C5a gradient over the membrane to the lower compartment. The results show that the $IC_{50}$ of ADC-1004 was the same as the $IC_{50}$ of $CHIPS_{31-113}$ and approximately four times higher than the $IC_{50}$ of $CHIPS_{1-121}$ (FIG. 21B).

ADC-1004 T-Cell Epitope Content

T-cell epitopes are peptides of a protein that are needed to ensure $T_H$-cell activation. The T-cell epitope content of ADC-1004 was compared to that of wild-type full-length CHIPS ($CHIPS_{1-121}$) in an in silico model (Epibase®; (Desmet, Spriet & Lasters, 2002, *Proteins* 48:31; Desmet et al, 2005, *Proteins* 58:53)) to estimate the probability of ADC-1004 inducing a new $T_H$-cell dependent antibody response. Table 7 shows that the total number of predicted epitopes is lower in ADC-1004 than in $CHIPS_{1-121}$. Moreover, the predicted epitopes in ADC-1004 are different and less promiscuous than those found in $CHIPS_{1-121}$ (data not shown).

Discussion

Complement fragment C5a is a powerful peptide that exerts proinflammatory effects through the C5aR, a mechanism involved in many inflammatory disorders. The C5aR can thus be considered an important drug target in these diseases (Monk et al., 2007, *Br J Pharmacol.* 152(4):429-48; Ricklin & Lambris, 2007, *Nat Biotechnol* 25:1265). The C5aR antagonist CHIPS is one of the proteins produced by the human pathogen *S. aureus* to evade the host response by modulating the innate immune system (De Haas et al., 2004, *Agent. J Exp Med* 199:687; Lee at al., 2004, *J Infect Dis*

190:571; Rooijakkers et al., 2005, *Nat Immunol* 6:920; Jongerius et al., 2007, *J Exp Med* 204:2461). Antibodies directed against CHIPS have been found in human sera (Wright et al., 2007, *Mol Immunol* 44:2507); hence this protein is not likely to be tolerated by humans and the CHIPS activity in vivo is likely to be neutralized. In essence, CHIPS is a potent C5aR antagonist but with limited use in humans due to pre-existing specific antibodies.

To increase the feasibility to use this protein in vivo, we have created an improved functional unity, called ADC-1004. This CHIPS variant harbours seven amino acid substitutions (see Example B above), which together contribute to the new characteristics of the ADC-1004 protein. Interestingly, despite the high number of mutations that totally alter the interaction with human antibodies, the biological function to inhibit the C5aR is retained. Presumably some of the amino acid substitutions in fact stabilize the CHIPS fold rather than being directly involved in decreasing antibody binding to ADC-1004 (see Example B above).

We have determined the IgG titer towards ADC-1004 compared to titers towards full-length $CHIPS_{1-121}$ and the truncated $CHIPS_{31-113}$ variant as well as to titers towards two existing biopharmaceuticals. For comparison Streptokinase an existing pharmaceutical derived from a bacterial protein was used. Streptokinase is and has been used for treatment of myocardial infarction for more than 30 years (ISIS-2. ISIS-2 (Second International Study of Infarct Survival) Collaborative Group., 1988, Randomised trial of intravenous streptokinase, oral aspirin, both, or neither among 17,187 cases of suspected acute myocardial infarction, *Lancet* 2:349). ADC-1004 showed low interaction with human IgG from human serum, both pooled serum and serum from different individuals. The titer of ADC-1004 was 172 times lower than the full-length $CHIPS_{1-121}$ titer and 15 times lower than for Streptokinase. Also, no individuals were strongly responsive towards ADC-1004, while several individuals showed especially high titers towards full-length $CHIPS_{1-121}$.

This low interaction with human antibodies was shown to be advantageous, since ADC-1004 did not induce antibody mediated effects to the same extent as full-length $CHIPS_{1-121}$ or $CHIPS_{31-113}$. When studying complement activation by immobilizing the CHIPS variants in ELISA and adding serum, ADC-1004 proved to be a poor inducer of complement activation, generating six times lower C3c deposition than full-length $CHIPS_{1-121}$. These data suggest that immune-mediated adverse effects are less likely to be induced upon administration of ADC-1004 than the other CHIPS variants tested.

Remarkably, the introduced mutations did not remove the biological function of ADC-1004. ADC-1004 showed an $IC_{50}$ value equal to that of $CHIPS_{31-113}$ and four times higher than the $IC_{50}$ value of full-length $CHIPS_{1-121}$ in inhibition of C5a induced neutrophil migration. There was an even smaller difference between the CHIPS variants when studying biological activity by the means of inhibition of calcium release in human neutrophils upon C5a stimulation. The mean value of ADC-1004 $IC_{50}$ was the same as the $IC_{50}$ of $CHIPS_{31-113}$ and twice that of full-length $CHIPS_{1-121}$.

Previously anti-CHIPS antibodies, which interfere with CHIPS binding to the C5aR, have been detected in human serum (Wright et al, 2007, *Mol Immunol* 44:2507). Of great importance for functionality in vivo, ADC-1004 was not inhibited by human serum to the same extent as full-length $CHIPS_{1-121}$ as indicated in a calcium release assay (data not shown) when tested on U937 cells stably transfected with the human C5aR. Even though the interaction of ADC-1004 with IgG in human serum was undetectable when studied in ELISA, some low affinity epitopes might still be present in the protein and could be the explanation for the serum effect seen when ADC-1004 was studied in the calcium release model. Also, other Ig classes could be involved in the human response towards CHIPS. We have looked at the IgM response towards the different CHIPS variants and it is always 3-20 times lower than the IgG response.

ADC-1004 displays very weak interaction with pre-existing human IgG. However, there are other aspects of immunogenicity to take into consideration. It is also important to evaluate if it is prone to induce a $T_H$-cell dependent immune response, like many recombinant or non-human proteins are. Foreign epitopes within a protein or the lack of glycosylation leading to the exposure of hidden epitopes as well as presence of aggregates due to suboptimal formulation are some of the causes of immunogenicity seen in biopharmaceuticals (Schellekens, 2003, *Nephrol Dial Transplant* 18:1257). However, T-cell epitopes within a recombinant protein are more important to take into consideration if the protein is going to be developed for treatment of chronic disorders, i.e. if it is to be administered more than once to the same patient. ADC-1004 is a small protein and would probably be most beneficial in the treatment of acute inflammations, since it is likely to have a short half-life in circulation due to its small size. To verify that the T-cell dependent immunogenicity of ADC-1004 was not increased as compared to the full-length $CHIPS_{1-121}$, we estimated the T-cell epitope content of the CHIPS variants in an in silico model. ADC-1004 was shown to contain a moderate number of potential T-cell epitopes (in total 11 strong $T_H$ epitopes), lower than that of $CHIPS_{1-121}$ and comparable to that of other proteins studied previously in this model (Van Walle et al., 2007, *Expert opinion on biological therapy* 7:405). For example, the chimeric antibody Rituximab approved for treatment of non-Hodgkin's lymphoma and RA was shown to contain in total 22 strong $T_H$ epitopes and the human antibody Ofatumumab currently in clinical trials was shown to contain in total six strong $T_H$ epitopes. It is also important to take into consideration that several epitopes differ between $CHIPS_{1-121}$ and ADC-1004. Therefore, a strong T-cell memory response is less likely to occur upon administration of ADC-1004 than $CHIPS_{1-121}$, since the pre-existing memory T-cells are geared towards the epitopes found in $CHIPS_{1-121}$. Any T-cell responses against ADC-1004 will therefore be classical, non-memory based responses. The combined approach of avoiding pre-existing antibodies, hence B-cell epitope removal, with $T_H$-cell memory avoidance, is consistent with ADC-1004 being significantly less immunogenic that the wild-type CHIPS protein.

In conclusion, our work with CHIPS shows that the interaction of a protein with antibodies in human serum can be significantly decreased, while still retaining the biological function of the protein.

REFERENCES

1. Guo, R. F., and P. A. Ward. 2005. Role of C5a in inflammatory responses. *Annu Rev Immuno/*23:821.
2. Wetsel, R. A. 1995. Expression of the complement C5a anaphylatoxin receptor (C5aR) on non-myeloid cells. *Immunol Lett* 44:183.
3. Zwimer, J., A. Fayyazi, and O. Gotze. 1999. Expression of the anaphylatoxin C5a receptor in non-myeloid cells. *Mol Immunol* 36:877.
4. Okusawa, S., K. B. Yancey, J. W. van der Meer, S. Endres, G. Lonnemann, K. Hefter, M. M. Frank, J. F. Burke, C. A. Dinarello, and J. A. Gelfand. 1988. C5a stimulates secretion of tumor necrosis factor from human mononuclear cells in vitro. Comparison with secretion of interleukin 1 beta and interleukin 1 alpha. *J Exp Med* 168:443.
5. Kohl, J. 2001. Anaphylatoxins and infectious and non-infectious inflammatory diseases. *Mol Immunol* 38:175.
6. Barnum, S. R. 2002. Complement in central nervous system inflammation. *Immunol Res* 26:7.
7. Monk, P. N., A. M. Scola, P. Madala, and D. P. Fairlie. 2007. Function, structure and therapeutic potential of complement C5a receptors. *Br J. Pharmacol.*
8. Ricklin, D., and J. D. Lambris. 2007. Complement-targeted therapeutics. *Nat Biotechnol* 25:1265.
9. Sumichika, H. 2004. C5a receptor antagonists for the treatment of inflammation. *Curr Opin Investig Drugs* 5:505.
10. De Haas, C. J., K. E. Veldkamp, A. Peschel, F. Weerkamp, W. J. Van Wamel, E. C. Heezius, M. J. Poppelier, K. P. Van Kessel, and J. A. Van Strijp. 2004. Chemotaxis Inhibitory Protein of Staphylococcus aureus, a Bacterial Antiinflammatory Agent. *J Exp Med* 199:687.
11. Postma, B., M. J. Poppelier, J. C. van Galen, E. R. Prossnitz, J. A. van Strijp, C. J. de Haas, and K. P. van Kessel. 2004. Chemotaxis inhibitory protein of Staphylococcus aureus binds specifically to the C5a and formylated peptide receptor. *J Immunol* 172:6994.
12. Wright, A. J., A. Higginbottom, D. Philippe, A. Upadhyay, S. Bagby, R. C. Read, P. N. Monk, and L. J. Partridge. 2007. Characterisation of receptor binding by the chemotaxis inhibitory protein of Staphylococcus aureus and the effects of the host immune response. *Mol Immunol* 44:2507.
13. Bertolotto, A., S. Malucchi, E. Milano, A. Castello, M. Capobianco, and R. Mutani. 2000. Interferon beta neutralizing antibodies in multiple sclerosis: neutralizing activity and cross-reactivity with three different preparations. *Immunopharmacology* 48:95.
14. De Groot, A. S., A. Bosma, N. Chinai, J. Frost, B. M. Jesdale, M. A. Gonzalez, W. Martin, and C. Saint-Aubin. 2001. From genome to vaccine: in silico predictions, ex vivo verification. *Vaccine* 19:4385.
15. Desmet, J., J. Spriet, and I. Lasters. 2002. Fast and accurate side-chain topology and energy refinement (FASTER) as a new method for protein structure optimization. *Proteins* 48:31.
16. Desmet, J., G. Meersseman, N. Boutonnet, J. Pletinckx, K. De Clercq, M. Debulpaep, T. Braeckman, and I. Lasters. 2005. Anchor profiles of HLA-specific peptides: analysis by a novel affinity scoring method and experimental validation. *Proteins* 58:53.
17. Koren, E., A. S. De Groot, V. Jawa, K. D. Beck, T. Boone, D. Rivera, L. Li, D. Mytych, M. Koscec, D. Weeraratne, S. Swanson, and W. Martin. 2007. Clinical validation of the "in silico" prediction of immunogenicity of a human recombinant therapeutic protein. *Clin Immunol* 124:26.
18. Haas, P. J., C. J. de Haas, M. J. Poppelier, K. P. van Kessel, J. A. van Strijp, K. Dijkstra, R. M. Scheek, H. Fan, J. A. Kruijtzer, R. M. Liskamp, and J. Kemmink. 2005. The structure of the C5a receptor-blocking domain of chemotaxis inhibitory protein of Staphylococcus aureus is related to a group of immune evasive molecules. *J Mol Biol* 353: 859.
19. DeLano, W. L. 2002. The PyMol Molecular Graphics System. Delano Scientific, San Carlos.
20. Lee, L. Y., M. Hook, D. Haviland, R. A. Wetsel, E. O. Yonter, P. Syribeys, J. Vernachio, and E. L. Brown. 2004. Inhibition of complement activation by a secreted Staphylococcus aureus protein. *J Infect Dis* 190:571.
21. Rooijakkers, S. H., M. Ruyken, A. Roos, M. R. Daha, J. S. Presanis, R. B. Sim, W. J. van Wamel, K. P. van Kessel, and J. A. van Strijp. 2005. Immune evasion by a staphylococcal complement inhibitor that acts on C3 convertases. *Nat Immunol* 6:920.
22. Jongerius, I., J. Kohl, M. K. Pandey, M. Ruyken, K. P. van Kessel, J. A. van Strijp, and S. H. Rooijakkers. 2007. Staphylococcal complement evasion by various convertase-blocking molecules. *J Exp Med* 204:2461.
23. 1988. Randomised trial of intravenous streptokinase, oral aspirin, both, or neither among 17,187 cases of suspected acute myocardial infarction: ISIS-2. ISIS-2 (Second International Study of Infarct Survival) Collaborative Group. *Lancet* 2:349.
24. Schellekens, H. 2003. Immunogenicity of therapeutic proteins. Nephrol Dial *Transplant* 18:1257.
25. Van Walle, I., Y. Gansemans, P. W. H. I. Parren, P. Stas, and I. Lasters. 2007. Immunogenicity screening in protein drug development. *Expert opinion on biological therapy* 7:405.

TABLE 7

$T_H$ epitope counts for $CHIPS_{1-121}$ and ADC-1004. Peptides binding to multiple HLAs of the same group (DRB1, DRB3/4/5, DP, DQ) are counted as one

| | DRB1 | | | | |
| --- | --- | --- | --- | --- | --- |
| | Strong | Medium | DRB3/4/5 | DQ | DP |
| $CHIPS_{1-121}$ | 9 | 23 | 2 | 1 | 2 |
| ADC-1004 | 7 | 19 | 2 | 1 | 1 |

EXAMPLE D

In VIVO Study of the Efficacy of Chips Variant ADC-1004 In the Treatment of Acute Myocardial Infarction and Reperfusion Injury Introduction A percutaneous catheter-based approach was chosen in order to induce ischemia with minimum trauma, operation-induced stress and secondary changes in circulatory physiology. Myocardial infarct size was chosen as the primary effect parameter since, in the clinical setting, the long term outcome is heavily dependant on the infarct size [1]. Reduction of myocardial infarct size is also the aim of reperfusion therapy. Reperfusion therapy that achieves a good macroscopic result after opening of the coronary occlusion may yet result in persistent ST-segment elevation attributed to microvascular injury [2]. The degree of microvascular injury is associated with the duration of myocardial ischemia and the extent of myocardial infarction but may possibly also be caused by reperfusion injury. The presence of microvascular obstruction is associated with a worse clinical outcome [3]. MO was therefore chosen as a complementary effect parameter. Ex vivo MRI allows for achievement of high resolution images of the myocardial infarction and correlates closely to histology with TTC-staining [4], and was therefore chosen as the method for IS evaluation. SPECT was used to determine area at risk during ischemia. The presence of microvascular obstruction may have several pathophysiological mechanisms [5]. One of these is a neutrophil induced inflammatory response upon reperfusion. C5aR (CD88) bearing cells in the infarct area can be determined by histology. State of neutrophil activation can be monitored by CD88 and the activation marker CD18 on histology sections. A decrease of activated neutrophils upon ADC-1004 treatment would indicate a reduction in neutrophil inflammatory response.

Materials and Methods
Experimental Preparation 8 healthy domestic male and female 40-50 kg pigs were fasted overnight with free access to water. Premedication was administered with Kataminol (ketamine, Intervet AB Danderyd Sweden) and Rompun (xylazin, Bayer AG, Leverhusen, Germany) 30 minutes prior to the procedure. After induction of anesthesia with thiopental (Pentothal, Abbott, Stockholm, Sweden) 5-25 mg/kg, the animals were orally intubated with cuffed endotracheal tubes. Thereafter, a slow infusion of 1.25 μl/ml fentanyl (Fentanyl, Pharmalink AB, Stockholm, Sweden) in buffered glucose (25 mg/ml) was started at a rate of 1.5 ml/min and adjusted as needed. During balanced anesthesia thiopental (Pentothal, Abbott, Stockholm, Sweden), was titrated against animal requirements with small bolus doses. Mechanical ventilation was established with a Siemens-Elema 900B ventilator in the volume-controlled mode, adjusted in order to obtain normocapnia. Initial settings were: respiratory rate of 15/min, tidal volume of 10 ml/kg and positive end-expiratory pressure of 5 cmH$_2$O. The animals were ventilated with a mixture of dinitrous oxide (70%) and oxygen (30%). The pigs were continuously monitored with electrocardiogram (ECG) and intraarterial blood pressure. Heparin (200 IU/kg) was given intravenously at the start of the catheterization. A 6 F introducer sheath (Onset, Cordis Co. Miami, Fla., USA) was inserted into the surgically exposed left carotid artery upon which a 6 F JL4 Wiseguide™ (Boston Scientific Scimed, Maple Grove, Minn., USA) was inserted into the left main coronary artery. The catheter was used to place a 0.014-inch PT Choice™ guide wire (Boston Scientific Scimed, Maple Grove, Minn., USA) into the distal portion of the LAD. A 3.5×15 mm Maverich™ monovail angioplasty balloon (Boston Scientific Scimed, Maple Grove, Minn., USA) was then positioned in the mid portion of the LAD, immediately distal to the first diagonal branch. All radiological procedures were performed in an experimental catheterization laboratory (Shimadzu Corp., Kyoto, Japan).

Ischemia Protocol

Ischemia was induced by inflation of the angioplasty balloon for 40 min. An angiogram was performed after inflation of the balloon and before deflation of the balloon in order to verify total occlusion of the coronary vessel and correct balloon positioning. After deflation of the balloon a subsequent angiogram was performed to verify restoration of blood flow in the previously occluded artery.

ADC-1004 Delivery Protocol

A single dose of around 4 mg/kg of ADC-1004 in 0.9% NaCl was intravenously administered to eight animals approximately 22 minutes after ischemia induction. Eight (8) animals received saline only. Plasma concentration of ADC-1004 was monitored during the experiment and the targeted plasma concentration was achieved for the four hours and 40 minutes the experiment lasted (using induction of ischemia as t=0).

Ex-vivo Assessment of Area at Risk by SPECT

Single photon emission computed tomography (SPECT) was used to assess the AAR as percent of left ventricular myocardium. Five hundred MBq of 99 mTc-tetrofosmin was administered intravenously 18 minutes before deflation of the angioplasty balloon. Ex-vivo imaging was performed with a dual head camera (Skylight, Philips, Best, the Netherlands) at 32 projections (40 s per projection) with a 64×64 matrix yielding a digital resolution of 5×5×5 mm. Iterative reconstruction using maximum likelihood-expectation maximization (MLEM) was performed with a low-resolution Butterworth filter with a cut-off frequency set to 0.6 of Nyquist and order 5.0. No attenuation or scatter correction was applied. Finally short and long-axis images were reconstructed. The endocardial and epicardial borders of the left ventricle that were manually delineated in the MR images were copied to the co-registered SPECT images. A SPECT defect was defined as a region within the MRI-determined myocardium with counts lower than the 55% of the maximum counts in the myocardium [6].

Infarct Size and Microvascular Obstruction Assessed by Ex vivo MRI

Ex vivo imaging of the heart was undertaken using a 1.5 T Philips Intera CV MR scanner (Philips, Best, the Netherlands) according to a previous described protocol [4, 7]. In brief, a gadolinium-based contrast agent (Dotarem, gadoteric acid, Gothia Medical, Billdal, Sweden) was administered intravenously (0.4 mmol/kg) 30 minutes prior to removal of the heart. The heart was removed 4 hours after initiation of reperfusion. After removal, the heart was immediately rinsed in cold saline and the ventricles were filled with balloons containing deuterated water. Three dimensional acquisition of T1-weighted images (TR=20 ms, TE=3.2 ms, flip angle=70° and 2 averages) yielded a stack of approximately 200 images with an isometric resolution of 0.5 mm covering the entire heart. Images were then acquired using a head coil and the duration of acquisition was typically 45 minutes. The MR images were analyzed using freely available software [8, 9]. The endocardial and epicardial borders of the left ventricular myocardium were manually delineated in short-axis ex vivo images. This defined the volume of left ventricular myocardium (cm3=ml). The infarct size (IS) was first determined as the volume of infarcted myocardium (cm3). The infarct volume was calculated as the product of the slice thickness (cm) and the area of hyperenhanced pixels (cm2) with a signal intensity above the infarction threshold defined as >8 SD above the mean intensity of non-affected remote myocardium. Microvascular obstruction was defined as hypointense regions in the core of the infarction which had signal intensity less than the threshold for infarction. These regions were manually included in the infarct volume. The volume of microvascular obstruction (cm3) was calculated as the difference between the infarct volume before and after manual inclusion of regions of microvascular obstruction. Furthermore, the size of microvascular obstruction was expressed as percent of percent of area at risk. Ultimately, the infarct size was expressed as percent of left ventricular myocardium. Finally, infarct size was expressed as a percentage of the area at risk (IS/AAR) in order to adjust for any difference in area at risk between the groups [10, 11].

Histology

Heart muscle tissue from infarction area of pig #7 and #8 were used in this study. Tissues were fixed in 4% formaldehyde or snap frozen in isopentan chilled on dry ice. The formaldehyde fixed tissue was embedded in paraffin and sectioned at 5 μm, dried at. 37° C. over night and stained according the methods described below. The cryopreserved tissue was sectioned at 8 μm, dried at room temperature over night and stained according to the methods described below.

Staining with CD88, Serotec, MCA 1283T was performed on 5 μm paraffin sections. Samples were de-paraffinized and an antigen retrieval treatment in boric acid (pH8.0) with boiling for 10 minutes and 20 minute cooling at room temperature was performed. Samples were then treated with 1% H2O2 in tap water for 20 min., washed three times in PBS and incubated in 5% normal goat serum in PBS for 30 minutes. Subsequently samples were incubated for 30 min with the primary antibody, mouse anti human CD88, diluted to 1 μg/ml in PBS with 5% normal goat serum. After three times wash with PBS samples were incubated 30 min with Envision mouse (Dako, K4001) again washed twice in PBS and once in Tris-HCl. Finally samples were treated with DAB for 5-10 min and Mayers hematoxylin for 5 seconds before mounted with coverslips.

Staining with CD18, abcam, ab34117 was performed on 8 µm cryosections. Samples were fixed in acetone for 10 min and treated with 1% H2O2 in tap water for 20 min, washed three times in PBS and incubated in 5% normal goat serum in PBS for 30 minutes. Subsequently samples were incubated for 60 min with the primary antibody, mouse anti pig CD18, diluted to 1 µg/ml in PBS with 5% normal goat serum. After three times wash with PBS samples were incubated 30 min with Envision mouse (Dako, K4001) again washed twice in PBS and once in Tris-HCl. Finally samples were treated with DAB for 5-10 min and Mayers hematoxylin for 5 seconds before mounted with coverslips. The slides were microscopically analyzed and with a PC-based image analysis system (Leica Q500, Cambridge, UK) the percentage of positive stained area was calculated.

Results

ADC-1004 was tested in a porcine model for acute myocardial infarction. Ischemia was induced in sixteen animals where, eight pigs received approximately 4 mg/kg ADC-1004 in saline and eight pigs received saline (control group). The animals were treated and tested as described in materials and methods.

Figure 24B:
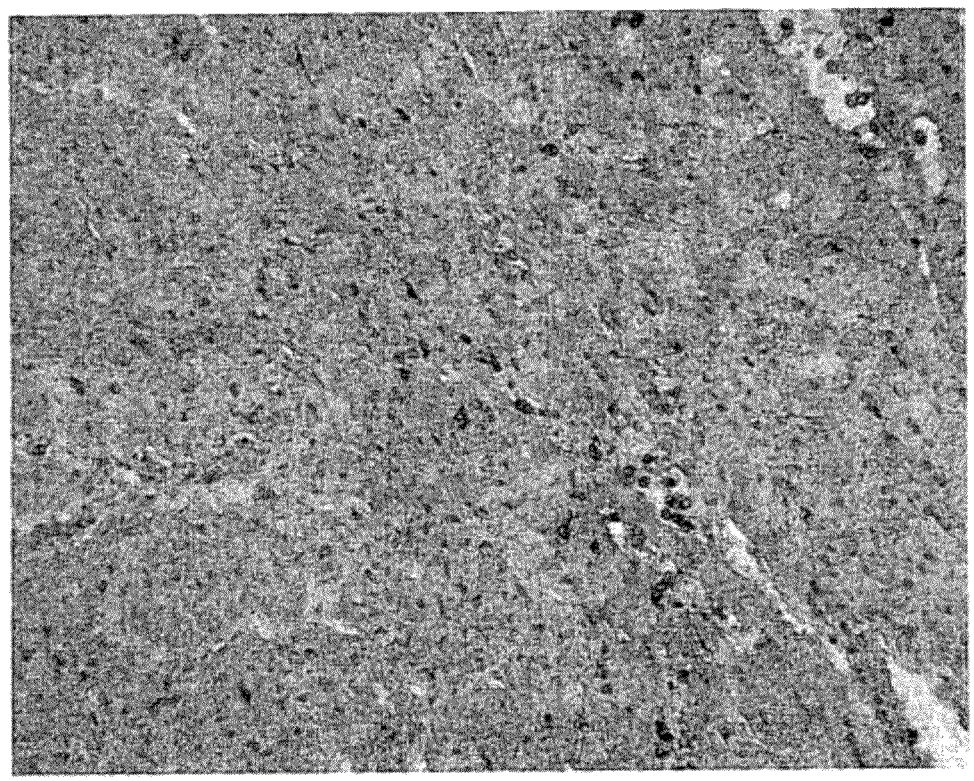

The results shown in FIG. 22 and FIG. 23 shows that the ADC-1004 significantly reduces infarct size in relation to the ischemic area (area at risk) measured by MR/SPECT (p<0.007, Mann-Whitney U-test). This supports a clinical therapeutic effect of ADC-1004 as the long term outcome is heavily dependant on the infarct size [1]. Mean microvascular obstruction was reduced in the group treated with ADC-1004. Microvascular obstruction is a factor which is clinically proven related to the severity of a mycardial infarction [3]. One of the pathophysiological mechanisms behind microvascular obstruction may be neutrophil induced inflammatory response upon reperfusion [5]. Results from histology investigations shows numerous distinct CD88 positive cells are seen in infarction area of both the placebo sections as well as sections from ADC-1004 treatment. The number of positive cells are about 250/mm2 in both cases. Positive cells are found both in blood vessels as well as intermingling with cardiac muscle fibers. CD18 shows a more variable reaction from weakly to strongly positive cells. Placebo samples shows markedly more positive cells (FIG. 24A) compared to ADC-1004 received samples (FIG. 24B). Moreover, more strongly stained cells are seen in placebo compared to treated samples. Measurement with image analysis equipment gives that placebo expresses 2-3 more CD18 compared to ADC-1004 treated indicating reduced activation of neutrophils upon ADC-1004 administration.

Thus, the data presented indicate that acting on the C5aR by administration of ADC-1004 in an acute myocardial infarction (and thereby inhibiting the activation and inflammation by neutrophils) decreases the severity of the infarction.

REFERENCES

1. Fox K A, Dabbous O H, Goldberg R J et al Prediction of risk of death and myocardial infarction in the six months after presentation with acute coronary syndrome: prospective multinational observational study (GRACE). Bmj. 2006, 333:1091.
2. Claeys M J, Bosmans J, Veenstra L et al Determinants and prognostic implications of persistent ST-segment elevation after primary angioplasty for acute myocardial infarction: importance of microvascular reperfusion injury on clinical outcome. Circulation. 1999, 99:1972-1977.
3. Wu K C, Zerhouni E A, Judd R M et al Prognostic significance of microvascular obstruction by magnetic resonance imaging in patients with acute myocardial infarction. Circulation. 1998, 97:765-772.
4. Kim R J, Fieno D S, Parrish T B et al Relationship of MRI delayed contrast enhancement to irreversible injury, infarct age, and contractile function. *Circulation* 1999, 100:1992-2002.
5. Jaffe R, Charron T, Puley G et al Microvascular Obstruction and the No-Reflow Phenomenon After Percutaneous Coronary Intervention. Circulation 2008, 117:3152-3156
6. Ugander M, Soneson H, Heiberg E et al. A novel method for quantifying myocardial perfusion SPECT defect size by co-registration and fusion with MRI—an experimental ex vivo imaging pig heart study. Abstract. Proceedings of the Swedish Heart Association Spring Meeting 2008
7. Götberg M, Olivencrona K G, Engblom H et al Rapid short-duration hypothermia with cold saline and endovascular cooling before reperfusion reduces microvascular obstruction and myocardial infarction size. BMC Cardivascular Disorders 2008, 8:7.
8. Heiberg E, Engblom H, Engvall J et at Semi-automatic quantification of myocardial infarction from delayed contrast enhanced magnetic resonance imaging. *Scand Cardiovasc J* 2005, 39:267-275.
9. Website title [http://segment.heiberg.se/]
10. Hedström E: Acute Myocardial Infarction. The relationship between duration och ischaemia and infarct size in humans—Assessment by MRI and SPECT. In PhD thesis Lund: University of Lund; 2005.
11. Hedstrom E, Frogner F, Astrom-Olsson K et al Myocardial infarct size in relation to myocardium at risk versus duration of ischemia in humans: Comparison with different species (Abstract). *J Cardiovasc Magn Reson* 2007, 9:363

EXAMPLE E

In vivo Study of the Efficacy of Chips Variant ADC-1004 In the Treatment of Stroke and Reperfusion Injury Introduction The aim of this study was to investigate whether treatment with ADC-1004 starting 1 h and 45 min after occlusion of the middle cerebral artery and 15 min prior to reperfusion and with infusion for 24 hrs infusion, would differentially influence the cerebral infarct size in a rat model of transient middle cerebral artery occlusion (tMCAO).

Materials and Methods

Temporary Middle Cerebral Artery Occlusion (tMCAO)

All surgical procedures were approved by the Ethics Committee for Animal Research at Lund University. The male Wistar rats had free access to water and food and were housed under 12 h light/12 h dark cycle. The rats were fasted overnight and subjected to 2 h transient middle cerebral artery occlusion (MCAO) using the intraluminal filament technique. Following the 2 h occlusion, a neurological assessment of deficits was performed after 1.5 hrs of reperfusion. Rats showing rotational asymmetry and dysfunctional limb placement were included. The right middle cerebral artery (MCA) was occluded by the intraluminal filament technique. Animals were anesthetized by inhalation of 4% Forene in O2: N2O (30:70) and then spontaneously ventilating in a nose mask delivering 2% Forene in O2: N2O. For continuous monitoring of blood pressure, control of blood gases and for injection of 60 IU of heparin, a catheter was inserted in the tail artery.

A heating pad connected to a rectal temperature probe was used to guarantee that body temperature was maintained at 37° C. A laser Doppler probe was glued onto right side of the skull, hence monitoring blood flow in the MCA territory. Experimental stroke was induced by first making a skin incision in the middle of the neck to expose the right common carotid artery together with the internal and external part. The external carotid was ligated and the internal carotid was encircled by a suture. In the common carotid artery, a small incision was made close to the bifurcation and a filament was introduced into the internal carotid artery and advanced until it blocked the origin of the middle cerebral artery. The blockade was registered as a decrease in the Laser Doppler signal. After this surgical procedure the rats were allowed to recover from anesthesia during the ischemic period. Reperfusion was performed 2 h later by removal of the filament when the animal once again was anaesthetized.

Prior to reperfusion a silicon catheter was inserted into the vena cava superior and advanced 1-2 cm towards the heart. The catheter was stabilized and tunnelated under the skin of the back of the neck. The catheter was connected to a swivel system that allowed the animal to freely move in a plastic bowl while being injected with either ADC-1004 or placebo (blinded). Fifteen minutes prior to the end of the MCAO the animal was injected with a bolus dose of the solution into the vena cava, followed by a continuous infusion of the solution for 24 hrs. Blood (0.25-0.5 ml) was centrifuged and the plasma frozen for further analysis. Blood was sampled 3, 19, 24 and 48 hrs after reperfusion. In sham-operated animals, identical surgery was performed apart from the insertion of the filament. All physiological parameters of animals included in the study were within normal ranges: pO2>90 mm Hg, pCO2 30-50 mm Hg and pH 7.35-45 as were the arterial blood pressure and rectal temperature during the surgery.

Infarct Evaluation

After 2 days of reperfusion the animals were anesthetized in 4% Forane and decapitated. The brains were quickly removed from the scull and placed in cold saline for 10 minutes. In a tissue slicer, the brains were cut in twelve one millimeter thick coronal slices and the sections were stained in a saline solution containing 1.0% 2,3,5-triphenyltetrazolium chloride (TTC) at 37° C. for 20 minutes. The same procedures were performed for sham-operated animal. The infarct size was assessed by computer assisted image analysis.

Results

ADC-1004 was tested in a rat model for stroke. Rats treated with placebo (saline) had a mean infarct volume of 24.5 mm$^3$ while animals treated with ADC-1004 had a mean infarct size of 15.8 mm$^3$.

These results clearly show a tendency towards smaller infarct size in the ADC-1004 treated animals.

EXAMPLE F

In vivo Study of the Efficacy of Chips Variant ADC-1004 in the Treatment in Lung Transplantation Introduction Obstacles to present day lung transplantation involve (1) lack of suitable donor organs, (2) ischemia/reperfusion (I/R) injury, (3) rejection, and (4) development of bronchiolitis obliterans. Lung I/R injury after transplantation is a common cause of respiratory failure and manifests typically during the first 72 hours post-transplantation.[1] I/R injury continues to be a universal and substantive cause of morbidity and mortality in the early postoperative period, with reported rates as great as 41%.[1] The 30-day mortality of patients with I/R injury is about 40%, compared with 7% in patients without I/R injury.[2] Patients showing I/R injury necessitate prolonged mechanical ventilation with greater hospital stays and are at an increased risk of multiorgan failure. [3]

The mechanisms of I/R injury are diverse and include generation of reactive oxygen species (ROS), leukocyte activation/recruitment, complement and platelet activation, abnormalities in pulmonary vascular tone, and increased procoagulant activity. The production of pro-inflammatory cytokines is increased considerably in the lung after I/R. Several studies suggest that lung I/R injury is characterized by neutrophil dependent injury.[4, 5] Various studies have shown that neutrophil-activating compounds cause lung injury, neutrophil depletion attenuates lung I/R injury, and depletion of neutrophil adhesion prevents lung I/R injury.[6, 7]

ADC-1004 was used in a porcine lung transplantation model modified from ref. 8 investigating the condition of the transplanted lung during the first 6 hours and after 20 hours post transplantation. The arterial oxygen tension was considered as a marker for lung condition.

Materials and Methods

Eight Swedish native breed pigs with a weight of about 66 kg were used (4 donors and 4 recipients). All the animals received humane care in compliance with the "Guide for the Care and Use of Laboratory Animals" published by the National Institute of Health (NIH publication 85-23, revised 1985).

The general experimental set up has previously been described in ref. 8. The procedures are described in brief below:

Donor Procedure

The animals were ventilated with a Siemens Servoventilator 300 and a volume-controlled, pressure-regulated ventilation of 10 l/min (20 breaths/min; positive end-expiratory pressure, 8 cm H2O; inspired oxygen fraction, 0.5-1.0) was used. A sternotomy was performed. After systemic heparinization (4 mg/kg) a 40-cm-long 32F cannula was inserted into the pulmonary artery (PA). The left and right pleural spaces were entered. All parts of the lungs were carefully inspected, and the positive end-expiratory pressure was increased temporarily to 10 cm H2O until the atelectatic parts were eliminated. The abdominal viscera were lifted away from the diaphragm to avoid compressing the lower lobes of the lungs. The superior and inferior venae cavae were ligated. The ascending aorta was clamped. Both the right and left atrium were opened by a cut. The PA was perfused with 1 L of a cold preservation solution, supplemented with ADC-1004 in the treated animals. The mean PA perfusion pressure was kept below 20 mm Hg by keeping the preservation solution level at a height of 20 cm above the lungs. After this procedure, the lungs were removed and stored cold 4° C. for 60 hours.

Recipient Procedure

The recipient pig was sedated and anesthetized. The animal received 1.2 g of intramuscular benzylpenicillinprocain (Ilocillin; Ciba-Geigy, Basel, Switzerland). Tracheostomy was carried out, a No. 7 tracheal tube was inserted, and the animals were ventilated in the same way as the donors. Two central venous catheters were introduced via the internal jugular vein and two catheters were placed in the aorta through the carotid artery. A Foley catheter was inserted into the urinary bladder through a suprapubic cystostomy. A left thoracotomy through the sixth intercostal space was done and a left pneumonectomy performed, care being taken to leave long ends of the pulmonary veins.

The stored left lung from the donor pig was dissected free from the right lung and was subsequently transplanted into the recipient pig. ADC-1004 was given 30 minutes before reperfusion of the transplanted lung. The dose was given both as a bolus dose of 0.4 mg/kg and as an infusion of 0.4 (first treated pig) or 0.2 mg/kg/h (the second treated pig). The pig was placed in a prone position. The infusion of ADC-1004 was continued throughout the experiment. When the blood flow had been established through the transplanted lung, the time was defined as zero. The gas exchange was followed for six hours. Between nineteen and twenty hours after reperfusion a right thoracotomy and a right pneumonectomy were done through the seventh intercostal space and the pig was totally dependent for its survival on the left transplanted lung. Blood gases were then taken before and after the pneumonectomy. The fluid supply during the experimental period was kept constant for all the animals and consisted of 720 mL of 10% glucose (ie, the anaesthetic infusion of 30 mL/h). Ringer lactate 170 mL/hour was continuously given during the experiment.

Results

The two animals receiving lung transplants treated with ADC-1004 showed an improved oxygen tension after transplantation. As shown in FIG. 25 all pigs started around the same base line before transplantation. As early as 1 hour post transplantation the ADC-1004 treated animals showed an increase in oxygen gas exchange capacity in comparison with placebo treated animals, after 3 hours treated ADC-1004 animals had reached high oxygen gas exchange capacity indicating better lung condition compared to placebo treated animals. After 6 hours one of the control animals showed an increase in gas exchange capacity although not capable of reaching the levels in ADC-1004 treated pigs. The $PaO_2$ ($FiO_2$=1.0) in aortic blood after right pneumonectomy making the pig 100% dependant on the transplanted left lung is shown in Table 8.

These data indicate that lungs in the ADC-1004 treated group were in better condition 20 hours after transplantation compared to the placebo group. The better the gas-exchange capacity immediately after lung transplantation, the shorter will the need for intensive care treatment be and large clinical materials then show better 30-day survival. Impaired gas exchange capacity the first 24 hours after lung transplantation indicates reperfusion injury. Thus, indicating that ADC-1004 inhibition of the C5aR reduces the reperfusion injury in lung transplantation.

TABLE 8

$PaO_2$ ($FiO_2$ = 1.0) in aortic blood after right pneumonectomy.

| Control 1 | Control 2 | ADC-1004_1 | ADC-1004_2 |
|---|---|---|---|
| 30.4 | 46.6 | 67.2 | 50.2 |

REFERENCES

1. Granton J. Update of early respiratory failure in the lung transplant recipient. Curr Opin Crit Care 2006; 12:19-24.
2. McGregor C G, Daly R C, Peters S G, Midthun D E, Scott J P, Allen M S, et al. Evolving strategies in lung transplantation for emphysema. Ann Thorac Surg 1994; 57:1513-20.
3. Fiser S M, Tribble C G, Long S M, Kaza A K, Kern J A, Jones D R, et al. Ischemia-reperfusion injury after lung transplantation increases risk of late bronchiolitis obliterans syndrome. Ann Thorac Surg 2002; 73:1041-7.
4. Fiser S M, Tribble C G, Long S M, Kaza A K, Cope J T, Laubach V E, et al. Lung transplant reperfusion injury involves pulmonary macrophages and circulating leukocytes in a biphasic response. J Thorac Cardiovasc Surg 2001; 121:1069-75.
5. Leubach V E, Kron I L Pulmonary inflammation after lung transplantation. Surgery 2009; 146:1-4
6. Tomizawa N, Ohwada S, Ohya T, Takeyoshi I, Ogawa T, Kawashima Y, Adachi M, Morishita Y. The effects of a neutrophil elastase inhibitor (ONO-5046.Na) and neutrophil depletion using a granulotrap (G-1) column on lung reperfusion injury in dogs. J Heart Lung Transplant. 1999; 18:637-45
7. Ross S D, Tribble C G, Gaughen J R Jr, Shockey K S, Parrino P E, Kron I L. Reduced neutrophil infiltration protects against lung reperfusion injury after transplantation. Ann Thorac Surg. 1999; 67:1428-34
8. Steen S, Kimblad P O, Sjoberg T, Lindberg L, Ingemansson R, Massa G Safe lung preservation for twenty-four hours with Perfadex. Ann Thorac Surg 1994; 57:450-7

The invention claimed is:

1. A polypeptide having a biological activity of the Chemotaxis Inhibitory Protein of *Staphylococcus aureus* ('CHIPS'), the polypeptide comprising the amino acid sequence of SEQ ID NO: 2.

2. The polypeptide according to claim 1, wherein the polypeptide is between 70 and 110 amino acids in length.

3. The polypeptide according to claim 1, wherein the polypeptide consists of the amino acid sequence of SEQ ID NO: 2.

4. A pharmacological composition comprising a polypeptide according to claim 1.

5. A method for treating a subject in need of treatment with an inhibitor of a biological activity of complement 5a (C5a), wherein the treatment is for reperfusion injury or acute myocardial infarction, the method comprising administering to the subject in need of treatment a polypeptide according to claim 1.

6. The method according to claim 5 wherein the subject is human.

7. The method according to claim 5 wherein the reperfusion injury is associated with a condition selected from the group consisting of acute myocardial infarction (AMI), a coronary artery bypass graft (CABG), stroke and organ transplantation.

8. The method according to claim 5, comprising administering the polypeptide according to claim 1 as a single bolus dose.

9. The method according to claim 5, comprising administering the polypeptide according to claim 1 as a series of doses over time.

* * * * *